US008222285B2

(12) United States Patent
Chen et al.

(10) Patent No.: US 8,222,285 B2
(45) Date of Patent: Jul. 17, 2012

(54) 1,3-DIHYDROXY SUBSTITUTED PHENYLAMIDE GLUCOKINASE ACTIVATORS

(75) Inventors: Sean Chen, Princeton, NJ (US); Peter T. W. Cheng, Princeton, NJ (US); Rebecca A. Smirk, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 179 days.

(21) Appl. No.: 12/663,807

(22) PCT Filed: Jun. 11, 2008

(86) PCT No.: PCT/US2008/066510
§ 371 (c)(1),
(2), (4) Date: Mar. 22, 2010

(87) PCT Pub. No.: WO2008/154563
PCT Pub. Date: Dec. 18, 2008

(65) Prior Publication Data
US 2010/0179121 A1    Jul. 15, 2010

Related U.S. Application Data

(60) Provisional application No. 60/943,092, filed on Jun. 11, 2007.

(51) Int. Cl.
*A01N 43/78* (2006.01)
*A61K 31/425* (2006.01)
(52) U.S. Cl. ......... 514/369; 514/371; 548/182; 548/185
(58) Field of Classification Search .................. None
See application file for complete search history.

(56) References Cited

U.S. PATENT DOCUMENTS

| | | | |
|---|---|---|---|
| 6,184,237 B1 * | 2/2001 | Mantlo et al. ........... | 514/335 |
| 2008/0009465 A1 | 1/2008 | Ryono et al. | |
| 2008/0021052 A1 | 1/2008 | Chen et al. | |
| 2009/0030046 A1 | 1/2009 | Shi et al. | |

FOREIGN PATENT DOCUMENTS

| | | | |
|---|---|---|---|
| WO | WO99/20618 A1 | | 4/1999 |
| WO | WO 00/27826 | * | 5/2000 |
| WO | WO03/015774 A1 | | 2/2003 |
| WO | WO2007/007041 A1 | | 1/2007 |
| WO | WO2008/005914 A2 | | 1/2008 |
| WO | WO 2008/005964 | * | 1/2008 |
| WO | WO2008/005964 A2 | | 1/2008 |
| WO | WO2008/154563 A1 | | 12/2008 |
| WO | WO2009/018065 A2 | | 2/2009 |

OTHER PUBLICATIONS

U.S. Appl. No. 61/323,957, filed Apr. 14, 2010, Meng, et al.
U.S. Appl. No. 12/663,807, filed Jun. 10, 2008, Chen, et al.

* cited by examiner

*Primary Examiner* — Andrew D Kosar
*Assistant Examiner* — Valerie Rodriguez-Garcia
(74) *Attorney, Agent, or Firm* — Burton Rodney; Gary D. Greenblatt; Maureen S. Gibbons

(57) ABSTRACT

Compounds are provided which are glucokinase activators and thus are useful in treating diabetes and related diseases and have the structure wherein in the ring represents one or two double bonds; $R_1$ is alkyl, aryl, arylalkyl, heteroaryl, or heteroarylalkyl; $R_2$ is alkyl, aryl, arylalkyl, heteroaryl, or heteroarylalkyl; $R_5$ is as defined herein; Z is O, S, S(O), S(O)2, or $NR_{5a}$; X is S, O, N, $NR_3$, or $CR_3$; Y is $NCR_4$ or $NR_4$; $R_3$, $R_4$, and $R_5$ are as defined herein; $R_8$ is aryl, heteroaryl, —PO($OR_9$)($OR_{10}$), —PO($OR_9$)$R_{10}$ or —P(O)($R_9$)$R_{10}$ (wherein $R_9$ and $R_{10}$ are as defined herein/$R_6$ and $R_7$ are independently H, halogen, or alkyl; m is 0 or 1; and n is 0 to 3, or a pharmaceutically acceptable salt thereof. A method for treating diabetes and related diseases employing the above compounds is also provided.

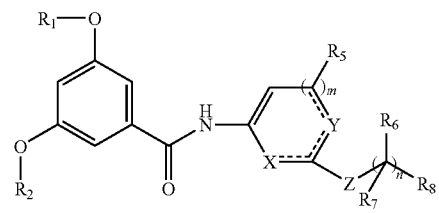

17 Claims, No Drawings

1,3-DIHYDROXY SUBSTITUTED PHENYLAMIDE GLUCOKINASE ACTIVATORS

FIELD OF THE INVENTION

The present invention relates to novel compounds which are activators of the enzyme glucokinase and thus are useful in treating diabetes, and to a method for treating diabetes, especially Type II diabetes, using such compounds.

BACKGROUND OF THE INVENTION

The enzyme glucokinase (GK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al. (*Biochem. J.*, 309:167-173 (1995)) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g., Matschinsky, F. M. et al., *Diabetes*, 55:1 (2006), and *Glucokinase and Glycemic Disease, from Basics to Novel Therapeutics*, published by Karger, Matschinsky, F. M. et al., eds., Ch. 6, pp. 360-378 (2004)). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker in acute single-dose studies and also effectively improved the glucose excursion in both normal C57/BL6J and ob/ob mice in oral glucose tolerance tests (e.g., in *Glucokinase and Glycemic Disease, from Basics to Novel Therapeutics*, published by Karger, Matschinsky, F. M. et al., eds., Ch. 6, pp. 360-378 (2004) as well as Fyfe, M. C. et al., *Diabetologia*, 50:1277 (2007)).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., *Diabetologia*, 50:1277 (2007)). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group (*Glucokinase and Glycemic Disease, from Basics to Novel Therapeutics*, published by Karger, Matschinsky, F. M. et al., eds., Ch. 6, pp. 360-378 (2004)).

SUMMARY OF THE INVENTION

In accordance with one aspect of the invention, compounds are provided having the structure I wherein in the ring represents one or two double bonds;
$R_1$ is selected from
  alkyl,
  aryl,
  arylalkyl,
  heteroaryl, or
  heteroarylalkyl;
$R_2$ is selected from
  alkyl,
  aryl,
  arylalkyl,
  heteroaryl, or
  heteroarylalkyl;
X is selected from
  S,
  O,
  N,
  $NR_3$, or
  $CR_3$;
Y is selected from
  N,
  $CR_4$, or
  $NR_4$;
Z is selected from
  O,
  S,
  S(O),
  $S(O)_2$, or
  $NR_{5a}$;
$R_3$, $R_4$, and $R_5$ are the same or different and are independently selected from
  H,
  halogen,
  alkyl,
  aryl,
  heteroaryl,
  arylalkyl, or
  heteroarylalkyl;
  however, when X is $NR_3$ or Y is $NR_4$, $R_3$ and $R_4$ are not halogen;

$R_{5a}$ is selected from
  H,
  alkyl, or
  aryl;
$R_6$ and $R_7$ are the same or different and are independently selected from
  hydrogen,
  halogen (preferably F), or
  alkyl;
$R_8$ is selected from
  aryl,
  heteroaryl,
  —PO(OR$_9$)(OR$_{10}$),
  —PO(OR$_9$)R$_{10}$, or
  —PO(R$_9$)R$_{10}$;
$R_9$ and $R_{10}$ are the same or different and are independently selected from hydrogen and alkyl;
m is 0 or 1;
n is 0, 1, 2, or 3;
stereoisomers thereof, a prodrug ester thereof, or a pharmaceutically acceptable salt thereof;
with the proviso that
where Z is O, S, S(O) or S(O)$_2$, then $R_8$ must be substituted with a substituent selected from 1) 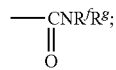

2) 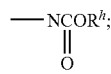

3) 

4) 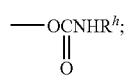

5) alkoxy;

6) tetrazolyl;

7) 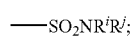

8) CN;

9) 

10) 

11) halo (such as Cl, F, CF$_3$);

12) 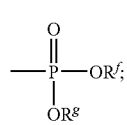

13) alkyl;

14) 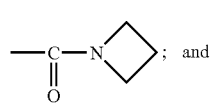 ; and

15) 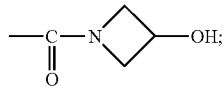

where R$^f$ and R$^g$ are independently selected from H, alkyl and aryl;
R$^h$ is alkyl or aryl; and
R$^i$ and R$^j$ are independently selected from H, alkyl and aryl, provided that at least one of R$^i$ and R$^j$ is other than H.

It will be appreciated that when Z is NR$_{5a}$, the R$_8$ group may be substituted with any of the above 1) to 15) groups as well as other substituents disclosed herein.

Examples of moieties of the structure

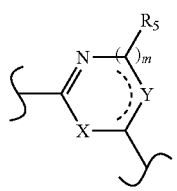

which may be present in the formula I compounds including but are not limited to

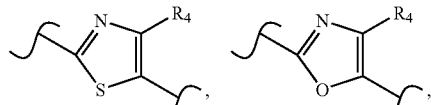

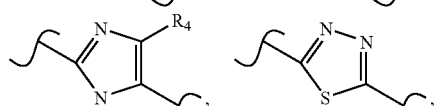

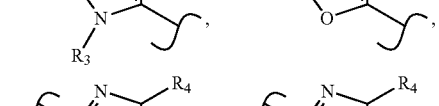

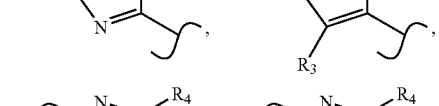

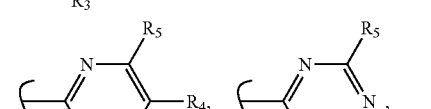

-continued

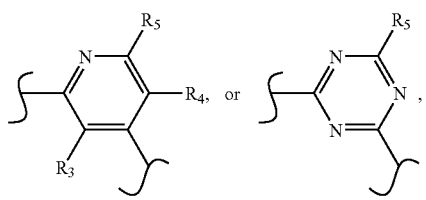

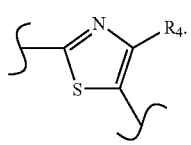

Preferred compounds of the invention have the structure Ia

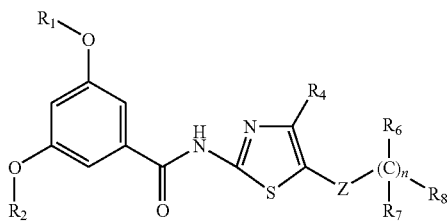

wherein $R_1$, $R_2$, $R_4$, $R_5$, $R_6$, $R_7$, $R_8$, Z, and n are as defined above for compounds of formula I; and Z is O, S or $S(O)_2$, or Z is O or $NR_{5a}$.

In more preferred compounds of formulas I and Ia of the invention $R_4$, $R_5$, $R_6$, and $R_7$ are each H;

$R_8$ is phenyl or heteroaryl (such as 2-pyridyl, 3-pyridyl, or 2,4-pyrimidyl), either of which is substituted with one or two groups selected from CN, alkyl, —$CONR^fR^g$,

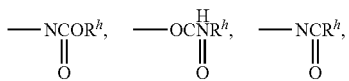

alkoxy, tetrazolyl, and $SO_2NR^iR^j$, where Z is O, $R_8$ may be substituted as above and/or with $CO_2H$, $CO_2$alkyl, halogen,

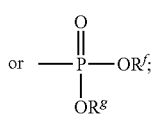

$R_1$ is alkoxyalkyl, hydroxyalkyl, alkyl, heteroaryl or haloheteroaryl;

$R_2$ is aryl, alkylsulfonylaryl, alkyl, arylalkyl, heterocyclocarbonylheteroaryl or alkylsulfonylheteroaryl; and Z is O, S, or $SO_2$.

In still more preferred compounds of the invention
$R_1$ is alkoxyalkyl, hydroxyalkyl or alkyl;

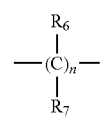

or heterocyclocarbonylheteroaryl;

Z is S, O, or $SO_2$;

is $CH_2$ or a bond; and $R_8$ is heteroaryl such as 2-pyridyl, 3-pyridyl or 2,4-pyrimidyl, or phenyl which are substituted with one or two groups selected from CN, —$CONR^fR^g$,

alkoxy, tetrazolyl, alkyl, halo, $CF_3$, and —$SO_2NR_iR^j$; where Z is O, $R_8$ may be substituted as above and/or with $CO_2$alkyl, $CO_2H$ or halogen.

In still more preferred compounds of formula Ia of the invention $R_1$ is $CH_3OCH_2CH(CH_3)$—, $HOCH_2CH(CH_3)$—, i-$C_3H_7$, $CH_3$

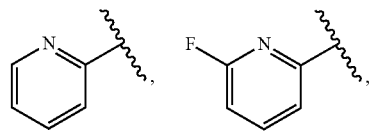

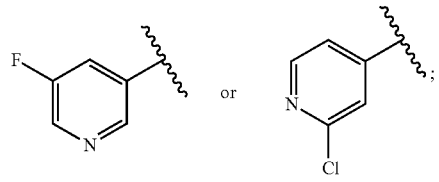

$R_2$ is , i-$C_3H_7$, $CH_3$,

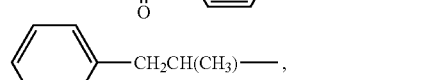

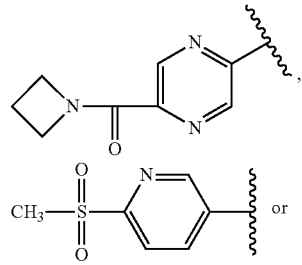

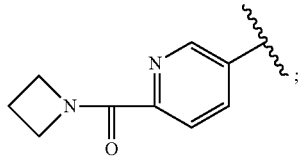
R₃ is H;
R₄ is H;
R₅ is H;
X is S;
Y is C;
m is 0;
Z is O;
n is 0 or 1;
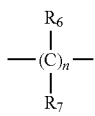
is CH₂ or a bond; and
R₈ is 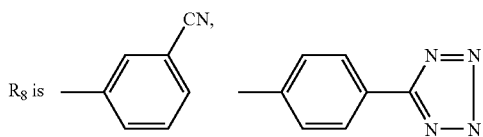
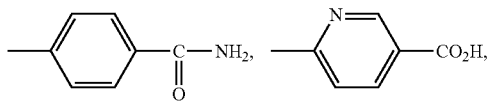
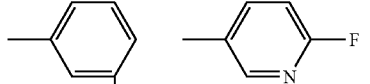
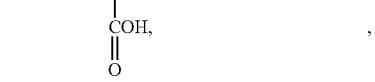
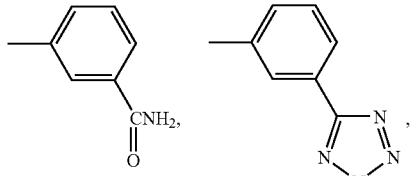
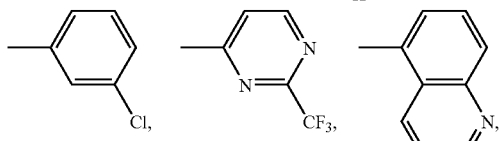
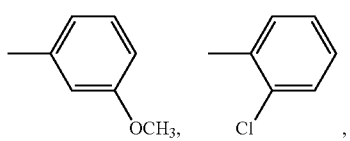
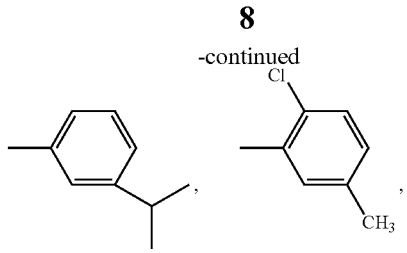
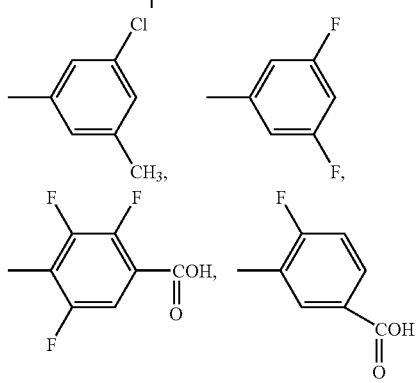
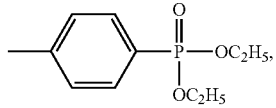
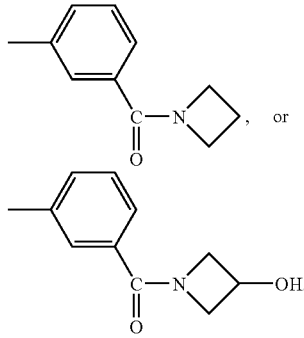, or
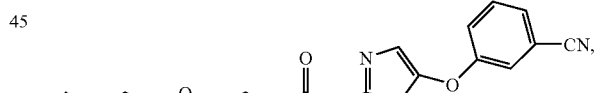
Examples of preferred compounds of the invention include
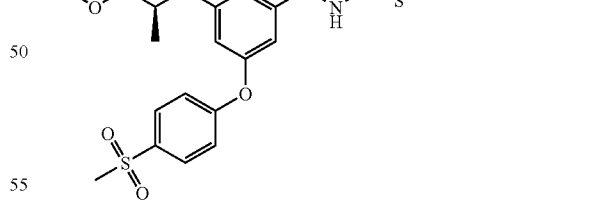
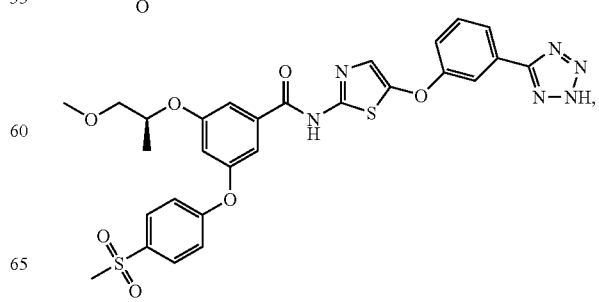

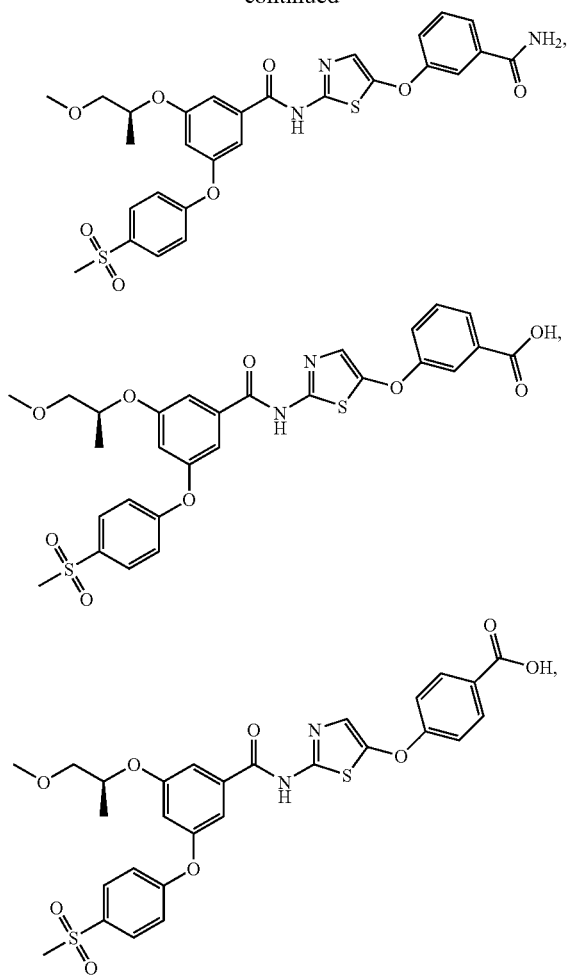
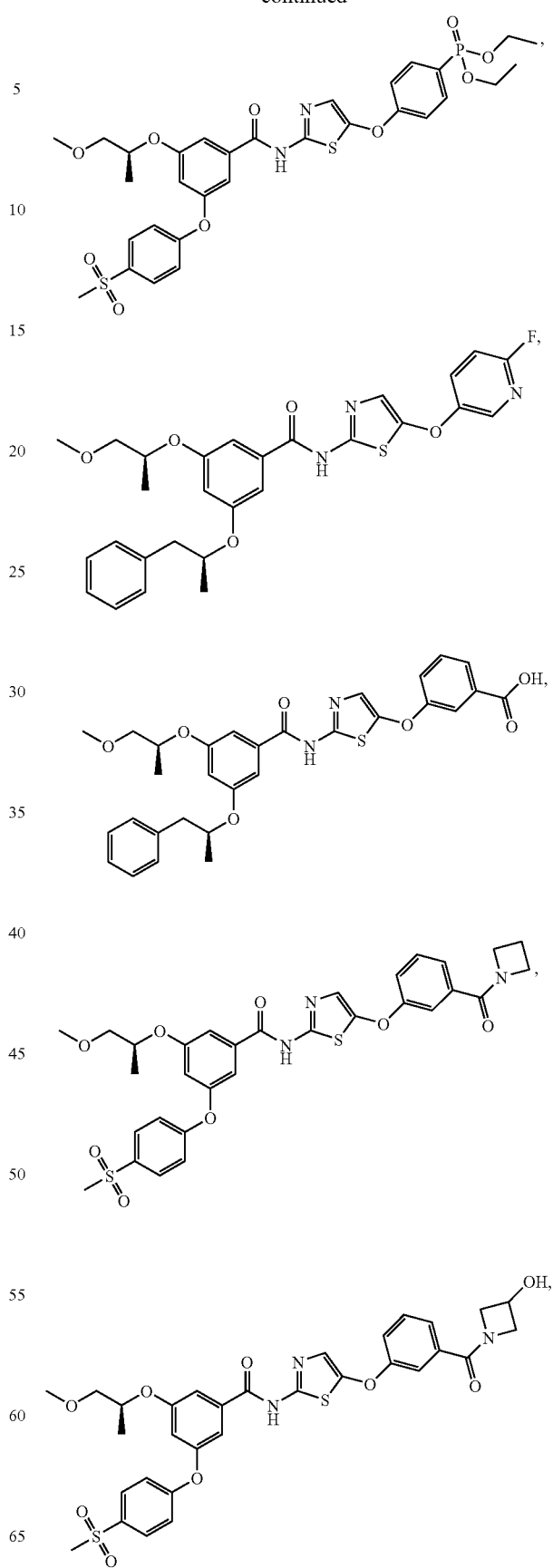

The compounds of the present invention activate or enhance the activity of the enzyme glucokinase. Consequently, the compounds of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for compounds of formula I, pharmaceutical compositions employing such compounds, and for methods of using such compounds. In particular, the present invention provides a pharmaceutical composition containing a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other therapeutic agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

In another embodiment, compounds of the present invention are selected from the compounds exemplified in the examples.

In another embodiment, the present invention relates to pharmaceutical compositions which include of a therapeutically effective amount of a compound of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, $C=N$ double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., $=O$), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like; such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio, as well as (=O), $OR_a$, $SR_a$, (=S), $-NR_aR_b$, $-N(alkyl)_3^+$, $-NR_aSO_2$, $-NR_aSO_2R_c$, $-SO_2R_c$— $SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}$alkylene$)NR_aR_b$, $-C(=O)NR_a(SO_2)R_b$, $-CO_2(C_{1-4}$alkylene$)NR_aR_b$, $-NR_aC(=O)R_b$, $-NR_aCO_2R_b$, $-NR_a(C_{1-4}$alkylene$)CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_{1-6})$alkyl, $(C_{2-6})$alkenyl, hydroxy, halogen, cyano, nitro, $CF_3$, $O(C_{1-6}$alkyl$)$, $OCF_3$, $C(=O)H$, $C(=O)(C_{1-6}$alkyl$)$, $CO_2H$, $CO_2(C_{1-6}$alkyl$)$, $NHCO_2(C_{1-6}$alkyl$)$, $-S(C_{1-6}$alkyl$)$, $-NH_2$, $NH(C_{1-6}$alkyl$)$, $N(C_{1-6}$alkyl$)_2$, $N(CH_3)_3^+$, $SO_2(C_{1-6}$alkyl$)$, $C(=O)(C_{1-4}$alkylene$)NH_2$, $C(=O)$ $(C_{1-4}$alkylene$)NH($alkyl$)$, $C(=O)(C_{1-4}$alkylene$)$ $N(C_{1-4}$alkyl$)_2$, $C_{3-7}$cycloalkyl, phenyl, benzyl, phenylethyl, phenyloxy, benzyloxy, naphthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

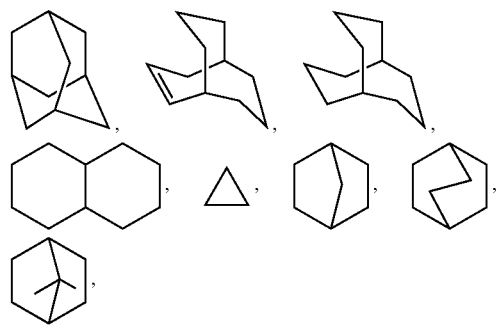

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl, biphenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings)

for example

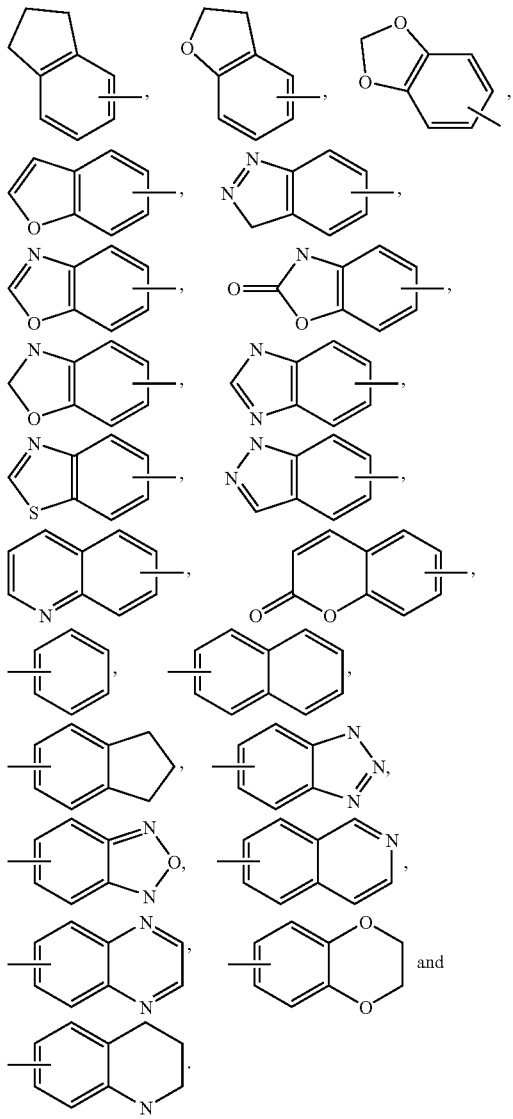

The aryl group may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}\text{alkylene})NR_aR_b$, $-C(=O)NR_a(SO_2)R_b$, $-CO_2(C_{1-4}\text{alkylene})NR_aR_b$, $-NR_aC(=O)R_b$, $-NR_aCO_2R_b$, $-NR_a(C_{1-4}\text{alkylene})CO_2R_b$, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}\text{alkyl})$, $OCF_3$, $C(=O)H$, $C(=O)(C_{1-4}\text{alkyl})$, $CO_2H$, $CO_2(C_{1-4}\text{alkyl})$, $NHCO_2(C_{1-4}\text{alkyl})$, $-S(C_{1-4}\text{alkyl})$, $-NH_2$, $NH(C_{1-4}\text{alkyl})$, $N(C_{1-4}\text{alkyl})_2$, $N(C_{1-4}\text{alkyl})_3^+$, $SO_2(C_{1-4}\text{alkyl})$, $C(=O)(C_{1-4}\text{alkylene})NH_2$, $C(=O)(C_{1-4}\text{alkylene})NH(\text{alkyl})$, and/or $C(=O)(C_{1-4}\text{alkylene})N(C_{1-4}\text{alkyl})_2$, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R_3$ groups or substituents for $R_3$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

The term "acyl" alone or as part of another group refers to a carbonyl group linked to an organic radical, more particularly, the group $C(=O)R_e$, as well as the bivalent groups $-C(=O)-$ or $-C(=O)R_e-$, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The term "heterocyclo" or "heterocyclic" or "heterocyclyl" or "cycloheteroalkyl" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S, or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)$ $R_b$, $SO_3H$, —$PO(OH)_2$, —$C(=O)R_a$, —$CO_2R_a$, —$C(=O)$ $NR_aR_b$, —$C(=O)(C_{1-4}alkylene)NR_aR_b$, —$C(=O)NR_a$ $(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$, and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4}$alkenyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$alkyl), $C(=O)$ $(C_{1-4}$alkylene)$NH_2$, $C(=O)(C_{1-4}$alkylene)NH(alkyl), and/or $C(=O)(C_{1-4}$alkylene)N$(C_{1-4}$alkyl$)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like. Exemplary bicyclic heterocyclo groups include quinuclidinyl.

Preferred heterocyclo groups in compounds of formula (I) include

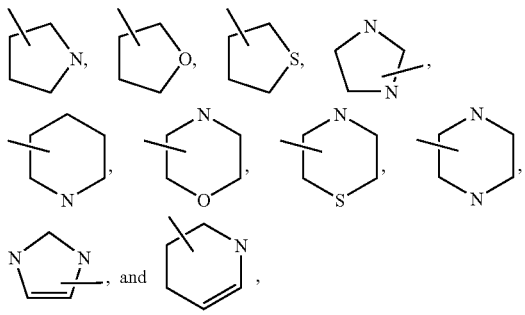

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated, and may include aryl, cycloalkyl, heteroaryl or cycloheteroalkyl groups. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents which may be any of the substituents set out for alkyl and can be selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)$ $R_b$, $SO_3H$, —$PO(OH)_2$, —$C(=O)R_a$, —$CO_2R_a$, —$C(=O)$ $NR_aR_b$, —$C(=O)(C_{1-4}alkylene)NR_aR_b$, —$C(=O)NR_a$ $(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4}$alkenyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$alkyl), $C(=O)(C_{1-4}$alkylene)$NH_2$, $C(=O)$ $(C_{1-4}$alkylene)NH(alkyl), and/or $C(=O)(C_{1-4}$alkylene)N $(C_{1-4}$alkyl$)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

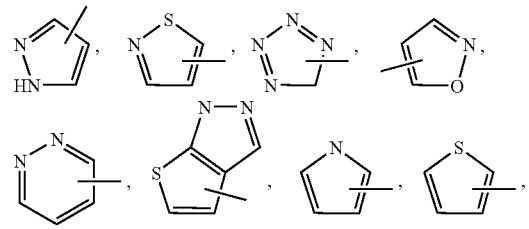

and the like.

The term "heterocyclylalkyl" or "heterocycloalkyl" or "cycloheteroalkylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an —OH group.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se.

Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl, or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

Prodrug ester examples include the following groups:

(1-alkanoyloxyalkyl such as

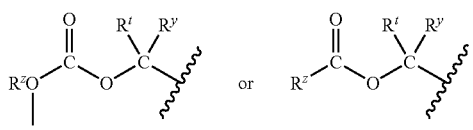

wherein $R^z$, $R^t$, and $R^y$ are H, alkyl, aryl, or arylalkyl; however, $R^zO$ cannot be HO.

Examples of such prodrug esters include
$CH_3{}^{CO}{}_2CH_2$—, $$CH_3CO_2CH_2\!-\!\!\underset{\underset{(CH_3)_2}{|}}{\overset{}{CH}}\!\!-,$$

$t\text{-}C_4H_9CO_2CH_2$—, or

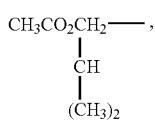

Other examples of suitable prodrug esters include

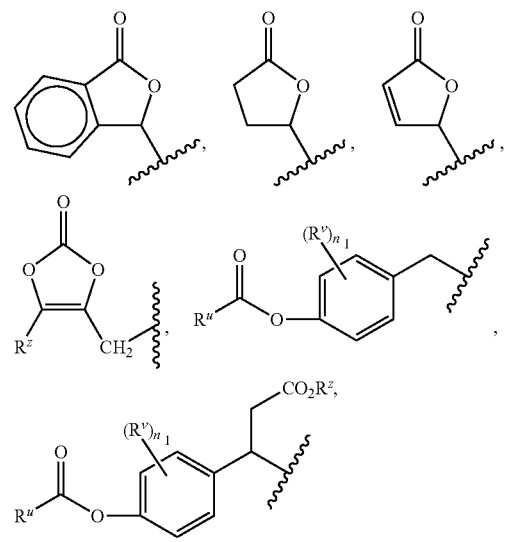

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl, or alkoxyl, and $n_1$ is 0, 1, or 2.

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

SYNTHESIS

Compounds of formulae I and Ia may be prepared as shown in the following reaction schemes and the description thereof, as well as relevant literature procedures that may be used by one skilled in the art. Exemplary reagents and procedures for these reactions appear hereinafter and in the working Examples.

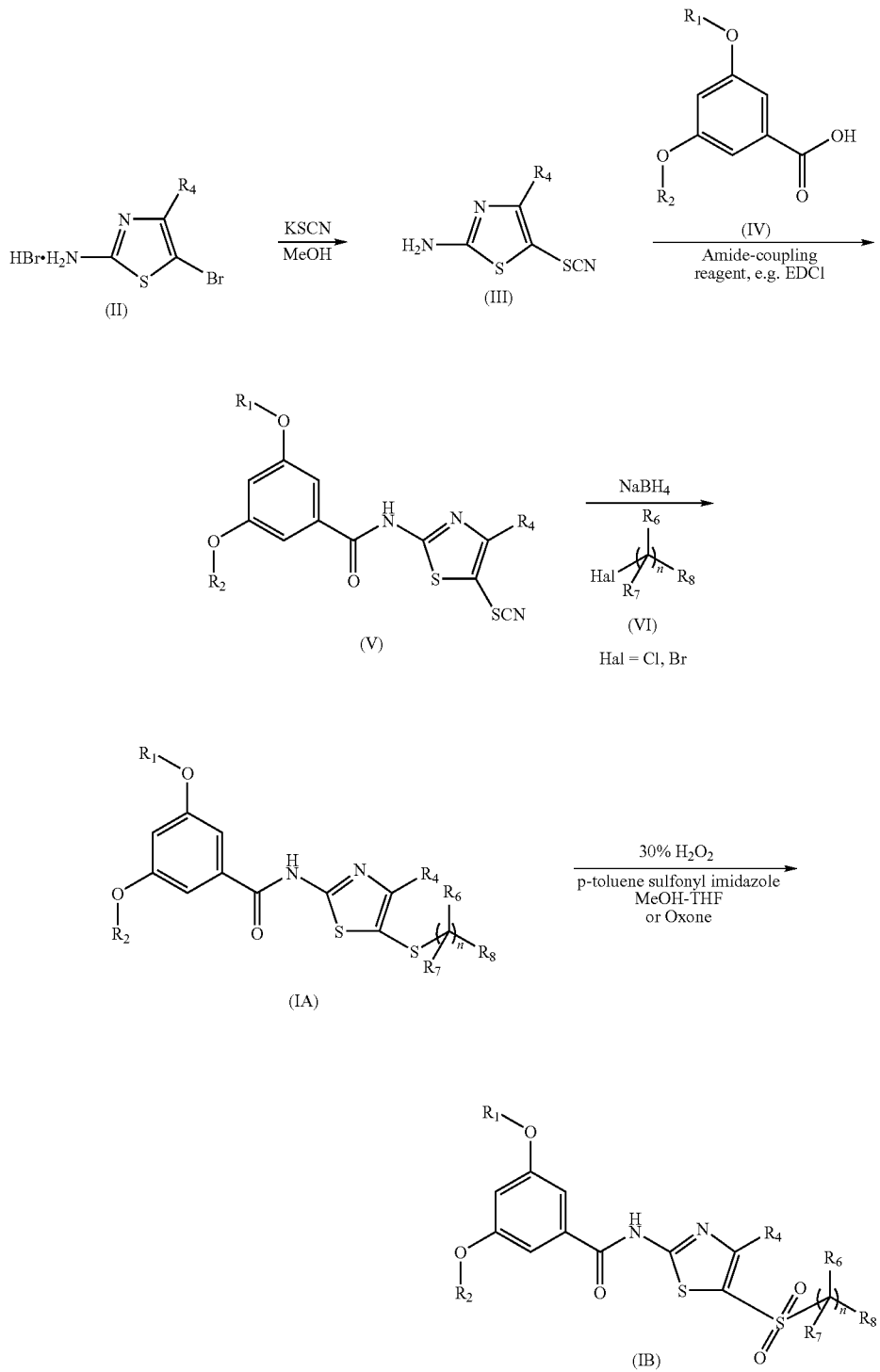

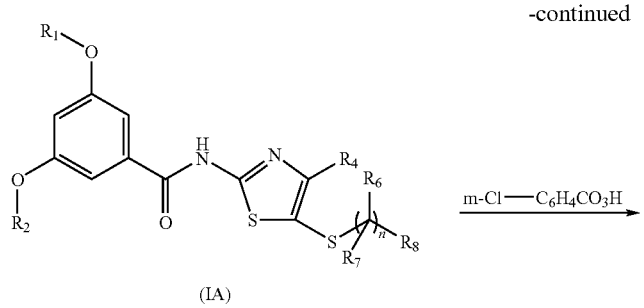

(IA)

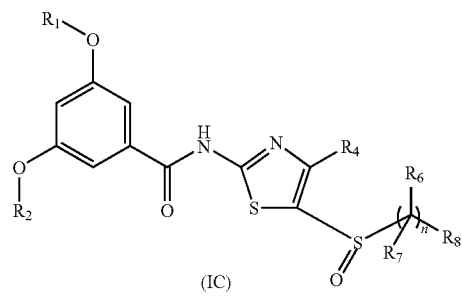

(IC)

Scheme 1 describes a method for preparing compounds of formulae IA, IB, and IC of the invention (subsets of compounds of formula I of the invention). The 5-thiocyanatothiazol-2-amine III can be obtained by the treatment of 2-amino-5-bromothiazole hydrobromide II with potassium thiocyanate. The amide V can be obtained from the reaction of amine III with an acid IV, for instance by following the procedure described in WO 02/46173, using appropriate amide coupling reagents, such as DEPBT, BOP, EDAC/HOBT, EDAC/HOAT, or PyBOP, or those reagents described in *The Practice of Peptide Synthesis* (Springer-Verlag, 2$^{nd}$ Ed., Bodanszky, Miklos (1993)). Reduction of the intermediate thiocyanate V with sodium borohydride followed by treatment of a chloride or bromide VI, which can be obtained commercially or are readily prepared by methods known in the literature or other methods used by one skilled in the art, provides the corresponding sulfides, which are compounds of formula IA (subsets of compounds of formula I). Subsequent oxidation of compounds IA with an appropriate oxidizing reagent such as H$_2$O$_2$/p-toluenesulfonyl imidazole, or Oxone®, or other reagents used by one skilled in the art provides the corresponding sulfones, which are compounds of formula IB (subsets of compounds of formula I). Additionally, oxidation of compounds IA with an appropriate oxidizing agent such as meta-chloroperbenzoic acid, or other agents used by one skilled in the art provides the corresponding sulfoxides, which are compounds of formula IC (subsets of compounds of formula I).

Scheme 2

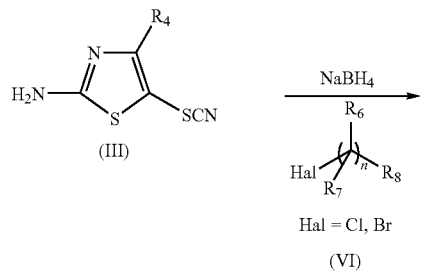

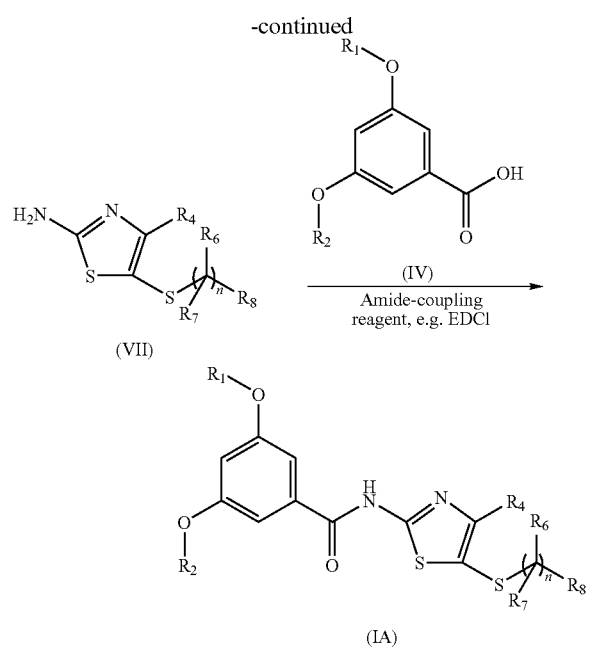

Scheme 2 describes an alternative method for preparing compounds of formula IA of the invention (subsets of compounds of formula I of the invention). Reduction of the intermediate thiocyanate III with sodium borohydride followed by treatment of a chloride or bromide VI, which are readily synthesized by methods known in the literature or other methods used by one skilled in the art, provides an intermediate thioalkyl thiazole VII. Amide IA can be obtained from the reaction of amine VII with an acid IV, for instance by following the procedure described in WO 02/46173, using appropriate amide coupling reagents, such as DEPBT, BOP, EDAC/HOBT, EDAC/HOAT, PyBOP, or those reagents described in *The Practice of Peptide Synthesis* (Springer-Verlag, 2$^{nd}$ Ed., Bodanszky, Miklos (1993)), to yield compounds of formula IA (subsets of compounds of formula I).

Scheme 3

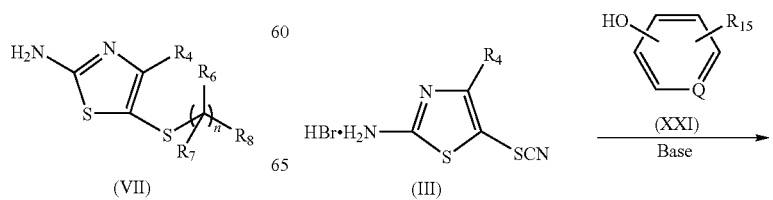

-continued

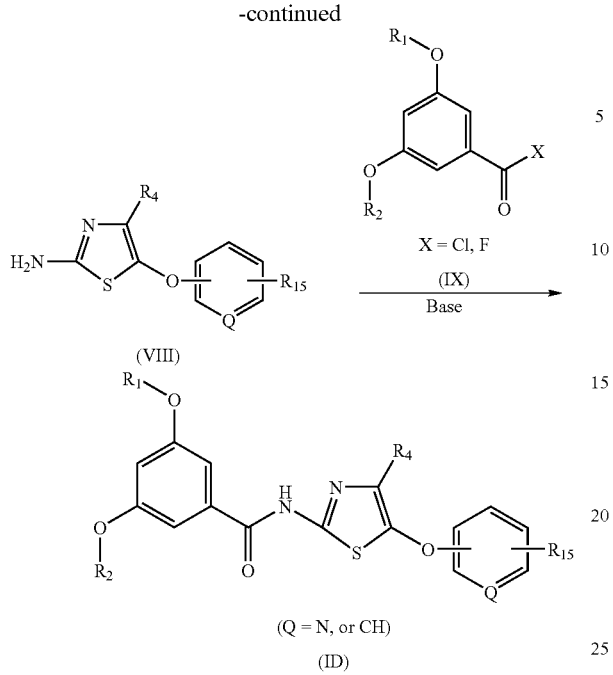

(Q = N, or CH)

(ID)

Q = N, CH
$R_{15}$ = CO$_2$H, tetrazole, alkyl, alkoxy, halogen, amino, OH, CN, CO$_2$R$^a$, CONR$^a$R$^b$, or PO(OEt)$_2$ where R$^a$ and R$^b$ are the same or different and are H or alkyl)

Scheme 3 describes a method for preparing compounds of formula ID of the invention (subsets of compounds of formula I of the invention). An aminothiazole intermediate VIII can be obtained by treatment of 2-amino-5-bromothiazole monohydrobromide II with the appropriately substituted hydroxybenzene or hydroxyheteroaryl compound XXI, which is readily synthesized by methods known in the literature or other methods used by one skilled in the art, in the presence of a base (for instance cesium carbonate in acetone at reflux; procedure described in WO 02/50071). The desired amide ID can be obtained from reaction of the amine VIII with an acid chloride or acid fluoride IX (prepared by treatment of the corresponding acid IV with oxalyl chloride/DMF or cyanuric fluoride/pyridine) using an appropriate base, such as pyridine, pyridine/DMAP, or NaHCO$_3$, to yield compounds of formula ID (subsets of compounds of formula I). Alternatively, amide 1D can be obtained from the reaction of amine VIII with the corresponding carboxylic acid IV using appropriate amide coupling reagents, such as BOP, EDAC/HOBT or EDAC/HOAT, PyBOP, etc.

Scheme 4

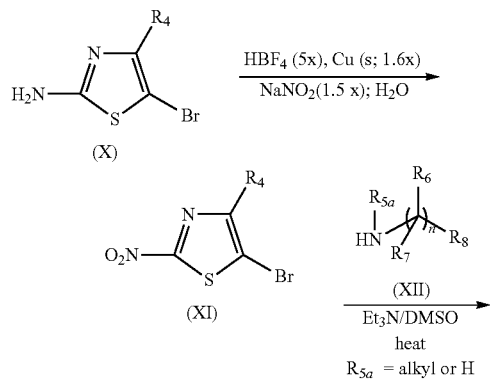

-continued

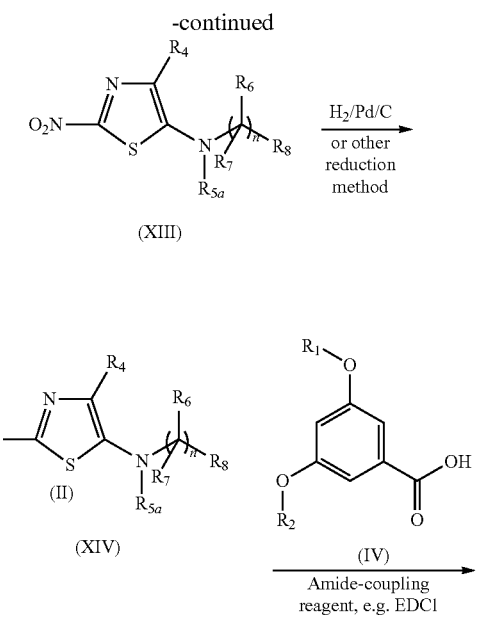

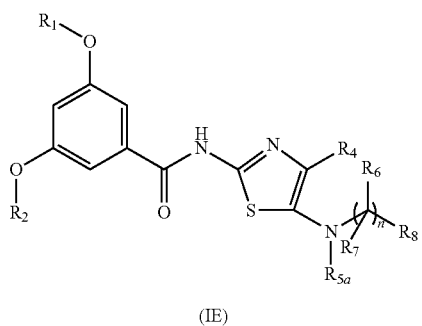

Scheme 4 describes a method for preparing compounds of formula IE of the invention (a subset of compounds of formula I of the invention). The 2-amino-5-bromothiazole X can be converted to the corresponding 2-nitro-5-bromothiazole XI (for instance, under typical Sandmeyer type conditions, e.g., Bioorg. Med. Chem. Lett., 14:5521-5525 (2004)). The bromothiazole XI can then be reacted with a variety of amines XII (including primary amines, where $R_{5a}$=H, and secondary amines, where $R_{5a}$=alkyl) in a displacement reaction to provide 5-amino-2-nitro-thiazoles XIII. The nitrothiazoles XIII can be reduced to the corresponding aminothiazoles XIV by a variety of methods, for instance hydrogenation or with sodium dithionite. The desired amide IE can then be obtained from the reaction of the aminothiazoles XIV with a carboxylic acid IV, for instance by following the procedure described in WO 2002/46173, using appropriate amide coupling reagents, such as DEPBT, BOP, EDAC/HOBT, EDAC/HOAT, PyBOP, or those reagents described in *The Practice of Peptide Synthesis* (Spring-Verlag, 2$^{nd}$ Ed., Bodanszky, Miklos (1993)). Alternatively, amide IE can be obtained from the reaction of aminothiazoles XIV with the corresponding acid chlorides IX obtained from acids IV (via, e.g., oxalyl chloride).

Scheme 5

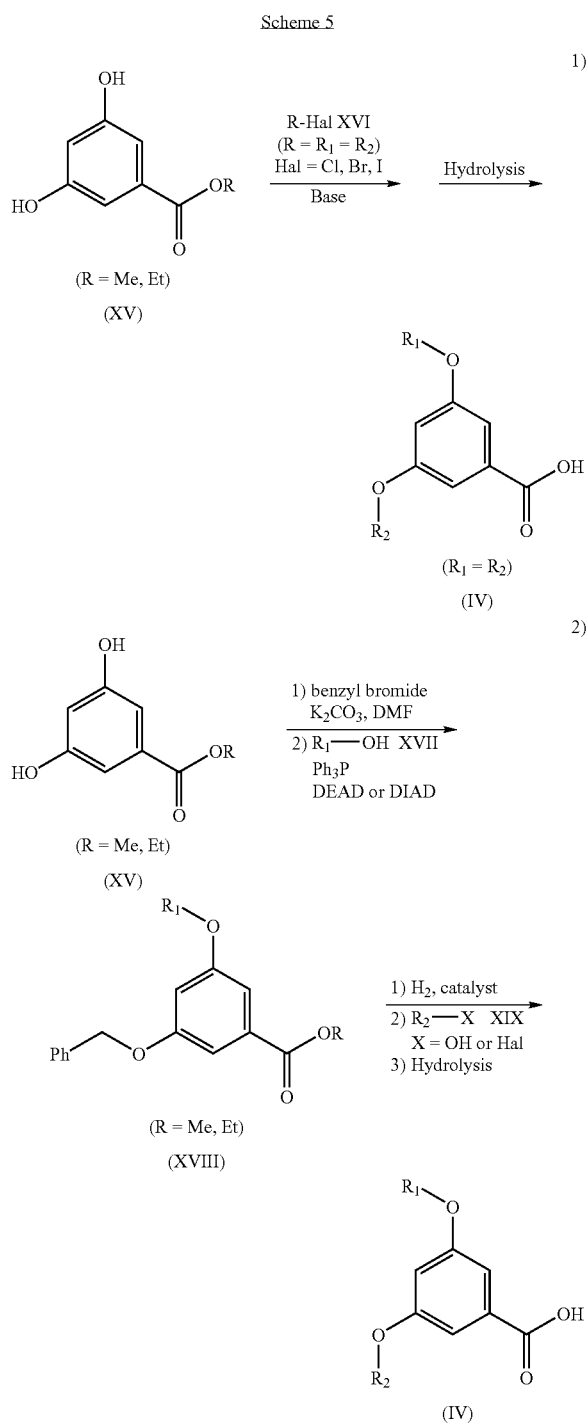

Scheme 6

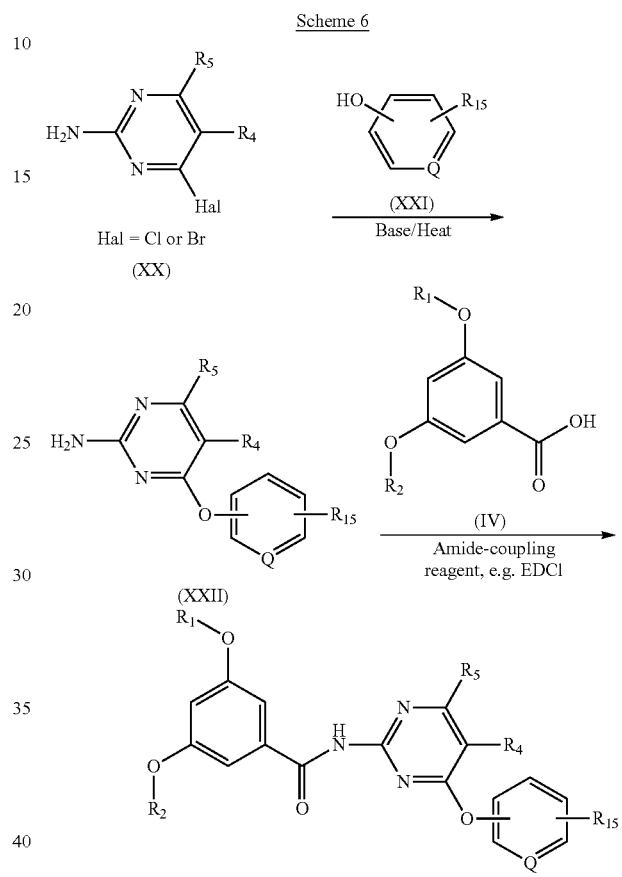

as described in WO 2005/121110, and followed by introducing the $R_1$ group via a Mitsunobu reaction [for reviews, see: *Synthesis*, 1 (1981); *Org. React.*, 42:335 (1992)]. Deprotection of benzyl ether XVIII followed by alkylation or Mitsunobu reaction with a halide $R_2$—X (XIX) and ester hydrolysis provides acids IV.

Q = N, CH
$R_{15}$ = $CO_2H$, tetrazole, alkyl, alkoxy, halogen, amino, CN, $CO_2R^a$, $CONR^aR^b$ where $R^a$ and $R^b$ are the same or different and are H or alkyl)

Carboxylic acids IV can be prepared through one of the following two routes shown in Scheme 5. In route 1 (when $R_1$=$R_2$), acids IV are prepared via a 2-step procedure involving: 1) alkylation of 3,5-dihydroxy benzoate XV with a halide XVI in the presence of a base (e.g., cesium carbonate, potassium carbonate, etc.), and 2) hydrolysis of the alkylated carboxylic acid derivative under either basic or acidic conditions. In route 2, when $R_1$ is different from $R_2$, selective monoprotection of one of the phenol groups can be achieved, for example, by alkylation of 3,5-dihydroxy benzoate XV with benzyl bromide in the presence of potassium carbonate, Scheme 6 describes a method for preparing compounds of formula IF of the invention (a subset of compounds of formula I of the invention). An aminopyrimidine intermediate XXII can be obtained by treatment of 2-amino-halopyrimidine XX with an appropriately substituted hydroxybenzene or hydroxyheteroaryl compound (XXI) which is readily synthesized by methods known in the literature or other methods used by one skilled in the art, in the presence of a base (for instance cesium carbonate in DMF with heating; procedure as described in *Bioorg. Med. Chem. Lett.*, 11:2185-2188 (2001)). The desired amide IF can be obtained from reaction of the aminopyrimidine XXII with an acid IV, for instance by following the procedure described in WO 2002/46173, using appropriate amide coupling reagents, such as DEPBT, BOP, EDAC/HOBT, EDAC/HOAT, PyBOP, or those reagents described in *The Practice of Peptide Synthesis* (Spring-Verlag, $2^{nd}$ Ed., Bodanszky, Miklos (1993)). Alternatively, amide IF can be obtained from the reaction of aminopyrimidine XXII with the corresponding acid chlorides IX obtained from acids IV (via reaction with, e.g., oxalyl chloride).

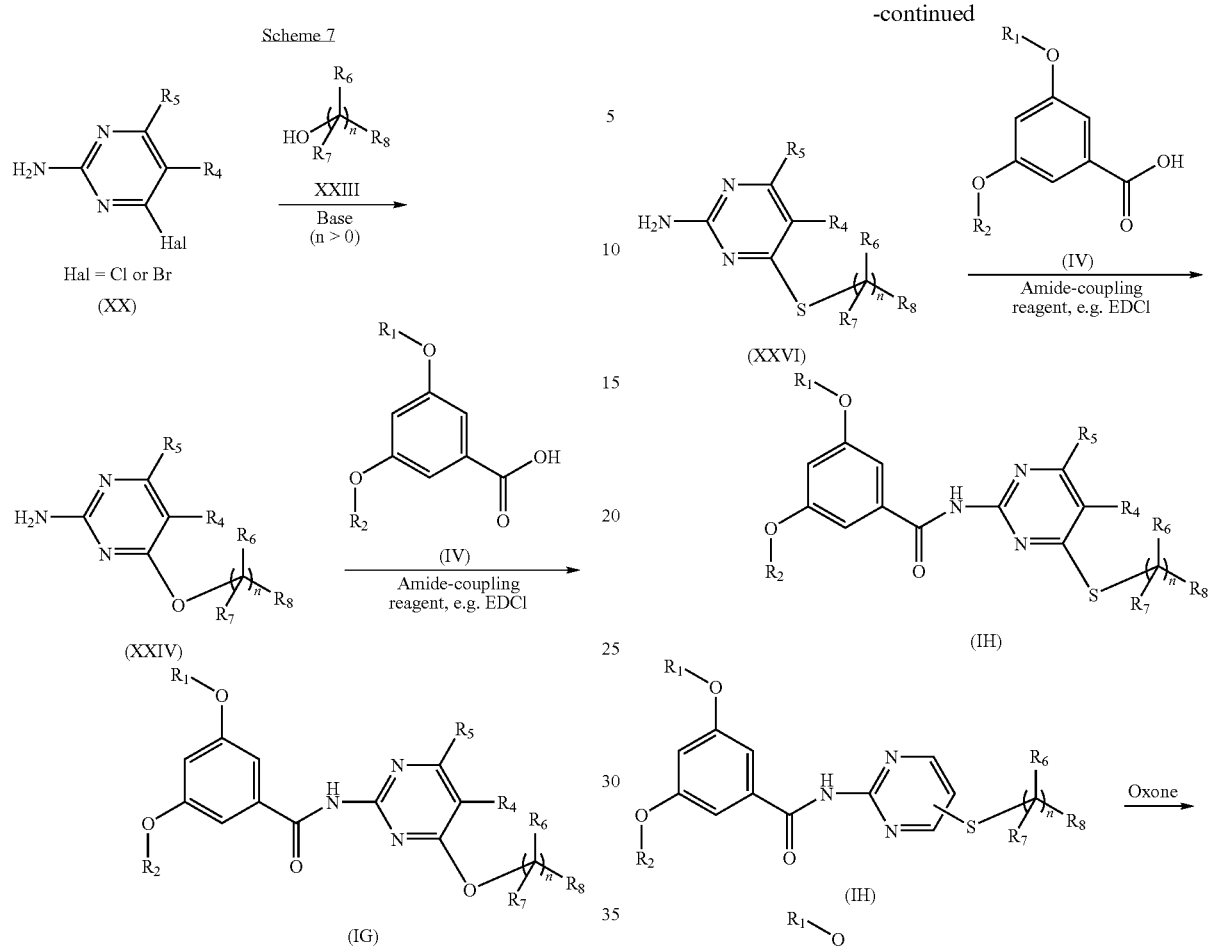

Scheme 7 describes a method for preparing compounds of formula IG of the invention (a subset of compounds of formula I of the invention). An aminopyrimidine intermediate XXIV can be obtained by treatment of an 2-amino-halopyrimidine XX with the alkoxide of an appropriately substituted alcohol (XXIII) (the alkoxide can be prepared from the reaction of the alcohol with an appropriate base, e.g., NaN(TMS)$_2$) with heating; as generally described in *J. Chem. Res.*, 747-749 (2005). The desired amide IG can be obtained from reaction of the aminopyrimidine XXIV with an acid IV, for instance by following the procedure described in WO 2002/46173, using appropriate amide coupling reagents, such as DEPBT, BOP, EDAC/HOBT, EDAC/HOAT, or PyBOP and the like as described for Scheme 6. Alternatively, amide IG can be obtained from the reaction of aminopyrimidine XXIV with the corresponding acid chlorides IX obtained from acids IV (via reaction with, e.g., oxalyl chloride).

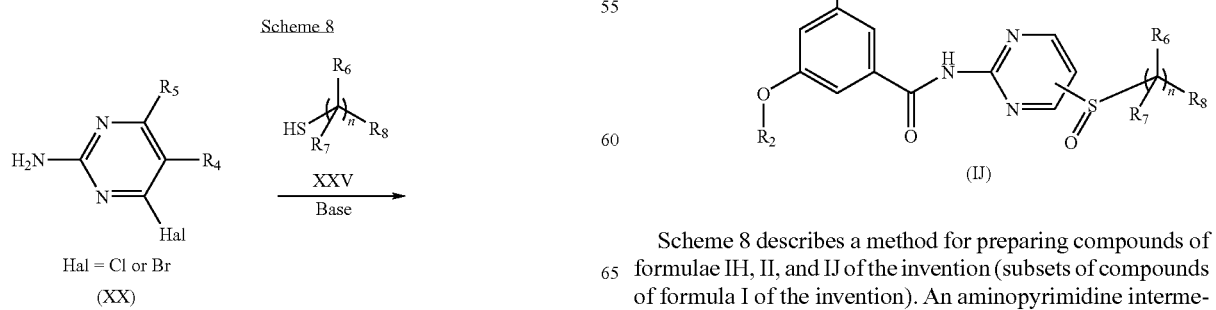

Scheme 8 describes a method for preparing compounds of formulae IH, II, and IJ of the invention (subsets of compounds of formula I of the invention). An aminopyrimidine intermediate XXVI can be obtained by treatment of an 2-aminohalopyrimidine XX with a thiolate (generated from a substituted thiol XXV using an appropriate base such as NaH or NaN(TMS)$_2$). The amide 1H can be obtained from the reaction of amine XXVI with an acid IV, for instance by following the procedure described in WO 02/46173, using appropriate amide coupling reagents, such as DEPBT, BOP, EDAC/HOBT, EDAC/HOAT, or PyBOP, or those reagents described in *The Practice of Peptide Synthesis* (Spring-Verlag, 2$^{nd}$ Ed., Bodanszky, Miklos (1993)). Alternatively, amide IH can be obtained from the reaction of amine XXVI with the corresponding acid chlorides IX obtained from acids IV (via reaction with, e.g., oxalyl chloride). Subsequent oxidation of sulfide-containing compounds IH with an appropriate oxidizing reagent such as Oxone®, or other reagents used by one skilled in the art provides the corresponding sulfones, which are compounds of formula II (subsets of compounds of formula I). Additionally, oxidation of compounds IH with an appropriate oxidizing agent such as meta-chloroperbenzoic acid, or other agents used by one skilled in the art provides the corresponding sulfoxides, which are compounds of formula IJ (subsets of compounds of formula I).

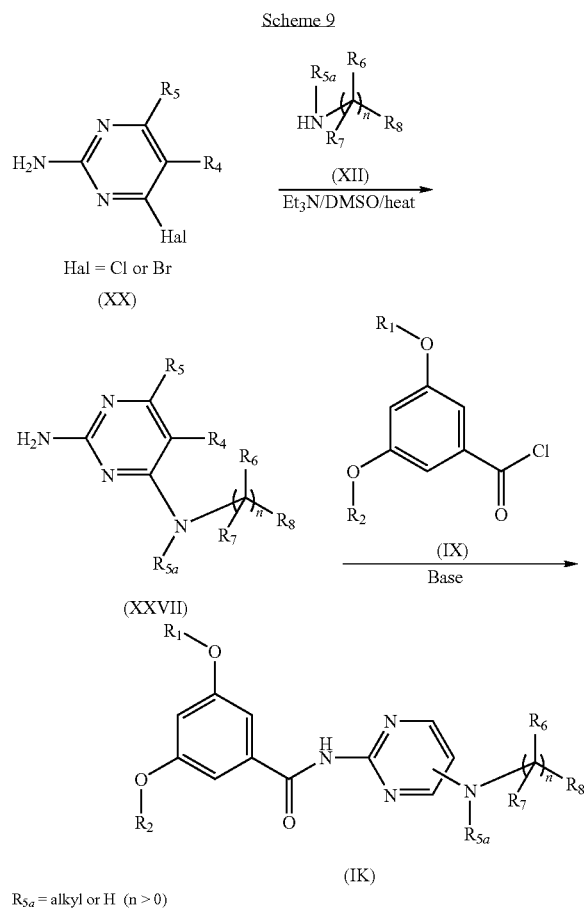

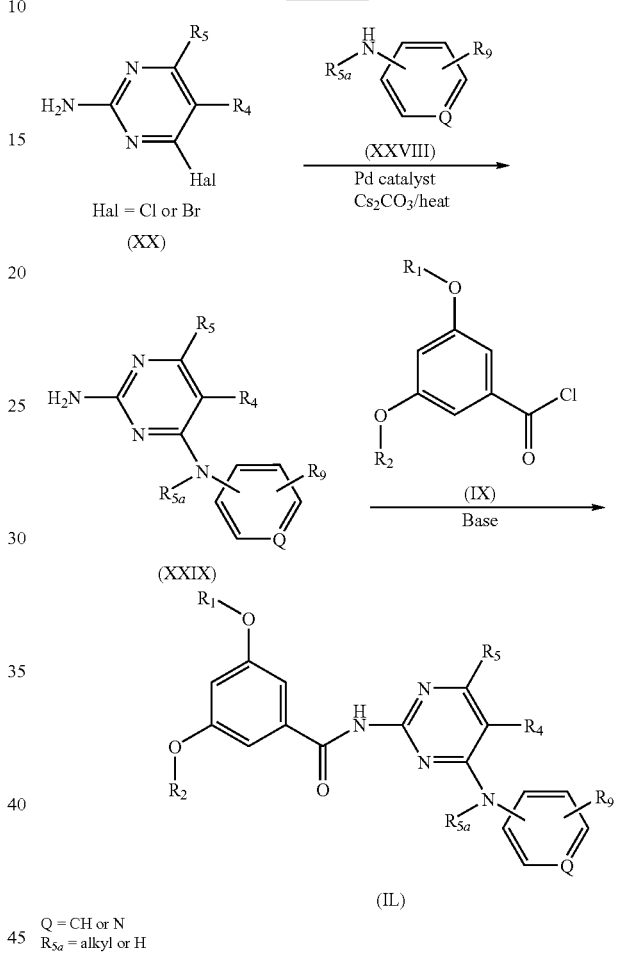

Scheme 9 describes a method for preparing compounds of formula IK of the invention (a subset of compounds of formula I of the invention). An aminopyrimidine intermediate XXVII can be obtained by treatment of an 2-amino-halopyrimidine XX with a primary or secondary amine with heating in the presence of a tertiary amine (for example, as in *J. Am. Chem. Soc.*, 124:1594-1596 (2002)). The desired amide IK can be obtained from reaction of the aminopyrimidine XXVII with an acid chloride IX (prepared by treatment of the corresponding acid IV with oxalyl chloride/DMF) in the presence of an appropriate base. Alternatively, amide IK can be obtained from the reaction of aminopyrimidine XXVII with the corresponding carboxylic acid IV using appropriate amide coupling reagents, such as BOP, EDAC/HOBT, EDAC/HOAT, or PyBOP, as described for Scheme 6.

Scheme 10 describes a method for preparing compounds of formula IL of the invention (a subset of compounds of formula I of the invention). An aminopyrimidine intermediate XXIX can be obtained by treatment of 2-amino-halopyrimidine XX with an appropriately substituted aniline or aminoheteroaryl compound (XXVIII) which is readily synthesized by methods known in the literature or other methods used by one skilled in the art, in the presence of a base and a palladium catalyst with an appropriate ligand (for instance cesium carbonate and Pd$_2$(dba)$_3$/DPPF with heating; procedure as described in *J. Med. Chem.*, 48:4892-4909 (2005)). The desired amide IL can be obtained from reaction of the aminopyrimidine XXIX with an acid chloride IX obtained from acids IV (via reaction with, e.g., oxalyl chloride) in the presence of a base. Alternatively, amide IL can be obtained from reaction of aminopyrimidine XXIX with an acid IV by following the procedure from WO 2002/46173, using appropriate amide coupling reagents, such as DEPBT, BOP, EDAC/HOBT, EDAC/HOAT, or PyBOP, or those reagents described in *The Practice of Peptide Synthesis* (Spring-Verlag, 2$^{nd}$ Ed., Bodanszky, Miklos (1993)).

It will be appreciated in Schemes I to 10 any of the ring systems

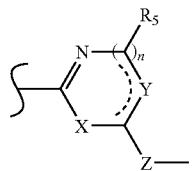

as defined above may be employed in place of the thiazole ring system and pyrimidine ring system to produce corresponding compounds I of the invention.

UTILITIES AND COMBINATIONS

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other enhancers of activity of glucokinase or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-infective agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-ischemic agents, anti-cancer agents, anti-cytotoxic agents, anti-restenotic agents, anti-pancreatic agents, lipid lowering agents, appetite suppressants, memory enhancing agents, and cognitive agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones (PPARgamma agonists): ciglitazone, pioglitazone, troglitazone, rosiglitazone; non-thiazolidinedione PPAR-gamma agonists; selective PPARgamma modulators (SPPARMs; e.g., metaglidasen from Metabolex); PPAR-alpha agonists; PPAR alpha/gamma dual agonists; PPAR delta agonists, PPARalpha/gamma/delta pan agonists; SGLT2 inhibitors; dipeptidyl peptidase-IV (DPP4) inhibitors; aldose reductase inhibitors; RXR agonists: JTT-501, MX-6054, DRF2593, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's farglitazar (GI-262570), englitazone (CP-68722, Pfizer), or darglitazone (CP-86325, Pfizer), isaglitazone (MIT/J&J), JTT-501 (JPNT/P&U), L-895645 (Merck), R-119702 (Sankyo/WL), N,N-2344 or balaglitazone (Dr. Reddy/NN), or YM-440 (Yamanouchi).

Suitable PPAR alpha/gamma dual agonists include muraglitazar (Bristol-Myers Squibb), tesaglitazar (Astra/Zeneca), naveglitazar (Lilly/Ligand); AVE-0847 (Sanofi-Aventis); TAK-654 (Takeda), as well as those disclosed by Murakami et al., "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes*, 47:1841-1847 (1998), WO 01/21602 and U.S. Pat. No. 6,414,002, the disclosure of which is incorporated herein by reference, employing dosages as set out therein, which compounds designated as preferred are preferred for use herein. Suitable PPARdelta agonists include, for example, GW-501516 (Glaxo). Suitable PPARalpha/gamma/delta pan agonists include, for example, GW-677954 (Glaxo).

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptin (Bristol-Myers Squibb), vildagliptin (Novartis) and sitagliptin (Merck) as well as those disclosed in WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38(36):11597-11603 (1999), TSL-225 (tryptophyl-1,2,3,4-tetrahydroisoquinoline-3-carboxylic acid) as disclosed by Yamada et al., Bioorg. & Med. Chem. Leu., 8:1537-1540 (1998), 2-cyanopyrrolidides and 4-cyanopyrrolidides, as disclosed by Ashworth et al., Bioorg. & Med. Chem. Lett., 6(22):1163-1166 and 2745-2748 (1996), employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1(1-36) amide, GLP-1(7-36) amide, GLP-1(7-37) (as disclosed in U.S. Pat. No. 5,614,492 to Habener), as well as AC2993 (Amylin), and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., torcetrapib (Pfizer)), and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983, and 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440; and related statin compounds disclosed in U.S. Pat. No. 5,753,675; pyrazole analogs of mevalonolactone derivatives, as disclosed in U.S. Pat. No. 4,613,610; indene analogs of mevalonolactone derivatives, as disclosed in PCT application WO 86/03488; 642-(substituted-pyrrol-1-yl)alkyl)pyran-2-ones and derivatives thereof, as disclosed in U.S. Pat. No. 4,647,576; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-disubstituted pyrrole, furan and thiophene derivatives, as disclosed in European Patent Application No. 0221025; naphthyl analogs of mevalonolactone, as disclosed in U.S. Pat. No. 4,686,237; octahydronaphthalenes, such as disclosed in U.S. Pat. No. 4,499,289; keto analogs of mevinolin (lovastatin), as disclosed in European Patent Application No. 0142146 A2; and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin, and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 31(10):1869-1871 (1988), including isoprenoid (phosphinyl-methyl)phosphonates, as well as other known squalene synthetase inhibitors, for example, as disclosed in U.S. Pat. Nos. 4,871,721 and 4,924,024 and in Biller, S. A. et al., Current Pharmaceutical Design, 2:1-40 (1996).

In addition, other squalene synthetase inhibitors suitable for use herein include the terpenoid pyrophosphates disclosed by Ortiz de Montellano, P. et al., J. Med. Chem., 20:243-249 (1977), the farnesyl diphosphate analog A and presqualene pyrophosphate (PSQ-PP) analogs as disclosed by Corey et al., J. Am. Chem. Soc., 98:1291-1293 (1976), phosphinylphosphonates reported by McClard, R. W. et al., J. Am. Chem. Soc., 109:5544 (1987) and cyclopropanes reported by Capson, T. L., Ph.D. dissertation, June, 1987, Dept. Med. Chem. U of Utah, Abstract, Table of Contents, pp. 16, 17, 40-43, 48-51, Summary.

The fabric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future, 24:9-15 (1999) (Avasimibe); Nicolosi et al., "The ACAT inhibitor, C1-1011 is effective in the prevention and regression of aortic fatty streak area in hamsters", Atherosclerosis (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", *Chemtracts: Org. Chem.*, 8(6):359-362 (1995), or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the compounds of the invention include SCH48461 (Schering-Plough), as well as those disclosed in *Atherosclerosis*, 115:45-63 (1995) and J. Med. Chem., 41:973 (1998).

Examples of suitable ileal $Na^+$/bile acid cotransporter inhibitors for use in combination with the compounds of the invention include compounds as disclosed in *Drugs of the Future*, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, and those discussed in Hertzog, D. L., *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson), or axokine (Regeneron), with sibutramine and topiramate being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators; and monoclonal antibodies. Additional anti-cancer agents are disclosed in EP 1177791. The compounds of the invention may also be used in conjunction with radiation therapy.

Examples of suitable memory enhancing agents, anti-dementia agents, or cognitive agents for use in combination with the compounds of the present invention include, but are not limited to, donepezil, rivastigmine, galantamine, memantine, tacrine, metrifonate, muscarine, xanomelline, deprenyl, and physostigmine.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

FORMULATIONS AND DOSING

The compounds of formula I can be administered for any of the uses described herein by any suitable means, for example, orally, such as in the form of tablets, capsules, granules, or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules, or powders. The dose for adults is between 0.2 and 2,000 mg per day, preferably 0.25 to 250 mg per day, which can be administered in a single dose or in the form of individual doses from 1-4 times per day.

A typical capsule for oral administration contains compounds of structure I (25 mg), lactose (75 mg), and magnesium stearate (15 mg). The mixture is passed through a 60 mesh sieve and packed into a No. 1 gelatin capsule.

A typical injectable preparation is produced by aseptically placing 25 mg of compounds of structure I into a vial, aseptically freeze-drying and sealing. For use, the contents of the vial are mixed with 2 mL of physiological saline, to produce an injectable preparation.

ABBREVIATIONS

The following abbreviations are employed in the Examples and elsewhere herein:
Ph=phenyl
Bn=benzyl
t-Bu=tertiary butyl
i-Bu=iso-butyl
Me=methyl
Et=ethyl
Pr=propyl
iPr=isopropyl
Bu=butyl
AIBN=2,2'-Azobisisobutyronitrile
TMS=trimethylsilyl
$TMSCHN_2$=(trimethylsilyl)diazomethane
$TMSN_3$=trimethylsilyl azide
TBS=tert-butyldimethylsilyl
FMOC=fluorenylmethoxycarbonyl
Boc or BOC=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
DCM=dichloromethane
i-PrOH=isopropanol
DMSO=dimethyl sulfoxide
DME=1,2 dimethoxyethane
DMA=N,N-dimethylacetylamide
DCE=1,2 dichloroethane
HMPA=hexamethyl phosphoric triamide
HOAc or AcOH=acetic acid
TFA=trifluoroacetic acid
DIEA or DIPEA or i-$Pr_2$NEt or Hunig's Base=diisopropylethylamine
TEA or $Et_3N$=triethylamine
NMM=N-methyl morpholine
NBS=N-bromosuccinimide
NCS=N-chlorosuccinimide
DMAP=4-dimethylaminopyridine
DEPBT=3-diethoxyphosphoryloxy-1,2,3-benzotriazin-4 [3H]-one
mCPBA=3-chloroperoxybenzoic acid
$NaBH_4$=sodium borohydride
$NaBH(OAc)_3$=sodium triacetoxyborohydride
$NaN_3$=sodium azide
DIBALH=diisobutyl aluminum hydride
$LiAlH_4$=lithium aluminum hydride
n-BuLi=n-butyllithium
Oxone®=monopersulfate
Pd/C=palladium on carbon
$PXPd_2$=Dichloro(chlorodi-tert-butylphosphine)palladium (II) dimer or $[PdCl_2(t-Bu)_2PCl]_2$
$PtO_2$=platinum oxide
KOH=potassium hydroxide
NaOH=sodium hydroxide
LiOH=lithium hydroxide
$LiOH.H_2O$=lithium hydroxide monohydrate
HCl=hydrochloric acid
$H_2SO_4$=sulfuric acid
$H_2O_2$=hydrogen peroxide
$Al_2O_3$=aluminum oxide
$K_2CO_3$=potassium carbonate
$Cs_2CO_3$=cesium carbonate
$NaHCO_3$=sodium bicarbonate
$ZnBr_2$=zinc bromide
$MgSO_4$=magnesium sulfate
$Na_2SO_4$=sodium sulfate
KSCN=potassium thiocyanate
$NH_4Cl$=Ammonium chloride DBU=1,8-diazabicyclo[5.4.0]undec-7-ene EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)

HOBT or HOBT.H$_2$O=1-hydroxybenzotriazole hydrate

HOAT=1-Hydroxy-7-azabenzotriazole

PyBOP reagent or BOP reagent=benzotriazol-1-yloxy-tris(dimethylamino) phosphonium hexafluorophosphate NaN(TMS)$_2$=sodium hexamethyldisilazide or sodium bis(t-rimethylsilyl)amide Ph$_3$P=triphenylphosphine Pd(OAc)$_2$=Palladium acetate (Ph$_3$P)$_4$Pd°=tetrakis triphenylphosphine palladium Pd$_2$(dba)$_3$=tris(dibenzylacetone)dipalladium DPPF=1,1'-Bis(diphenylphosphino)ferrocene HATU=2-(7-aza-1H-benzotriazole-1-yl)-1,1,3,3-tetramethyluronium hexafluorophosphate, 2-(3H-[1,2,3]triazolo[4,5-b]pyridin-3-yl)-1,1,3,3-tetramethylisouronium hexafluorophosphate(V)

DEAD=diethyl azodicarboxylate

DIAD=diisopropyl azodicarboxylate

Cbz-Cl=benzyl chloroformate

CAN=ceric ammonium nitrate

SAX=Strong Anion Exchanger

SCX=Strong Cation Exchanger

H$_2$=hydrogen

Ar=argon

N$_2$=nitrogen

Equiv=equivalent(s)

min=minute(s)

h or hr=hour(s)

L=liter mL=milliliter

μL=microliter g=gram(s)

mg=milligram(s)

mol=moles mmol=millimole(s)

meq=milliequivalent

RT or R.T.=room temperature

AT=ambient temperature sat or sat' d=saturated aq.=aqueous

TLC=thin layer chromatography

HPLC=high performance liquid chromatography

HPLC R$_t$=HPLC retention time

LC/MS=high performance liquid chromatography/mass spectrometry

MS or Mass Spec=mass spectrometry

NMR=nuclear magnetic resonance

NMR spectral data: s=singlet; d=doublet; m=multiplet; br=broad; t=triplet mp=melting point

EXAMPLES

The following Examples are illustrative of preferred compounds of the invention.

Example 1

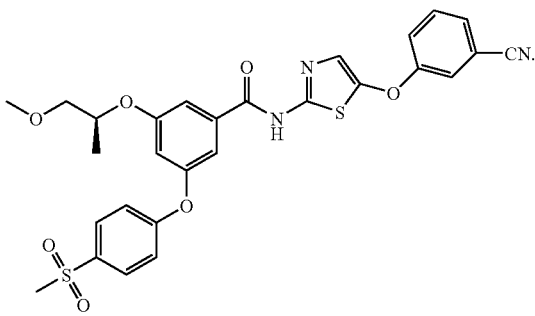

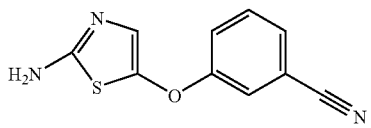

To a solution of 3-hydroxybenzonitrile (137 mg, 1.15 mmol) in acetone (3 mL), was added 5-bromothiazol-2-amine hydrobromide (300 mg, 1.15 mmol) and Cs$_2$CO$_3$ (749 mg, 2.30 mmol). The reaction mixture was stirred at 55° C. for 12 h, then was cooled to RT. The mixture was filtered and washed with acetone. The combined filtrates were concentrated in vacuo, then partitioned between EtOAc and H$_2$O. The organic phase was washed with brine, dried (MgSO$_4$), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90:10:0.1 H$_2$O:MeOH:TFA and B=90:10:0.1 MeOH:H$_2$O:TFA) to provide part A compound (70 mg, 28% yield) as a solid.

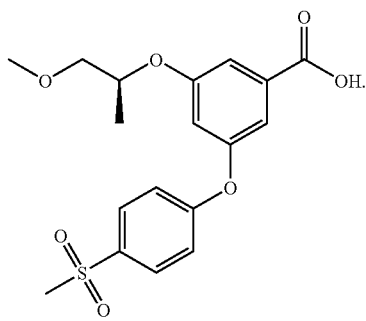

3-{(1S)-2-methoxy-(1-methylethyl)oxy}-5-{[4-(methylsulfonyl)phenyl]oxy}benzoic acid was prepared following the procedure set forth in WO 2005/121110.

C

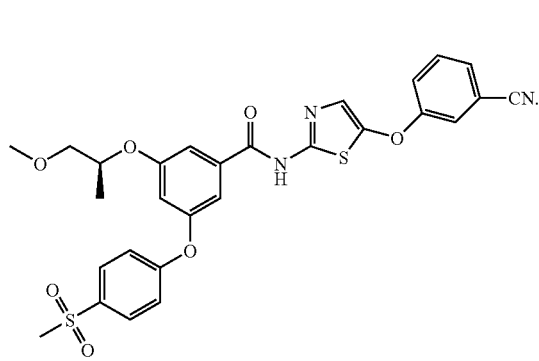

To a solution of Part B acid (250 mg, 0.66 mmol) in CH$_2$Cl$_2$ (4 mL) was added oxalyl chloride (723 μL, 1.45 mmol, 2M in CH$_2$Cl$_2$) and DMF (10 drops). The resulting mixture was stirred at RT for 1 h and then was concentrated in vacuo. The residue was dissolved in THF (2 mL), and was slowly added to a solution of Part A compound (313 mg, 1.45 mmol) and NaHCO$_3$ (166 mg, 1.97 mmol) in THF:H$_2$O (1:1, 4 mL). The reaction mixture was stirred at RT for 3 h, then was partitioned between EtOAc and H$_2$O. The organic phase was washed with brine, dried (MgSO$_4$), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (240 mg, 63% yield) as a white solid. [M+H]$^+$=580.2, $^1$H NMR (400 MHz, DMSO-d$_6$): δ 7.95 (d, J=9.23 Hz, 2 H), 7.66-7.70 (m, 1 H), 7.57-7.66 (m, 2 H), 7.54-7.58 (m, 1 H), 7.48-7.54 (m, 1 H), 7.43 (s, 1H), 7.32-7.38 (m, 1H), 7.26 (d, J=8.79 Hz, 2H), 7.02 (t, J=2.20 Hz, 1H), 4.72-4.85 (m, 1H), 3.43-3.57 (m, 2H), 3.29 (s, 3 H), 3.22 (s, 3 H), 1.25 (d, J=6.15 Hz, 3H).

Example 2

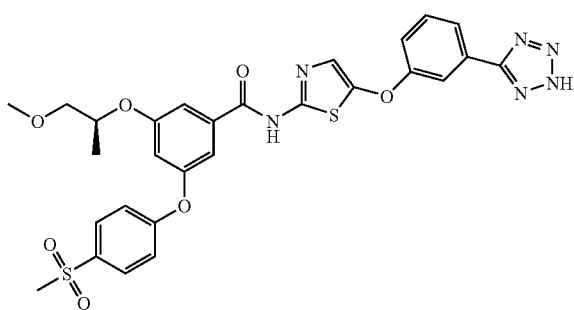

To a solution of Example 1 Part C compound (53 mg, 0.092 mmol) in water (3 mL) was added NaN$_3$ (18 mg, 0.28 mmol) and ZnBr$_2$ (62 mg, 0.28 mmol). The reaction was refluxed at 100° C. with stirring for 46 h, then was cooled to RT. 1N aqueous HCl (2 mL) and EtOAc (5 mL) were added; the aqueous layer was adjusted to pH 1. After vigorous stirring for 30 min, the aqueous layer was washed with EtOAc (6 mL). The combined organic extracts were concentrated in vacuo, and the residue was purified by preparative HPLC (Phenomenex Luna AXIA 5u C18 30×100 mm column; detection at 220 nm; flow rate=40 mL/min; continuous gradient from 40% B to 100% B over 10 min+2 min hold time at 100% B, where A=90:10:0.1 H$_2$O:MeOH:TFA and B=90:10:0.1 MeOH:H$_2$O:TFA) to provide the title compound (24 mg, 42% yield) as a white solid. [M+H]$^+$=623.4, $^1$H NMR (400 MHz, DMSO-d$_6$) δ 7.94 (d, J=8.79 Hz, 2 H), 7.83 (d, J=7.91 Hz, 1 H), 7.75 (t, J=2.64 Hz, 1 H), 7.64 (t, J=8.13 Hz, 1 H), 7.56 (s, 1 H), 7.44 (s, 1 H), 7.39 (dd, J=8.35, 2.20 Hz, 1 H), 7.36 (s, 1 H), 7.25 (d, J=8.79 Hz, 2 H), 6.97-7.05 (m, 1 H), 4.71-4.85 (m, 1 H), 3.44-3.55 (m, 2 H), 3.28 (s, 3 H), 3.21 (s, 3 H), 1.24 (d, J=6.15 Hz, 2 H).

Example 3

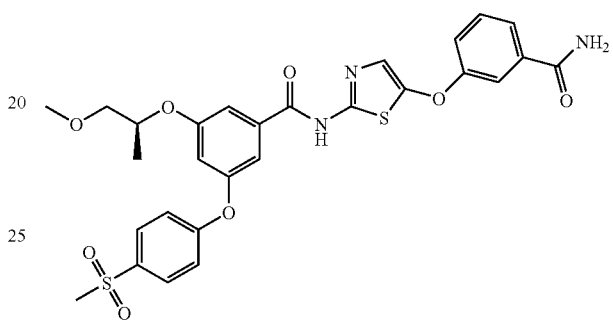

To a solution of Example 1 Part C compound (65 mg, 0.11 mmol) in THF (2 mL) was added 1N aqueous NaOH (1 mL). The reaction was heated at 70° C. with stirring for 94 h. The reaction was then cooled to RT, was diluted with EtOAc, and was neutralized with 1N aqueous HCl. The organic layer was washed with H$_2$O and brine, was dried (MgSO$_4$), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1H$_2$O:MeOH:TFA and B=90:10:0.1 MeOH:H$_2$O:TFA) to provide the title compound (13 mg, 19% yield) as a white solid. [M+H]$^+$=598.2, $^1$H NMR (400 MHz, CD$_3$OD) δ 7.96 (d, J=9.23 Hz, 2 H), 7.60-7.68 (m, 2 H), 7.43-7.51 (m, 2 H), 7.27-7.34 (m, 2 H), 7.22 (d, J=8.79 Hz, 2 H), 7.19 (s, 1 H), 6.96 (t, J=2.20 Hz, 1 H), 4.64-4.77 (m, 1 H), 3.48-3.63 (m, 2 H), 3.38 (s, 3 H), 3.12 (s, 3 H), 1.31 (d, J=6.15 Hz, 3 H).

Example 4

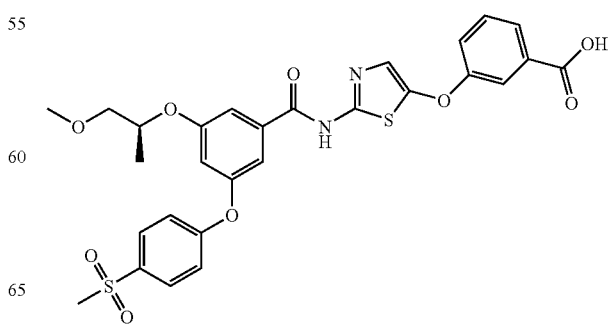

-continued

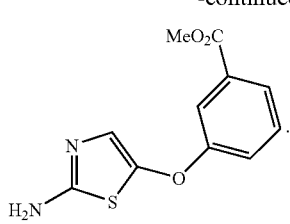

To a RT solution of 5-bromothiazol-2-amine hydrobromide (1.4 g, 5.3 mmol) in acetone (26 mL) was added methyl 3-hydroxybenzoate (888 mg, 5.8 mmol) and Cs$_2$CO$_3$ (3.8 g, 11.7 mmol). The reaction mixture was stirred at 55° C. for 5 h, then was cooled to RT, and was stirred for an additional 10 h at RT. The mixture was filtered and washed with acetone. The combined filtrates were concentrated in vacuo, and the residue was partitioned between EtOAc and H$_2$O. The organic phase was dried (MgSO$_4$), filtered, and concentrated in vacuo. The residue was partitioned between EtOAC and 1N aqueous NaOH; the organic phase was washed with brine, dried (MgSO$_4$), filtered, and concentrated in vacuo to provide the crude Part A compound as an oil (445 mg, 34%).

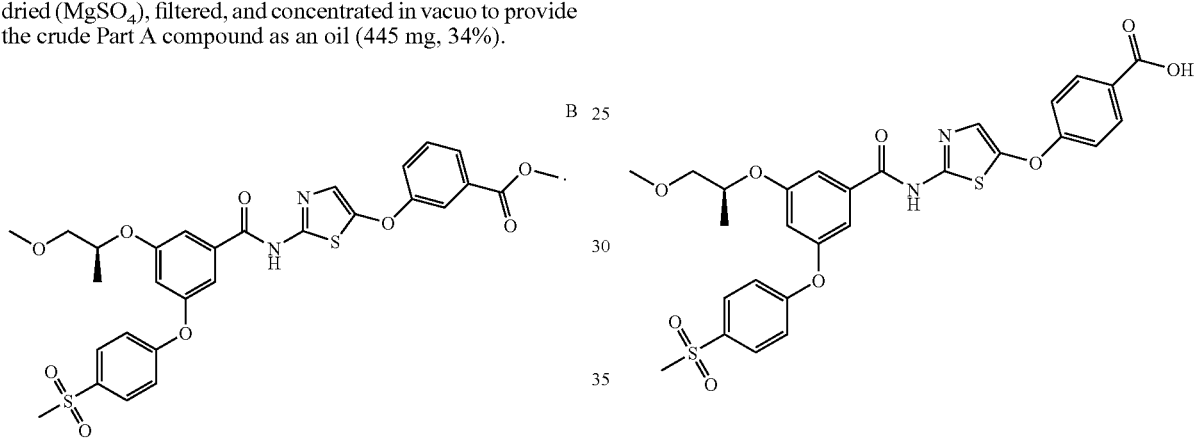

To a solution of Part B compound (51 mg, 0.13 mmol) in CH$_2$Cl$_2$ (1.5 mL) was added oxalyl chloride (147 µL, 0.30 mmol, 2M in CH$_2$Cl$_2$) and DMF (4 drops).

The resulting mixture was stirred at RT for 1 h and then was concentrated in vacuo. The residue was dissolved in THF (1 mL), then was slowly added to a solution of the Part A compound (50 mg, 0.20 mmol) and NaHCO$_3$ (34 mg, 0.40 mmol) in THF:H$_2$O (1:1, 2 mL). The reaction mixture was stirred at RT for 2 h, then was partitioned between EtOAc and H$_2$O. The organic phase was washed with brine, dried (MgSO$_4$), filtered, and concentrated in vacuo. The residue was used in the next step without further purification.

To a solution of crude Part B compound (0.13 mmol) in THF:H$_2$O (2:1, 1.5 mL) was added LiOH.H$_2$O (28.1 mg, 0.67 mmol). The reaction was stirred at RT for 40 h, then was diluted with EtOAc, acidified with 1N aqueous HCl to pH 1-2, was washed with H$_2$O and brine, was dried (MgSO$_4$), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O: MeOH:TFA and B=90:10:0.1 MeOH:H$_2$O:TFA) to provide the title compound (15 mg, 19% yield over two steps) as a white solid. [M+H]$^+$=599.2, $^1$H NMR (400 MHz, DMSO-d$_6$) δ 7.94 (d, J=8.79 Hz, 2 H), 7.72 (d, J=7.91 Hz, 1 H), 7.54-7.59 (m, 2 H), 7.51-7.54 (m, 1 H), 7.43 (dd, J=7.47, 2.64 Hz, 1 H), 7.41 (s, 1 H), 7.33-7.37 (m, 1 H), 7.25 (d, J=8.79 Hz, 2 H), 7.00 (t, J=2.20 Hz, 1 H), 4.72-4.85 (m, 1 H), 3.42-3.57 (m, 2 H), 3.28 (s, 3 H), 3.20 (s, 3 H), 1.24 (d, J=6.15 Hz, 3 H).

Example 5

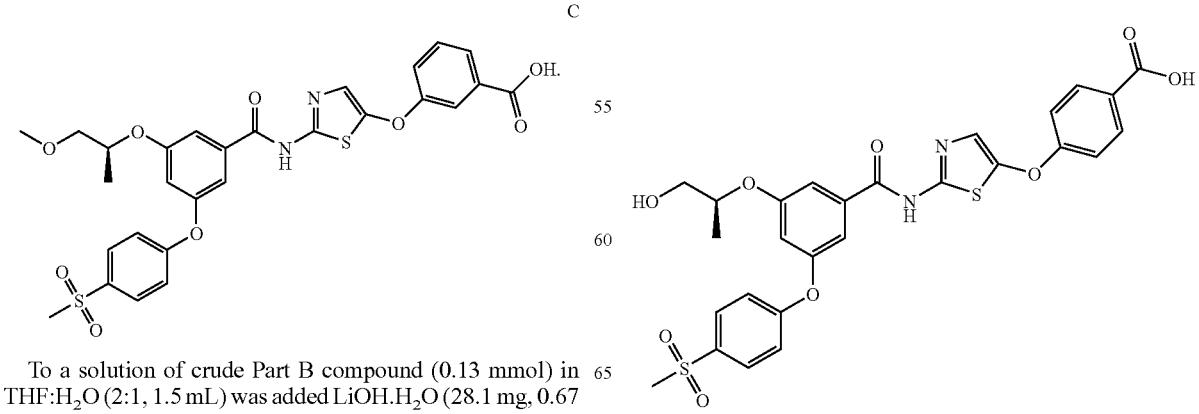

The title compound was prepared from methyl 4-hydroxybenzoate following the same general procedure used to prepare Example 4 to give the title compound (13 mg, 16% yield) as a white solid. [M+H]$^+$=599.2, $^1$H NMR (400 MHz, DMSO-d$_6$) δ ppm 7.89-8.00 (m, 4 H), 7.51-7.60 (m, 1 H), 7.43 (s, 1 H), 7.32-7.38 (m, 1 H), 7.25 (d, J=9.23 Hz, 2 H), 7.21 (d, J=8.79 Hz, 2 H), 7.01 (t, J=2.20 Hz, 1 H), 4.71-4.86 (m, 1 H), 3.47-3.55 (m, 2 H), 3.28 (s, 3 H), 3.21 (s, 3 H), 1.24 (d, J=6.15 Hz, 3 H).

Example 6

A

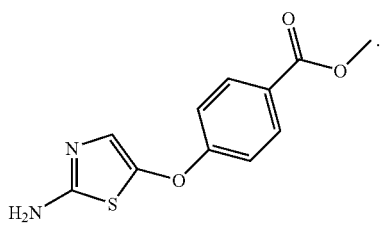

To a solution of 5-bromothiazol-2-amine hydrobromide (300 mg, 1.15 mmol) in acetone (3 mL), was added methyl 4-hydroxybenzoate (175 mg, 1.15 mmol) and $Cs_2CO_3$ (749 mg, 2.30 mmol). The reaction mixture was stirred at 55° C. for 12 h, then was cooled to RT. The mixture was filtered and washed with acetone. The combined filtrates were concentrated in vacuo, then partitioned between EtOAc and $H_2O$. The organic phase was washed with brine, dried ($MgSO_4$), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90:10:0.1 $H_2O$:MeOH:TFA and B=90:10:0.1 MeOH:$H_2O$:TFA) to provide part A compound (62 mg, 22% yield) as a solid.

B

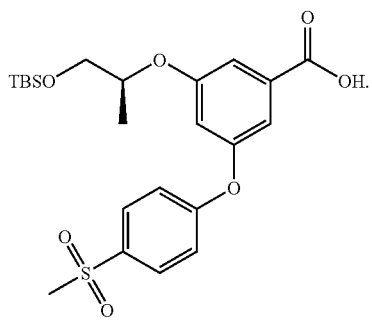

i

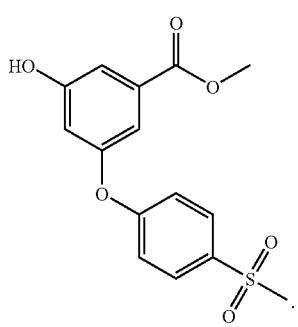

Methyl 3-hydroxy-5-(4-(methylsulfonyl)phenoxy)benzoate (10 g, 50% yield, white solid) was prepared following the procedure set forth in WO 2005/121110.

ii

To a 0° C. solution of Part B(i) compound (3.7 g, 0.012 mol), (R)-(−)-1-benzyloxy-2-propanol (2.5 g, 0.015 mol), and $Ph_3P$ resin (30 g, 0.031 mol) in THF (150 mL) was added DIAD (3.5 g, 0.017 mol) dropwise over 15 min. The reaction mixture was stirred at 0° C. for 30 min, then was allowed to warm to RT, and was stirred for 3 h at RT. The reaction was filtered, and the filtrate was concentrated in vacuo. The residue was diluted with EtOAc/hexane (1:1, 10 mL), the solid was filtered off, and the filtrate was concentrated in vacuo. The residue was once again diluted with EtOAc/Hexane (1:1, 10 mL), the solid was filtered off, and the filtrate was concentrated in vacuo. The residue was chromatographed ($SiO_2$; EtOAc/Hex, 1:2) to afford the Part B(ii) compound as a colorless oil (6.0 g).

iii

A solution of the Part B(ii) compound (6.0 g, 0.013 mol) and LiOH.$H_2O$ (1.6 g, 0.065 mol) in MeOH/THF/$H_2O$ (3/3/5, 110 mL) was stirred at RT for 3 h. The reaction was concentrated in vacuo, and the residue was washed with $H_2O$, was adjusted to pH 4 with concentrated HCl, and was then extracted with EtOAc. The organic layer was washed with $H_2O$, was dried ($Na_2SO_4$), filtered, and concentrated in vacuo to give the Part B(iii) compound as a white solid (5.0 g).

iv

To a solution of the Part B(iii) compound (1.0 g, 2.3 mmol) in EtOAc (5 mL) was added 10% Pd/C (100 mg). A H$_2$ (g) atmosphere was introduced using a balloon, and the reaction was stirred at RT for 72 h. The reaction mixture was filtered, and the catalyst was washed with MeOH. The filtrate was concentrated in vacuo to give the Part B(iv) compound as a colorless oil (0.82 g).

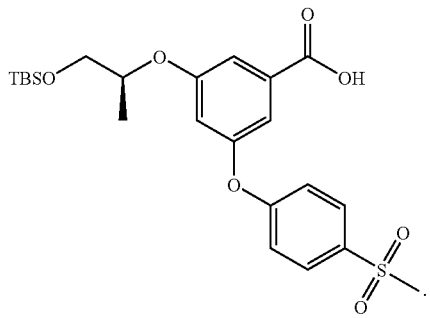

To a solution of tert-butyldimethylsilyl chloride (1.0 g, 6.7 mmol) and Part B(iv) compound (0.82 g, 2.2 mmol) in DMF (6 mL) was added imidazole (0.91 g, 13.4 mmol). The reaction was stirred at RT for 1 h, then was stored in the freezer overnight. The next day, the reaction was warmed to RT and was partitioned between EtOAc and saturated aqueous NH$_4$Cl. The organic phase was isolated, washed with saturated aqueous NH$_4$Cl and brine, dried (MgSO$_4$), filtered, and concentrated in vacuo. The residue was chromatographed (SiO$_2$; EtOAc:Hexane, from 0% to 100% over 14 min) to give Part B(v) compound (725 mg, 68% yield) as a white foam.

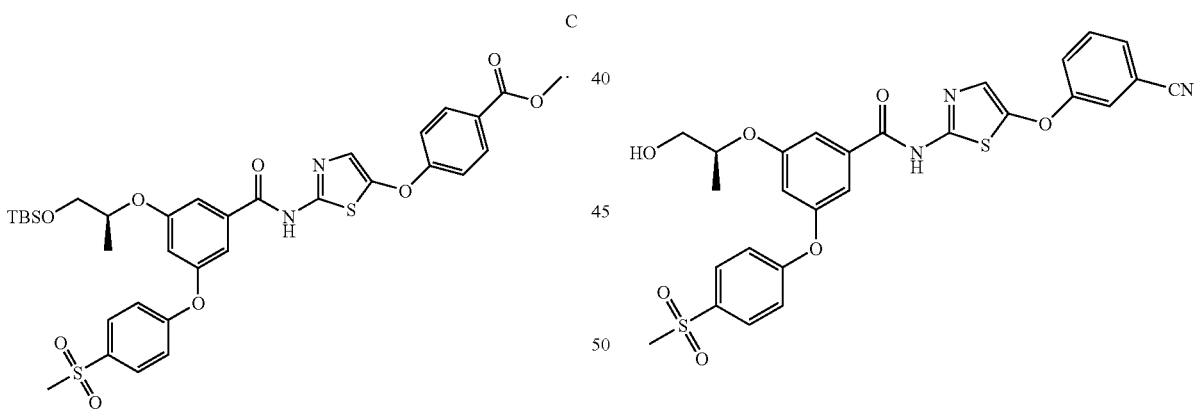

To a solution of Part A compound (60 mg, 0.24 mmol), HOBT (43 mg, 0.31 mmol), and Et$_3$N (0.05 mL, 0.36 mmol) in CH$_2$Cl$_2$ (6 mL) was added Part B(v) compound (116 mg, 0.24 mmol). The reaction mixture stirred at RT for 10 min, and EDC (60 mg, 0.31 mmol) was added. The reaction was stirred at RT for 12 h, then was concentrated in vacuo, and the residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide Part C compound (10 mg, 6% yield) as an orange solid.

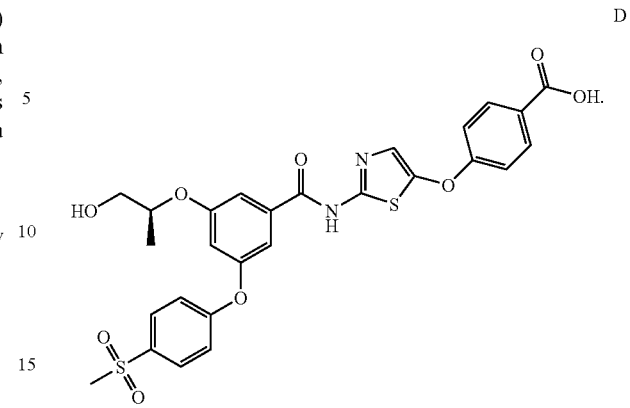

To a solution of Part C compound (10 mg, 0.02 mmol) in THF:H$_2$O (2:1, 3 mL) was added LiOH (2 mg, 0.08 mmol). The reaction was stirred at RT for 12 h. The reaction mixture was diluted with EtOAc and acidified to pH 2 with 1N aqueous HCl. The mixture was washed with H$_2$O and brine. The organic layer was dried (MgSO$_4$), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (4 mg, 41% yield) as a white solid. [M+H]$^+$=585.2, $^1$H NMR (400 MHz, CD$_3$OD) δ 8.05-6.98 (m, 12 H), 3.72 (m, 2 H), 3.70 (m, 1 H), 3.29 (s, 3 H), 1.31 (m, 3 H).

Example 7

To a −10° C. solution of Example 6 Part B(v) compound (200 mg, 0.42 mmol) in CH$_2$Cl$_2$ (5 mL) was added pyridine (0.04 mL, 0.5 mmol) and cyanuric fluoride (0.11 mL, 1.25 mmol). The reaction was stirred at −10° C. for 30 min, then was warmed to RT and was stirred for 90 min. The reaction mixture was poured onto ice water and was extracted with CH$_2$Cl$_2$. The organic layer was dried (MgSO$_4$), filtered, and concentrated in vacuo. The acid fluoride residue was taken up in THF (3 mL) and was added to a mixture of Example 1 Part A compound (99 mg, 0.46 mmol) and pyridine (0.14 mL, 1.67 mmol) in THF (6 mL). The reaction was stirred at RT for 72 h, then was concentrated in vacuo, and the residue was purified by Preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA). The TBS group was cleaved during concentration of the TFA-containing fractions, so the alcohol residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA) to provide the title compound (2.7 mg, 1% yield) as a white solid. [M+H]⁺=566.1, ¹H NMR (400 MHz, CD₃OD) δ 7.97-6.98 (m, 12 H), 3.68 (m, 2 H), 3.49 (m, 1 H), 3.12 (s, 3 H), 1.30 (m, 3 H).

Example 8

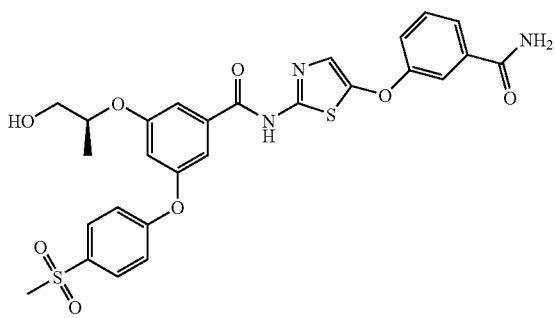

To a solution of Example 7 compound (58 mg, 0.10 mmol) in THF (3 mL) was added 1N aqueous NaOH (1 mL). The reaction was stirred at 70° C. for 48 h, then was cooled to RT and was stirred for 72 h. The reaction mixture was concentrated in vacuo, and the residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA) to provide the title compound (2 mg, 4% yield) as a white lyophilate. [M+H]⁺=585.1, ¹H NMR (400 MHz, CDCl₃) δ 8.03-6.98 (m, 12 H), 3.95 (m, 1 H), 3.79 (m, 2 H), 3.22 (s, 3 H), 1.18 (m, 3 H).

Example 9

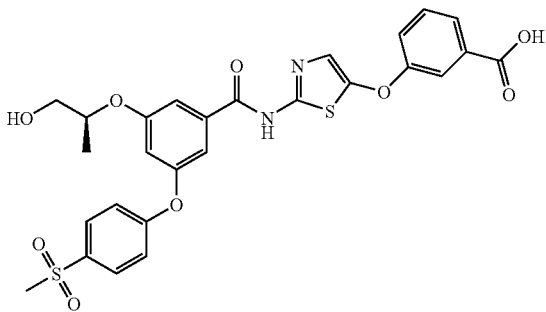

A

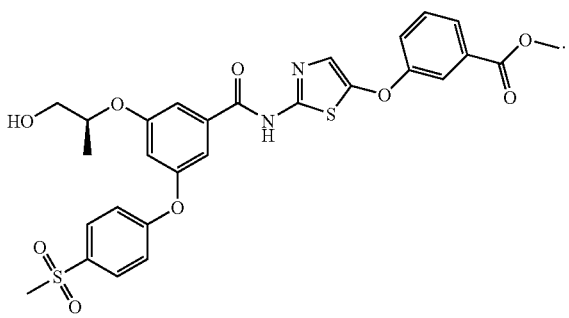

To a −10° C. solution of Example 6 Part B(v) compound (44 mg, 0.09 mmol) in CH₂Cl₂ (3 mL) was added pyridine (0.01 mL, 0.11 mmol) and cyanuric fluoride (0.03 mL, 0.28 mmol). The reaction was stirred at −10° C. for 30 min, then was warmed to RT and was stirred for 90 min. The reaction mixture was poured onto ice water and was extracted with CH₂Cl₂. The organic layer was dried (MgSO₄), filtered, and concentrated in vacuo. The acid fluoride residue was taken up in THF (1 mL) and was added to a mixture of Example 4 Part A compound (25 mg, 0.10 mmol) and pyridine (0.03 mL, 0.37 mmol) in THF (3 mL). The reaction was stirred at RT for 72 h, then was concentrated in vacuo. The residue was purified by Preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA). The TBS group was cleaved during concentration of the TFA-containing fractions, so the alcohol residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH:TFA and B=90:10:0.1 MeOH:H₂O:TFA) to provide Part A compound (25 mg, 50% yield) as a white solid.

B

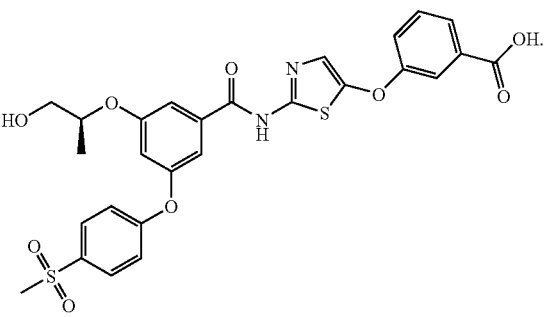

To a solution of the Part A compound (25 mg, 0.04 mmol) in THF:H₂O (2:1, 3 mL) was added LiOH.H₂O (5 mg, 0.21 mmol). The reaction was stirred at RT for 12 h. The reaction was diluted with EtOAc, was acidified to pH 2 with 1N aqueous HCl, and was washed with H₂O and brine. The organic layer was dried (MgSO₄), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (3.9 mg, 16% yield) as a white lyophilate. [M+H]$^+$=585.2, $^1$H NMR (400 MHz, CD$_3$OD) δ 8.01 (m, 2 H), 7.81 (m, 1 H), 7.72 (s, 1 H), 7.45 (m, 2 H), 7.33 (m, 2 H), 7.24 (m, 3 H), 7.03 (s, 1H), 4.62 (broad s, OH), 3.72 (m, 2H), 3.21 (s, 3H), 2.98 (s, 1H), 1.31 (m, 3H).

Example 10

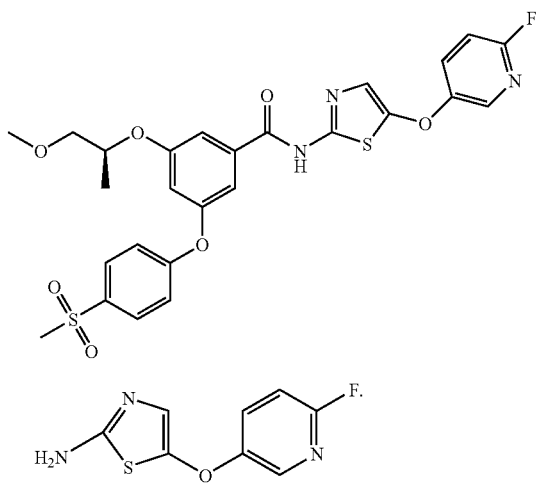

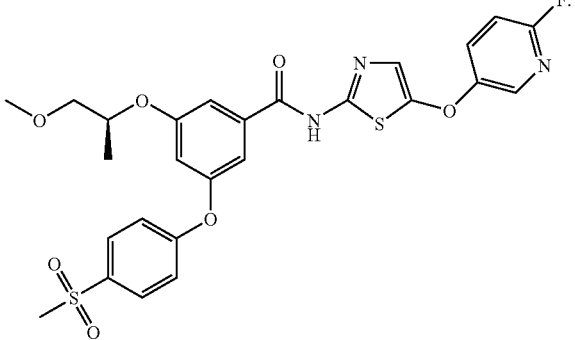

A

To a solution of 6-fluoropyridin-3-ol (43.5 mg, 0.385 mmol) and 5-bromothiazol-2-amine hydrobromide (100 mg, 0.385 mmol) in acetone (5 mL) was added Cs$_2$CO$_3$ (276 mg, 0.846 mmol). The reaction was stirred at 55° C. for 16 h, then was cooled to RT. The mixture was filtered and washed with acetone. The combined filtrates were concentrated in vacuo, then were partitioned between EtOAc and water. The organic layer was washed with brine, dried (MgSO$_4$), filtered, and concentrated in vacuo. The residue was purified by preparative HPLC (Phenomenex Luna AXIA 5u C18 30×100 mm column; detection at 220 nm; flow rate=40 mL/min; continuous gradient from 10% B to 100% B over 10 min+2 min hold time at 100% B, where A=90:10:0.1 H$_2$O:MeOH:TFA and B=90:10:0.1 MeOH:H$_2$O:TFA) to give the Part A compound (45 mg, 55% yield) as a white solid.

B

To a mixture of the Example 1 Part B compound (75 mg, 0.197 mmol), Part A compound (54.1 mg, 0.256 mmol), and HOAT (33.5 mg, 0.246 mmol) in DMF (2 mL) was added Hunig's Base (0.045 mL, 0.256 mmol) and EDC (47.2 mg, 0.246 mmol). The reaction was stirred at RT for 16 h, then was partitioned between EtOAc and water. The organic layer was washed with brine, dried (MgSO$_4$), filtered, and concentrated in vacuo. The residue was purified by preparative HPLC (Phenomenex Luna AXIA 5 μm C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to provide the title compound (25 mg, 22% yield) as a yellow foam solid. [M+H]$^+$=574.2, $^1$H NMR (400 MHz, DMSO-d$_6$) δ 8.16 (s, 1 H), 7.95 (m, 2H), 7.85 (m, 1 H), 7.55 (s, 1 H), 7.39 (m, 2 H), 7.25 (m, 3 H), 7.01 (s, 1H), 4.78 (m, 1H), 3.48 (m, 2H), 3.28 (s, 3H), 3.20 (s, 3H), 1.23 (s, 3H).

Example 11

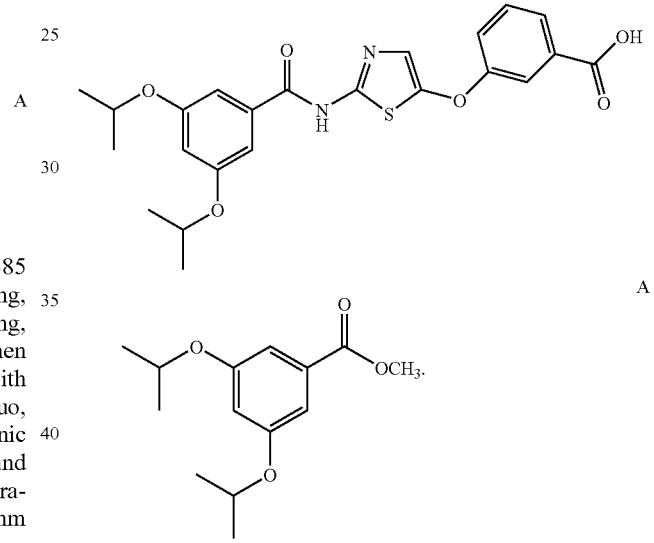

A

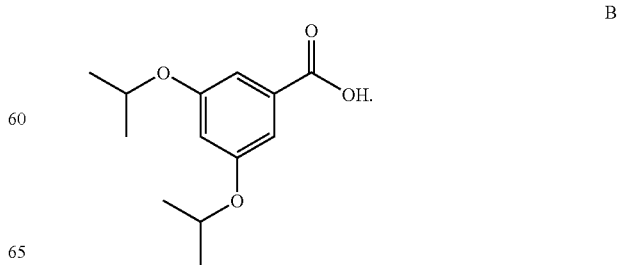

B

To a solution of methyl 3,5-dihydroxy benzoate (1.5 g, 8.9 mmol) in MeCN (20 mL) was added isopropyl bromide (4.2 mL, 44.6 mmol) and Cs$_2$CO$_3$ (8.7 g, 26.7 mmol). The reaction was stirred at reflux (85° C.) for 12 h and was then cooled to RT. The reaction was quenched with H$_2$O and extracted with EtOAc (3×). The organic layer was washed with H$_2$O and brine, dried (MgSO$_4$), filtered, and concentrated in vacuo to give Part A compound (2.0 g, 93% yield) as a yellow oil.

To a solution of the Part A compound (2.0 g, 7.9 mmol) in THF:H₂O (5:1, 60 mL) was added LiOH.H₂O (732 mg, 17.4 mmol). The reaction was stirred at 45° C. for 12 h, then was cooled to RT. The volatiles were removed in vacuo, and the water layer was extracted with Et₂O. The aqueous layer was then acidified with 1N aqueous HCl until a cloudy precipitate was formed. The aqueous layer was then extracted with EtOAc. The combined organic layers were dried (MgSO₄), filtered, and concentrated in vacuo to give Part B compound (1.8 g, 100% yield) as an off-white solid.

C

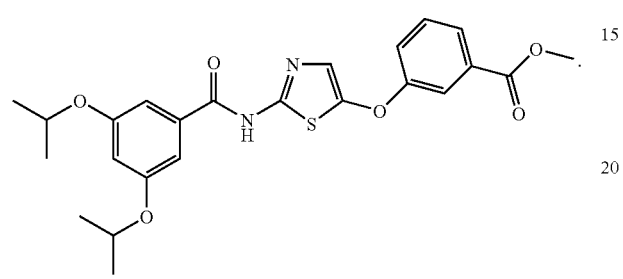

To a solution of Part B compound (50 mg, 0.21 mmol), Example 4 Part A compound (75 mg, 0.30 mmol), and HOAT (36 mg, 0.26 mmol) in DMF (0.5 mL) was added iPr₂NEt (0.05 mL, 0.27 mmol), followed by addition of EDC.HCl (50 mg, 0.26 mmol). The reaction was stirred at RT for 72 h, then was partitioned between EtOAc and H₂O. The organic layer was washed with brine, was dried (MgSO₄), filtered, and concentrated in vacuo to give crude Part C compound as an orange/brown oil.

D

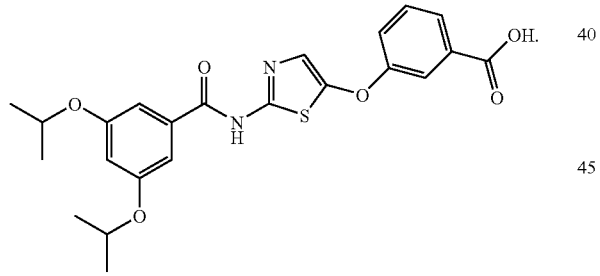

To a solution of Part C compound in THF:H₂O (2:1, 3 mL) was added LiOH.H₂O (25 mg, 1.04 mmol). The reaction was stirred at RT for 12 h. An additional portion of LiOH.H₂O (25 mg, 1.04 mmol) was added, and the reaction was stirred at RT for 12 h. The reaction mixture was diluted with EtOAc, was acidified to pH 2 with 1N aqueous HCl, and was washed with H₂O and brine. The organic layer was dried (MgSO₄), filtered, and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H₂O:MeOH: TFA and B=90:10:0.1 MeOH:H₂O:TFA) to provide the title compound (7.5 mg, 8% yield) as an off-white solid. [M+H]⁺=457.1, ¹H NMR (400 MHz, DMSO-d₆) δ 7.73 (m, 1 H), 7.58 (m, 2 H), 7.42 (m, 1 H), 7.40 (s, 1 H), 7.19 (s, 2 H), 6.65 (m, 1 H), 4.70 (s, 2 H), 1.27 (m, 12 H).

Example 12

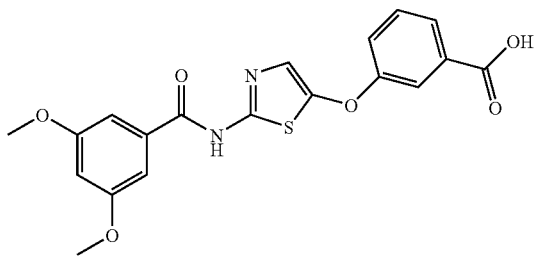

The title compound was prepared from 3,5-dimethoxy benzoic acid following the same general procedure used to prepare Example 11 to provide the title compound (3.0 mg, 3% yield) as an off-white solid. [M+H]⁺=401.0, ¹H NMR (400 MHz, DMSO-d₆) δ 7.75 (m, 1 H), 7.55 (m, 3 H), 7.45 (m, 1 H), 7.40 (s, 1 H), 7.25 (s, 2 H), 6.780 (m, 1 H), 3.81 (s, 6 H).

Example 13

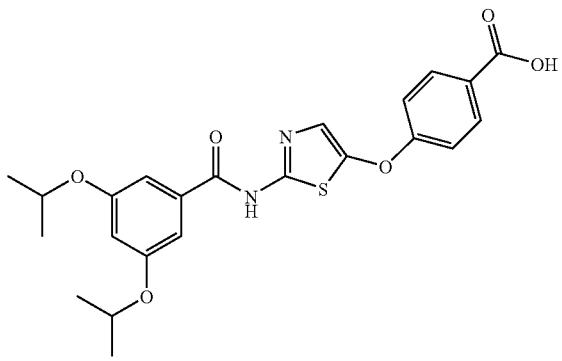

The title compound was prepared from Example 6 Part A compound following the same general procedure used to prepare Example 11 to provide the title compound (8.0 mg, 8% yield) as a white solid. [M+H]⁺=457.1, ¹H NMR (400 MHz, CDCl₃) δ 8.15-6.64 (m, 8 H), 4.44 (s, 2 H), 1.37 (m, 12 H).

Example 14

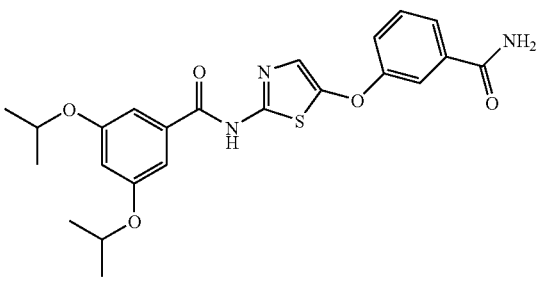

-continued

A

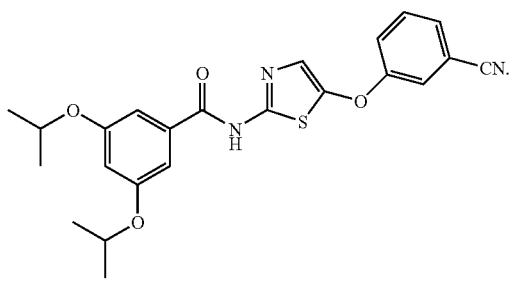

To a mixture of Example 11 Part B compound (100 mg, 0.42 mmol), Example 1 Part A compound (118 mg, 0.55 mmol), and HOAT (71 mg, 0.52 mmol) in DMF (1.0 mL) was added iPr$_2$NEt (0.10 mL, 0.55 mmol) followed by addition of EDC.HCl (101 mg, 0.52 mmol). The reaction was stirred at RT for 48 h. The reaction mixture was partitioned between EtOAc and H$_2$O. The organic phase was washed with brine, was dried (MgSO$_4$), filtered, and concentrated in vacuo to give crude Part A compound as a brown oil.

B

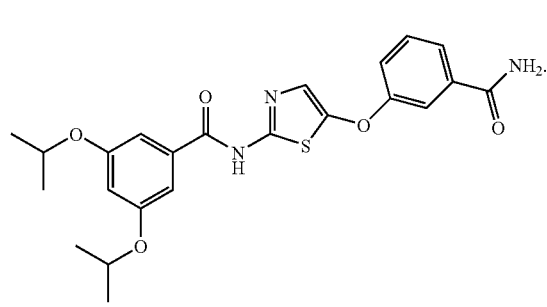

To a solution of Part A compound (91.5 mg, 0.21 mmol) in THF (3 mL) was added 1N aqueous NaOH (1 mL). The reaction was stirred at 70° C. for 12 h. Additional 1N aqueous NaOH (1 mL) was added and stirring was continued at 70° C. for 12 h. The reaction was cooled to RT and was stirred for 48 h. The reaction was concentrated in vacuo, and the residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (6 mg, 6% yield) as a white solid. [M+H]$^+$=456.1, $^1$H NMR (400 MHz, DMSO-d$_6$) δ 8.07 (broad, NH$_2$), 7.65 (m, 1 H), 7.59 (m, 1 H), 7.49 (m, 1 H), 7.37 (s, 1 H), 7.31 (m, 1 H), 7.18 (s, 1 H), 6.64 (m, 2 H), 4.69 (s, 2 H), 1.26 (m, 12 H).

Example 15

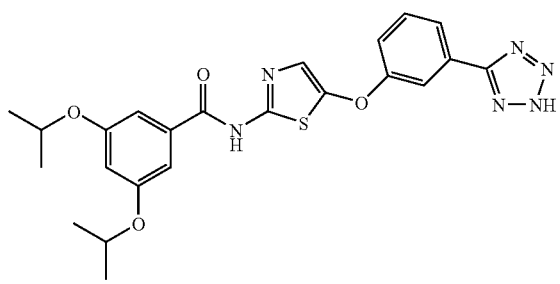

To a solution of Example 14 Part A compound (91.5 mg, 0.21 mmol) in H$_2$O (4 mL) was added NaN$_3$ (41 mg, 0.63 mmol) and ZnBr$_2$ (141 mg, 0.63 mmol). The reaction mixture was heated to reflux (105° C.) for 72 h. The reaction was cooled to RT and 1N aqueous HCl (3 mL) and EtOAc (6 mL) were added. The reaction was stirred vigorously for 30 min until the aqueous layer reached pH 1. The organic layer was isolated, and the aqueous layer was extracted with EtOAc. The combined organic layers were dried (MgSO$_4$), filtered, and concentrated in vacuo. The residue was purified by Preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (40 mg, 40% yield) as a pale orange solid. [M+H]$^+$=481.1, $^1$H NMR (400 MHz, DMSO-d$_6$) δ 7.88 (m, 1 H), 7.76 (m, 1 H), 7.64 (m, 1 H), 7.45 (s, 1 H), 7.40 (m, 1 H), 7.19 (s, 2 H), 6.64 (s, 1 H), 4.69 (s, 2 H), 1.26 (m, 12 H).

Example 16

A

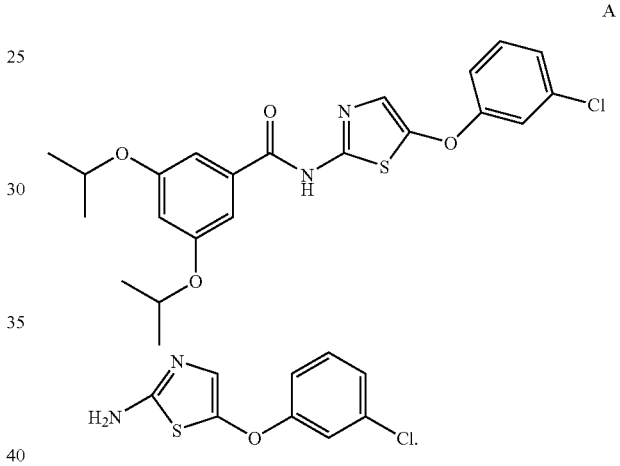

To a solution of 5-bromothiazol-2-amine hydrobromide (305 mg, 1.17 mmol) in acetone (7.8 mL), was added 3-chlorophenol (124 mL, 1.17 mmol) and Cs$_2$CO$_3$ (841 mg, 2.58 mmol). The reaction mixture was stirred at 55° C. for 68 h, then was cooled to RT. The mixture was filtered and washed with acetone. The combined filtrates were concentrated in vacuo, then the residue was partitioned between EtOAc and H$_2$O. The organic phase was washed with brine, dried (MgSO$_4$), filtered, and concentrated in vacuo to provide the crude Part A compound as a brown oil.

B

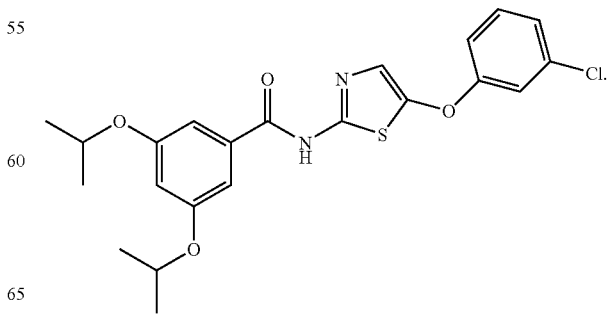

To a solution of Example 11 Part B compound (40 mg, 0.17 mmol) in CH$_2$Cl$_2$ (1.5 mL) was added oxalyl chloride (0.2 mL, 0.38 mmol) and DMF (4 drops). The reaction was stirred at RT for 1 h and was concentrated in vacuo. The residue was taken up in THF and was added to a solution of the Part A compound (excess) and NaHCO$_3$ (43 mg, 0.50 mmol) in THF:H$_2$O (1:1, 3 mL). The reaction was stirred at RT for 12 h, then was diluted with EtOAc. The organic layer was concentrated in vacuo, and the residue was purified by Preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1 H$_2$O:MeOH:TFA and B=90:10:0.1 MeOH:H$_2$O:TFA) to provide the title compound (5.0 mg, 7% yield) as a tan lyophilate. [M+H]$^+$=447.0, $^1$NMR (400 MHz, DMSO-d$_6$) δ 7.42-6.63 (m, 8 H), 4.69 (s, 2 H), 1.27 (m, 12 H).

Examples 17 to 27

The following examples were prepared according to the same general procedure described for the synthesis of Example 16.

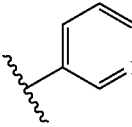

| Example No. | R | [M + H]$^+$ | $^1$H NMR (400 MHz) | Physical Description |
|---|---|---|---|---|
| 17 | 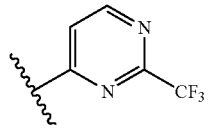 | 432.3 | δ 8.17-6.64 (m, 7 H), 4.68 (s, 2 H), 1.26 (m, 12 H) | Tan lyophilate |
| 18 | 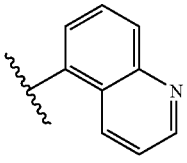 | 483.3 | δ 7.58-6.40 (m, 6 H), 4.64 (s, 2 H), 1.21 (m, 12 H) | Tan lyophilate |
| 19 | 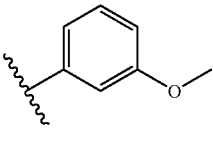 | 464.4 | δ 8.94-6.58 (m, 9 H), 4.67 (s, 2 H), 1.22 (m, 12 H) | Brown/orange lyophilate |
| 20 | 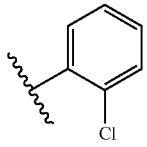 | 443.3 | δ 7.33-6.63 (m, 8 H), 4.67 (s, 2 H), 1.27 (m, 12 H) | Brown lyophilate |
| 21 | 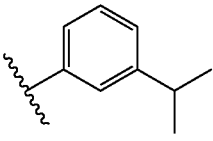 | 447.3 | δ 7.58-6.63 (m, 8 H), 4.68 (s, 2 H), 1.25 (m, 12 H) | Tan lyophilate |
| 22 | | 455.4 | δ 6.48-5.82 (m, 8 H), 3.76 (s, 2 H), 2.10 (m, 1 H), 0.44 (m, 12 H), 0.38 (m, 6 H) | Brown oil |

-continued

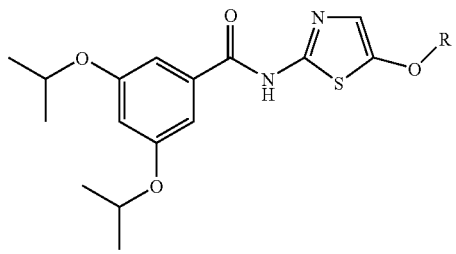

| Example No. | R | [M + H]⁺ | ¹H NMR (400 MHz) | Physical Description |
|---|---|---|---|---|
| 23 | 2-F, 5-Me phenyl | 445.3 | δ 6.41-5.91 (m, 7 H), 3.82 (s, 2 H), 1.50 (s, 3 H), 0.52 (m, 12 H) | Orange/brown oil |
| 24 | 2-Cl, 5-Me phenyl | 461.3 | δ 7.38-6.56 (m, 7 H), 4.62 (s, 2 H), 1.19 (m, 12 H) | Tan lyophilate |
| 25 | 4-Cl, 3-Me phenyl | 461.3 | δ 7.45-6.90 (m, 7 H), 4.68 (s, 2 H), 1.26 (m, 12 H) | Tan lyophilate |
| 26 | 3,5-diF phenyl | 449.3 | δ 7.42-6.63 (m, 7 H), 4.67 (s, 2 H), 1.26 (m, 12 H) | Tan lyophilate |
| 27 | 3-CN phenyl | 438.3 | δ 7.70-6.63 (m, 8 H), 4.69 (s, 2 H), 1.27 (m, 12 H) | Off-white lyophilate |

Example 28

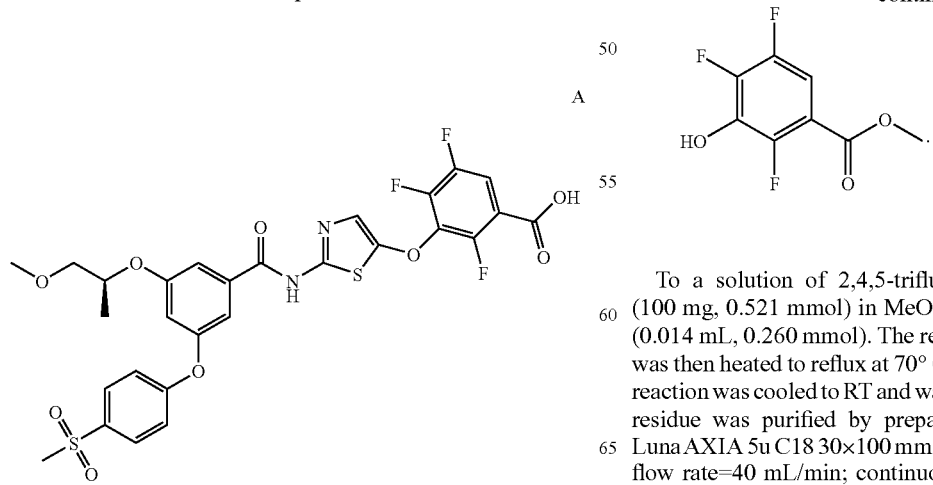

To a solution of 2,4,5-trifluoro-3-hydroxybenzoic acid (100 mg, 0.521 mmol) in MeOH (2 mL) was added $H_2SO_4$ (0.014 mL, 0.260 mmol). The reaction vessel was sealed and was then heated to reflux at 70° C. with shaking for 18 h. The reaction was cooled to RT and was concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to give Part A compound (85 mg, 79% yield) as a white solid.

B

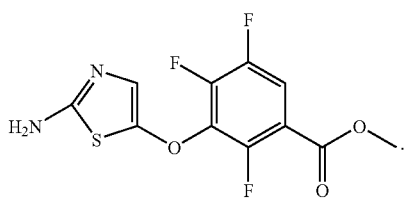

To a solution of Part A compound (85 mg, 0.412 mmol) and 5-bromothiazol-2-amine hydrobromide (107 mg, 0.412 mmol) in acetone (5 mL) was added Cs₂CO₃ (296 mg, 0.907 mmol). The reaction was stirred at 55° C. for 16 h and was filtered and concentrated in vacuo to give crude Part B compound, which was used in the next reaction without further purification or characterization.

C

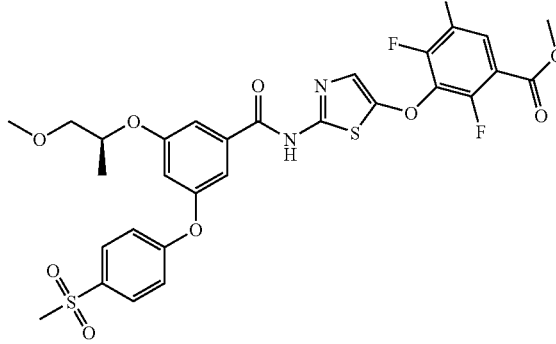

To a solution of Example 1 Part B compound (104 mg, 0.274 mmol) in CH₂Cl₂ (1 mL) was added oxalyl chloride (2M in CH₂Cl₂) (0.315 mL, 0.630 mmol) and DMF (0.1 mL). The reaction was stirred at 25° C. for 1 h, then was concentrated in vacuo to give the crude acid chloride. The Part B (125 mg, 0.411 mmol) and NaHCO₃ (69.0 mg, 0.822 mmol) were dissolved in THF (1.000 mL) and H₂O (1.000 mL). A solution of the crude acid chloride in THF (1 mL) was added to the reaction mixture. The reaction was stirred at RT for 16 h, then was concentrated in vacuo to give crude Part C compound, which was used in the next reaction without further purification.

D

The crude Part C compound (157 mg, 0.236 mmol) was dissolved in MeOH (2 mL) and H₂O (2 mL). LiOH.H₂O (56.4 mg, 2.355 mmol) was added, and the reaction was stirred at RT for 16 h. The reaction was concentrated in vacuo, and the residue was purified by Preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to provide the title compound (1.6 mg, 1% yield over three steps) as an off-white solid. [M+H]⁺=653.1, ¹H NMR (400 MHz, DMSO-d₆) δ 7.95-7.01 (m, 9 H), 4.78 (m, 1 H), 3.49 (m, 2 H), 3.33 (s, 3H), 3.38 (s, 3H), 1.24 (m, 3H).

Example 29

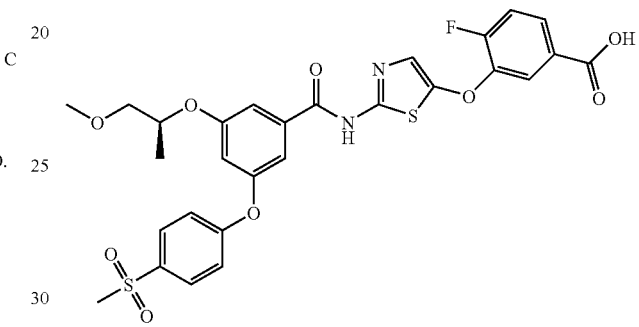

The title compound was prepared from 4-fluoro-3-hydroxybenzoic acid following the same general procedure used to prepare Example 28 to provide the title compound (15 mg, 10% yield over 4 steps) as a tan solid. [M+H]⁺=617.1, ¹H NMR (400 MHz, DMSO-d₆) δ 7.95 (m, 2 H), 7.75 (m, 1 H), 7.65 (m, 1 H), 7.56-7.46 (m, 3 H), 7.35 (s, 1 H), 7.25 (m, 2 H), 7.01 (s, 1 H), 4.77 (m, 1 H), 3.49 (m, 2 H), 3.28 (s, 3 H), 3.21 (s, 3 H), 1.24 (d, J=6.16 Hz, 3 H).

Example 30

A

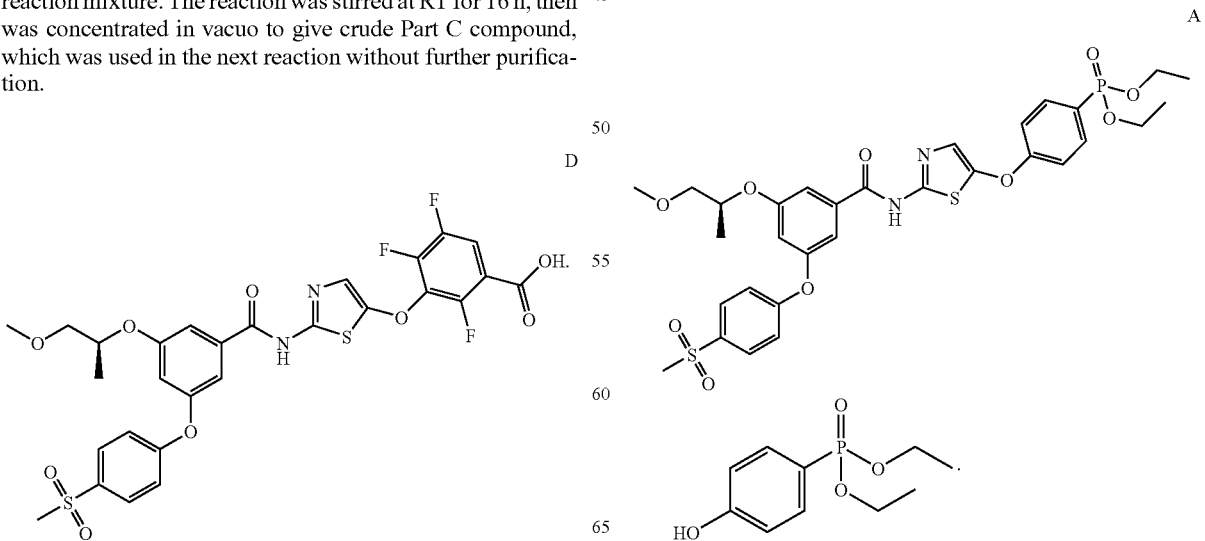

A round bottom flask with a reflux condenser and a magnetic stirring bar was charged with Pd(OAc)₂ (22.45 mg, 0.100 mmol) and Ph₃P (79 mg, 0.300 mmol). The reaction vessel was evacuated and purged with argon. Subsequently, EtOH (20 mL), 4-bromophenol (865 mg, 5.00 mmol), iPr₂NEt (1.310 mL, 7.50 mmol), and diethyl phosphite (0.772 mL, 6.00 mmol) were added via syringe. The reaction mixture was stirred at reflux 76° C. for 16 h, then was cooled to RT. The reaction was diluted with EtOAc and washed with 1N aqueous HCl, saturated aqueous NaHCO₃, and brine. The organic layer was dried (MgSO₄), filtered, and concentrated in vacuo. The residue was chromatographed (80 g SiO₂, continuous gradient from 20% EtOAc to 100% EtOAc for 20 min, then hold for 15 min)) Part A compound (250 mg, 22% yield) was isolated as a colorless oil and was used in the next reaction without further purification.

B

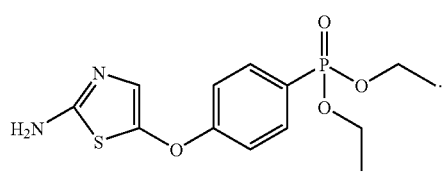

To a solution of 5-bromothiazol-2-amine hydrobromide (141 mg, 0.543 mmol) and Part A compound (125 mg, 0.543 mmol) in acetone (5 mL) was added Cs₂CO₃ (389 mg, 1.195 mmol). The reaction was heated to 60° C. on the shaker for 16 h. The reaction was cooled to RT and was concentrated in vacuo. The residue was taken up in MeOH, was filtered, and was concentrated in vacuo to give Part B compound (155 mg, 43% yield) as an orange/brown solid.

C

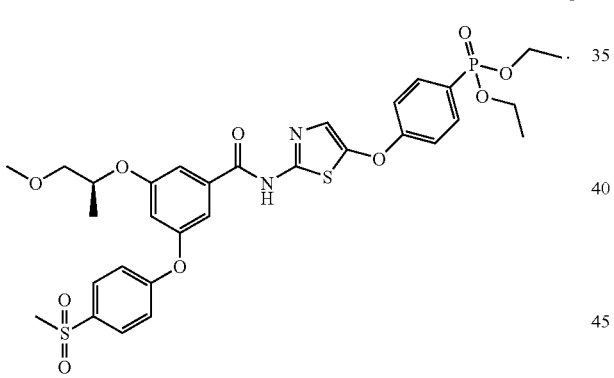

To a solution of the Example 1 Part B compound (100 mg, 0.263 mmol), Part B compound (112 mg, 0.342 mmol), and HOAt (44.7 mg, 0.329 mmol) in DMF (2.0 mL), was added iPr₂NEt (0.060 mL, 0.342 mmol) and EDAC (63.0 mg, 0.329 mmol). The reaction was stirred at RT for 48 h and was then partitioned between EtOAc and water. The organic layer was washed with brine, dried (MgSO₄), filtered, and concentrated in vacuo. The residue was taken up in MeOH and was purified by Preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to provide the title compound (35 mg, 20% yield) as a tan solid. [M+H]⁺=691.1, ¹H NMR (400 MHz, DMSO-d₆) δ 7.95 (m, 2 H), 7.73 (m, 2 H), 7.55 (s, 1 H), 7.44 (s, 1 H), 7.35 (s, 1 H), 7.25 (m, 4 H), 7.01 (s, 1 H), 4.78 (m, 1 H), 3.98 (m, 4 H), 3.49 (m, 2 H), 3.28 (s, 3H), 3.21 (s, 3H), 1.21 (m, 9 H).

Example 31

A

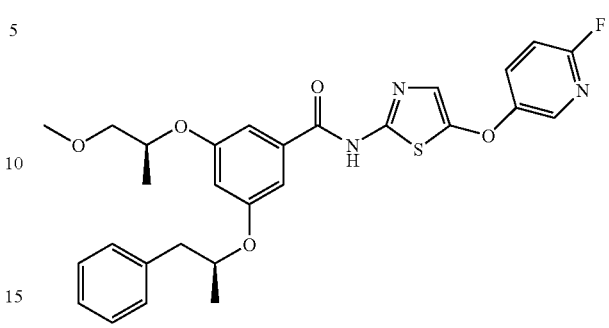

i

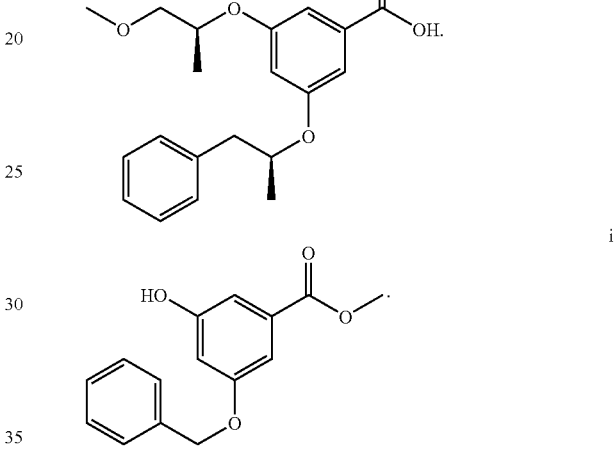

To a solution of 3,5-dihydroxymethyl benzoate (10.0 g, 59.5 mmol) in DMF (60.0 mL) under an atmosphere of Ar (g) was added K₂CO₃ (12.4 g, 89.7 mmol) at RT. Benzyl bromide (10.0 mL, 84.2 mmol; filtered through basic Al₂O₃ prior to use) was added slowly over 10 min. The reaction mixture was stirred for 12 h at RT and was carefully quenched with saturated aqueous NH₄Cl (50 mL), followed by H₂O (350 mL). The aqueous suspension was extracted with CH₂Cl₂ (1×30 mL, 2×50 mL). The combined extracts were washed with H₂O (100 mL) and brine, dried (MgSO₄), filtered, and concentrated in vacuo to give the crude product (27.0 g) as a golden-colored oil. The crude material was chromatographed (product eluted during the 30% EtOAc/hexane portion of a stepwise gradient (10-50% EtOAc/hexane) to yield Part A(i) compound (4.6 g, 30% yield) as a cream-colored powder.

ii

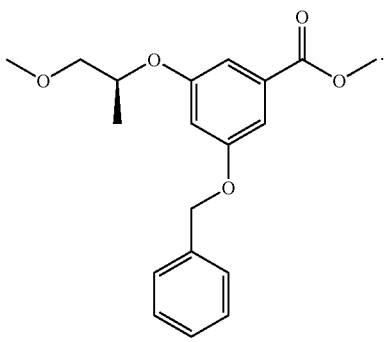

To a 0° C. solution of Part A(i) compound (1.0 g, 3.9 mmol) in THF (16.8 mL) was added (R)-(−)-1-methoxy-2-propanol (0.5 g, 5.8 mmol). Ph₃P (1.5 g, 5.8 mmol) was then added, followed by slow addition of DIAD (1.1 mL, 5.8 mmol). The reaction mixture was warmed to RT and was stirred for 2 days. The reaction mixture was diluted with H₂O and extracted with Et₂O. The organic layer was dried (MgSO₄), filtered, and concentrated in vacuo to give the crude product as a thick, pale, yellow oil. The crude material was chromatographed (product eluted during the 10% EtOAc/hexane portion of a stepwise gradient of 10-30% EtOAc/hexane) to give Part A(ii) compound (1.1 g, 85% yield) as a colorless oil.

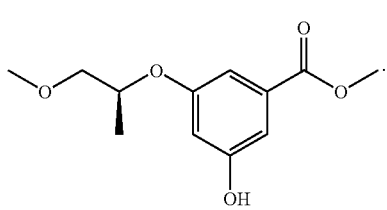

iii

A flask containing Part A(ii) compound (1.2 g, 3.6 mmol) in MeOH (45.4 mL) was evacuated and flushed with Ar (g). In one portion, 10% Pd/C (0.38 g, 0.36 mmol) was added. The flask was evacuated and fit with a hydrogen balloon via a three-way stopcock and was stirred for 12 h at RT. The reaction mixture was filtered through Celite® and was rinsed with EtOAc. The filtrate was concentrated in vacuo to give Part A(iii) compound (0.81 g, 93% yield) as a yellow oil.

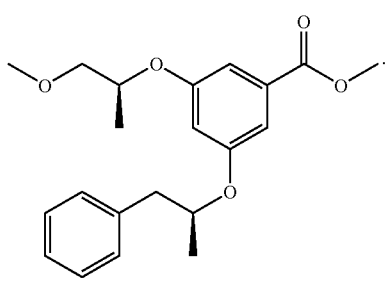

iv

To a 0° C. solution of Part A(iii) compound (0.14 g, 0.59 mmol) in THF (2.9 mL) was added Ph₃P (0.4 g, 1.3 mmol) and (R)-1-phenylpropan-2-ol (0.2 g, 1.3 mmol) under an atmosphere of Ar (g). The reaction mixture was allowed to stir for 5 min, then DIAD (0.3 mL, 1.3 mmol) was added dropwise. The reaction mixture was stirred at RT for 12 h. The mixture was diluted with H₂O and extracted with EtOAc. The combined organic layers were washed with 1N aqueous NaOH and brine, dried (MgSO₄), filtered, and concentrated in vacuo to give the crude compound (1.0 g) as a pale, yellow oil. The crude material was chromatographed (product eluted during the 10% EtOAc/hexane portion of a stepwise gradient from 5-20% EtOAc/hexane) to give Part A(iv) compound (0.17 g, 81% yield) as a near-colorless oil.

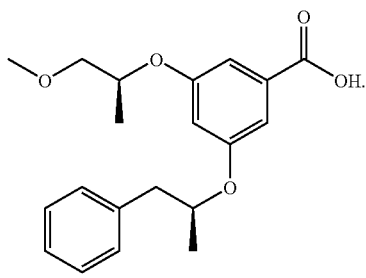

v

To a solution of Part A(iv) compound in THF (1.8 mL) and H₂O (0.6 mL) was added LiOH.H₂O (0.02 g, 0.52 mmol) at RT. The reaction mixture was stirred at 45° C. for 1 h; an additional portion of LiOH.H₂O was added, and stirring was continued at 45° C. The starting material was consumed after 6 h. Solvent was removed in vacuo, and the remaining aqueous layer was acidified with 0.5N aqueous HCl to pH 2, which was then extracted with EtOAc (3×). The combined organic layers were washed with brine, dried (MgSO₄), filtered, and concentrated in vacuo to give crude Part A(v) compound (0.16 g, 86% yield) as a pale-yellow oil.

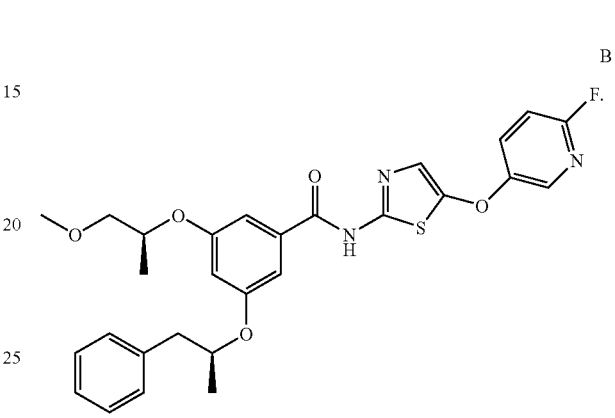

B

To a solution of the Part A(v) compound (24 mg, 0.070 mmol), Example 10 Part A compound (19.13 mg, 0.091 mmol), and HOAT (11.86 mg, 0.087 mmol) in DMF (2 mL), was added iPr₂NEt (0.016 mL, 0.091 mmol) and EDC (16.70 mg, 0.087 mmol). The reaction was stirred at RT for 48 h, then was concentrated in vacuo. The residue was taken up in MeOH and was purified by preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H₂O:MeOH:TFA and B=90:10:0.1 MeOH:H₂O:TFA) to provide the title compound (6.5 mg, 18% yield) as a colorless oil. [M+H]⁺=538.1, ¹H NMR (400 MHz, DMSO-d₆) δ 7.98-6.60 (m, 12 H), 4.63 (m, 2 H), 3.58 (m, 2 H), 3.22 (s, 3H), 2.83 (m, 2 H), 1.20 (m, 3H).

Example 32

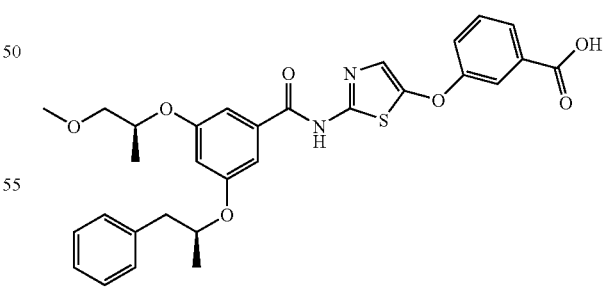

The title compound was prepared from Example 31 Part A compound and Example 4 Part A compound following the same general procedure used to prepare Example 4 compound to provide the title compound (6 mg, 15% yield) as a white solid. [M+H]⁺=563.1, ¹H NMR (400 MHz, DMSO-d₆) δ 7.75-6.64 (m, 13 H), 4.68 (m, 2 H), 3.52 (m, 2 H), 3.26 (s, 3 H), 2.85 (m, 2 H), 1.24 (m, 3 H).

Example 33

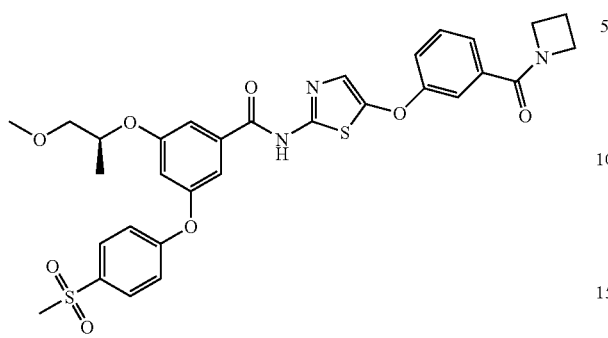

To a solution of the Example 4 compound (25 mg, 0.042 mmol), azetidine hydrochloride (5.08 mg, 0.054 mmol), and HOAT (7.11 mg, 0.052 mmol) in DMF (2 mL) was added Hunig's Base (0.019 mL, 0.109 mmol) and EDC (10.01 mg, 0.052 mmol). The reaction was stirred at 25° C. for 18 h and was concentrated in vacuo. The residue was purified using Preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA) to provide the title compound (15.65 mg, 59% yield) as a white solid lyophilate. [M+H]$^+$=638.4, $^1$H NMR (500 MHz, CD$_3$OD) δ 7.97-6.95 (m, 12 H), 4.72 (m, 1 H), 4.35 (m, 2 H), 4.18 (m, 2H), 3.57 (m, 2 H), 3.39 (s, 3H), 3.12 (s, 3H), 2.35 (m, 2 H), 1.32 (m, 3 H).

Example 34

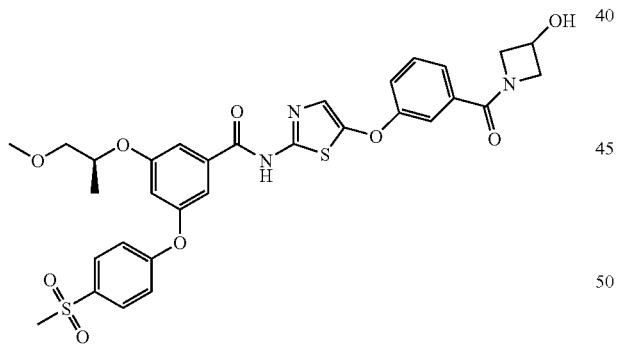

To a solution of the Example 4 compound (25 mg, 0.042 mmol), 3-hydroxy azetidine hydrochloride (5.95 mg, 0.054 mmol), and HOAT (7.11 mg, 0.052 mmol) in DMF (2 mL) was added Hunig's base (0.019 mL, 0.109 mmol) and EDC (10.01 mg, 0.052 mmol). The reaction was stirred at 25° C. for 18 h, then was concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA) to provide the title compound (8.1 mg, 30% yield) as a white solid lyophilate. [M+H]$^+$=654.1, $^1$H NMR (500 MHz, CD$_3$OD) δ 7.97-6.97 (m, 12 H), 4.71 (m, 1 H), 4.18 (m, 2 H), 3.95 (m, 2H), 3.58 (m, 2 H), 3.39 (s, 3H), 3.12 (s, 3H), 1.32 (m, 3 H).

Example 35

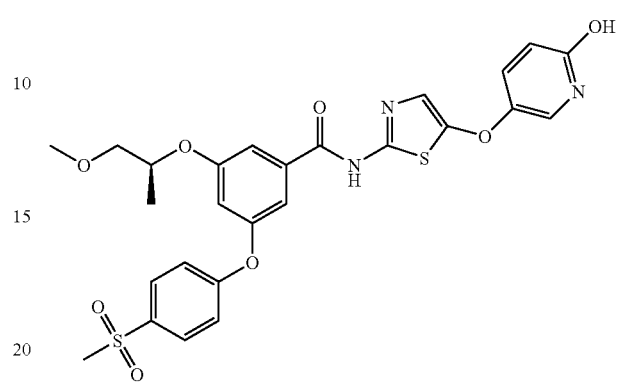

A solution of Example 10 compound (50 mg, 0.087 mmol) in 1N aqueous NaOH (523 µL, 0.523 mmol) was heated in the microwave at 140° C. for 7 min, then was cooled to RT. The reaction was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA) to provide the title compound (8.5 mg, 17% yield) as an off-white lyophilate. [M+H]$^+$=572.3, $^1$H NMR (500 MHz, DMSO-d$_6$) δ ppm 7.86-6.34 (m, 11H), 4.68 (m, 1 H), 3.40 (m, 2 H), 3.19 (s, 3H), 3.12 (s, 3H), 1.15 (m, 3 H).

Example 36

To a solution of 5-hydroxynicotinic acid (200 mg, 1.438 mmol) in MeOH (2 mL) was added concentrated H$_2$SO$_4$ (0.077 mL, 1.438 mmol). The sealed reaction vessel was placed on a shaker and was heated to reflux at 70° C. for 18 h, then was cooled to RT. The volatiles were removed in vacuo, and the residue was purified by preparative HPLC (Phenomenex Luna AXIA 5u C18 30×100 mm column; detection at 220 nm; flow rate=40 mL/min; continuous gradient from 0% B to 100% B over 10 min+2 min hold time at 100% B, where A=90:10:0.1 H₂O:MeOH:TFA and B=90:10:0.1 MeOH:H₂O:TFA) to give Part A methyl ester (180 mg, 82% yield) as a white solid.

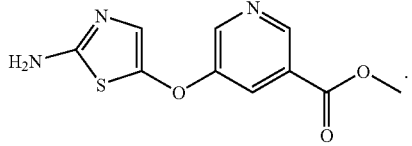

B

To a solution of Part A compound (180 mg, 1.175 mmol) in acetone (5 mL) was added 2-amino-5-bromothiazole monohydrobromide (611 mg, 2.351 mmol) and Cs₂CO₃ (957 mg, 2.94 mmol). The mixture was stirred at reflux (55° C.) for 18 h, then was cooled to RT and was filtered. The filtrate was concentrated in vacuo. The residue was taken up in EtOAc and was washed with H₂O and brine, then was dried (MgSO₄), filtered, and concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give Part B compound (200 mg, 67% yield) as a yellow solid.

To a solution of Example 1 Part B compound (114 mg, 0.298 mmol), Part B compound (50 mg, 0.199 mmol), and HOAT (54.2 mg, 0.398 mmol) in DMF (1 mL) was added Hunig's Base (0.069 mL, 0.398 mmol) and EDC (76 mg, 0.398 mmol). The reaction was stirred at 25° C. for 18 h. An additional portion of Part B compound (25 mg, 0.10 mmol) was added, and the reaction was stirred at 25° C. for 48 h, then was concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give Part C compound (11 mg, 9% yield) as a yellow solid lyophilate.

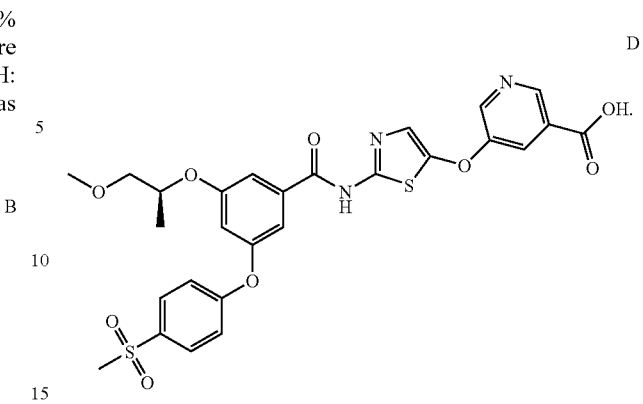

To a solution of Part C compound (11 mg, 0.018 mmol) in THF (2 mL):water (1 mL) was added LiOH.H₂O (4.29 mg, 0.179 mmol). The reaction was stirred at RT for 18 h under an atmosphere of Ar(g). The pH of the reaction mixture was adjusted to pH~7 using 1N aqueous HCl. The reaction mixture was concentrated in vacuo, and the residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to provide the title compound (8 mg, 74% yield) as a pale yellow solid lyophilate. [M+H]⁺=600.3, ¹H NMR (500 MHz, DMSO-d₆) δ 8.76-6.89 (m, 11 H), 4.68 (m, 1 H), 3.40 (m, 2 H), 3.23 (s, 3H), 3.15 (s, 3H), 1.18 (m, 3 H).

Example 37

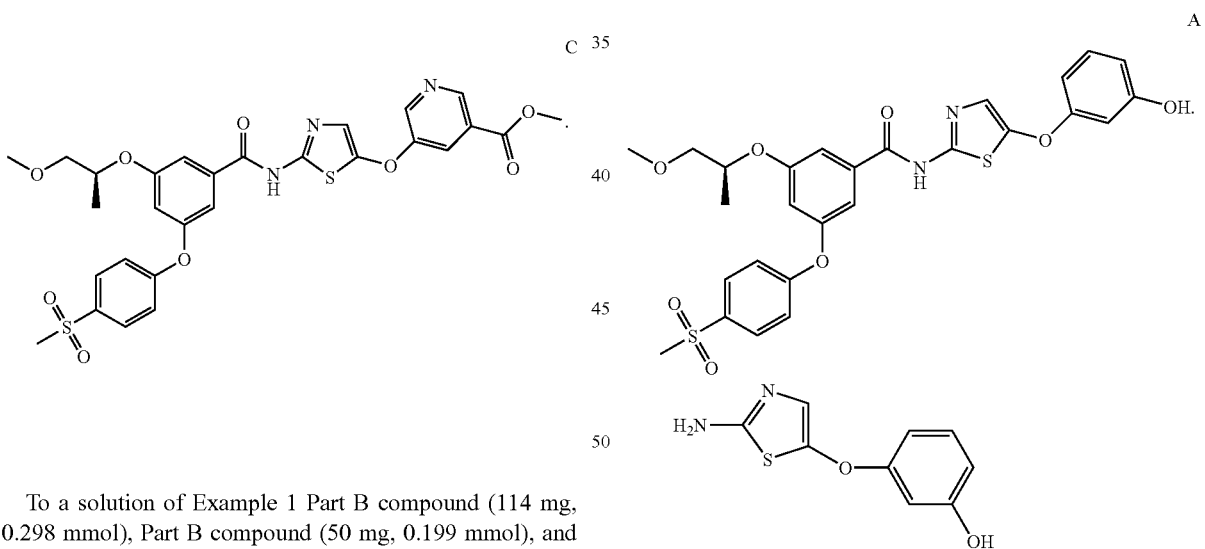

To a solution of 2-amino-5-bromothiazole monohydrobromide (495 mg, 1.904 mmol) in Acetone (9.5 mL) was added resorcinol (315 mg, 2.86 mmol) and Cesium carbonate (1203 mg, 3.69 mmol). The reaction mixture was stirred at reflux for 14 h. The mixture was filtered and was washed with acetone. The filtrate was concentrated in vacuo. The residue was diluted with EtOAc and was washed with brine, dried (MgSO₄), filtered, and concentrated in vacuo. The residue was purified by preparative HPLC (Phenomenex Luna AXIA 5u C18 30×100 mm column; detection at 220 nm; flow rate=40 mL/min; continuous gradient from 10% B to 100% B over 10 min+5 min hold time at 100% B, where A=90:10:0.1 H₂O:MeOH:TFA and B=90:10:0.1 MeOH:H₂O:TFA) to provide the Part A compound (45 mg, 11%) as a brown oil.

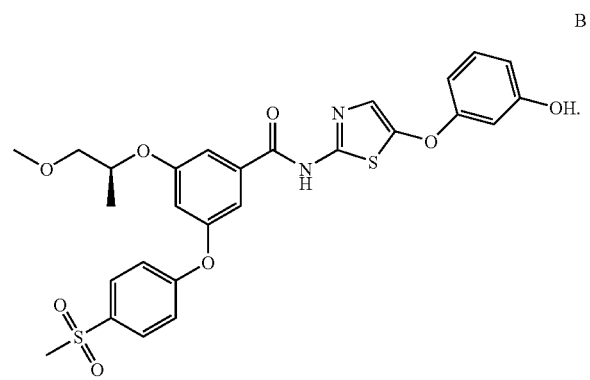

B

To a solution of Example 1 Part B compound (82 mg, 0.216 mmol) in DMF (1 mL) was added Part A compound (45 mg, 0.216 mmol), EDC (83 mg, 0.432 mmol), HOBT (66.2 mg, 0.432 mmol), and Hunig's Base (0.113 mL, 0.648 mmol). The reaction mixture was stirred at RT for 3 days. The reaction mixture was purified directly by preparative HPLC (Phenomenex Luna AXIA 5u C18 30×100 mm column; detection at 220 nm; flow rate=40 mL/min; continuous gradient from 50% B to 100% B over 10 min+5 min hold time at 100% B, where A=90:10:0.1 H₂O:MeOH:TFA and B=90:10:0.1 MeOH:H₂O:TFA) to provide the title compound (6 mg, 5% yield) as a brown oil. [M+H]⁺=571.3, $^1$H NMR (500 MHz, CDCl₃) δ 7.89-7.96 (2 H, m), 7.63 (1 H, d, J=25.29 Hz), 7.44 (1 H, d, J=16.50 Hz), 7.24 (1 H, t, J=8.25 Hz), 7.16 (2 H, dd, J=9.35, 2.20 Hz), 7.12 (1 H, s), 6.92-6.97 (1 H, m), 6.74-6.88 (1 H, m), 6.61-6.72 (1 H, m), 4.59-4.93 (1 H, m), 3.51-3.67 (2 H, m), 3.43 (3 H, d, J=4.95 Hz), 3.08 (3 H, d, J=6.05 Hz), 1.36 (3 H, dd, J=6.05, 2.20 Hz).

Example 38

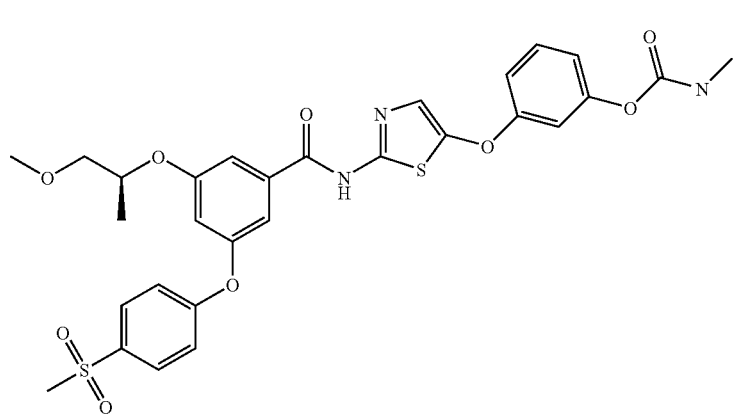

A

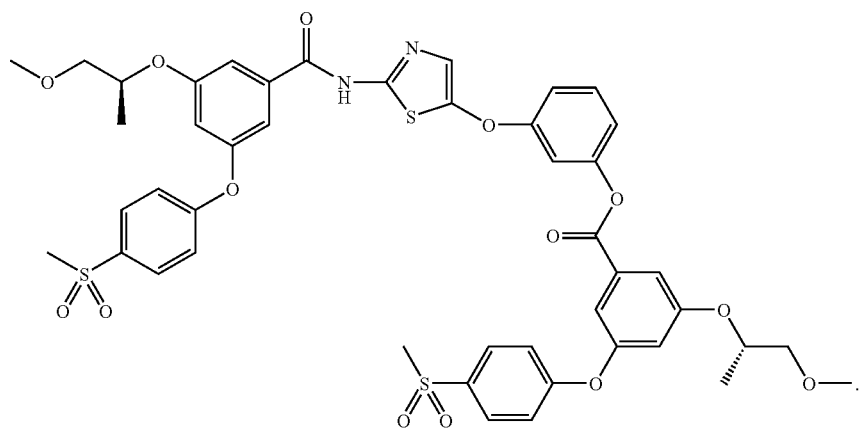

In addition to isolating the title compound in Example 37 Part B, Example 38 Part A compound was isolated (11 mg, 5% yield) as a white solid. Part A compound was used in the next reaction.

B

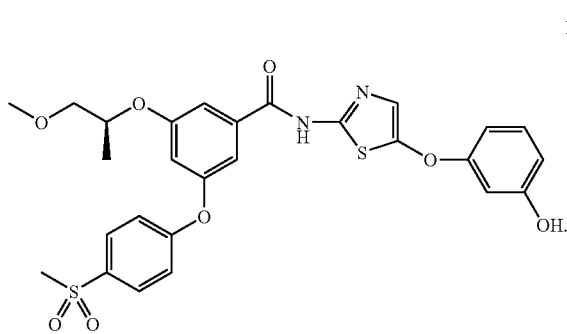

To a solution of Part A compound (11 mg, 0.012 mmol) in THF (1 mL), was added 1N aqueous NaOH (0.3 mL, 0.300 mmol). The resulting mixture was stirred at RT for 1 h. The mixture was diluted with EtOAc (3 mL) and acidified with 1N aqueous HCl (0.4 mL). The organic layer was washed with brine, dried (MgSO$_4$) and concentrated in vacuo to afford the crude Part B compound (10 mg, 149% yield) as a brown oil, which was used in the next step without further purification.

C

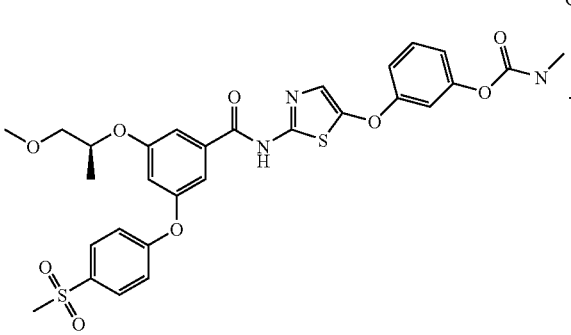

To a mixture of crude Part B compound (10 mg, 0.018 mmol) in CH$_2$Cl$_2$ (1 mL), was added methyl isocyanate (10.00 mg, 0.175 mmol). The resulting mixture was stirred at RT for 18 h. The reaction mixture was concentrated in vacuo, and the residue was purified by preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to provide the title compound (4.0 mg, 54% yield) as a yellow oil. [M+H]$^+$=628.3, $^1$H NMR (500 MHz, CDCl$_3$) δ 7.93 (2 H, d, J=8.80 Hz), 7.68 (1 H, s), 7.44 (1 H, s), 7.35-7.41 (1 H, m), 7.16 (3 H, d, J=8.80 Hz), 6.96-7.05 (3 H, m), 6.93-6.96 (1 H, m), 5.01 (1 H, d, J=4.40 Hz), 4.87-4.96 (1 H, m), 3.56-3.63 (2 H, m), 3.43 (3 H, s), 3.08 (3 H, s), 2.91 (3 H, d, J=4.95 Hz), 1.36 (3 H, d, J=6.05 Hz).

Example 39

A

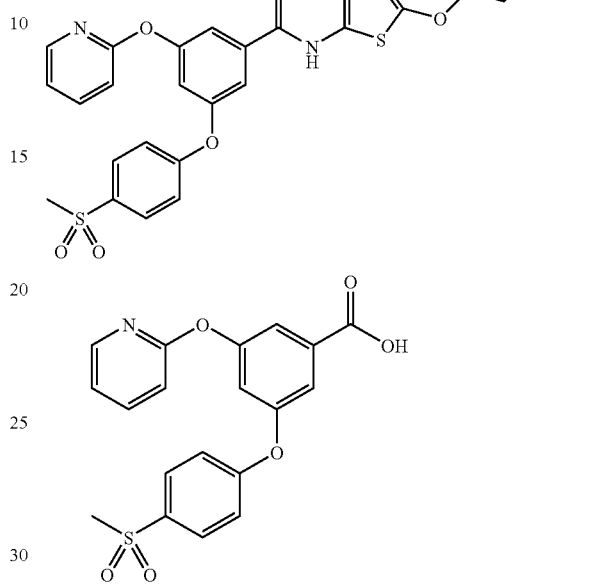

To a solution of Example 6 Part B(i) compound (150 mg, 0.465 mmol) in DMF (1 mL) was added 2-chloropyridine (0.088 ml, 0.931 mmol) and K$_2$CO$_3$ (193 mg, 1.396 mmol). The reaction was heated to 120° C. and stirred for 2 days at 120° C., then cooled to RT. LiCl (59.2 mg, 1.396 mmol) was added to the reaction mixture, which was heated to 120° C. and stirred for an additional 3 days at 120° C. The reaction was cooled to RT and filtered. The filtrate was concentrated in vacuo and purified by preparative HPLC (Phenomenex Luna AXIA 5u C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to provide Part A compound (38 mg, 21% as a white solid. [M+H]$^+$=386.3.

B

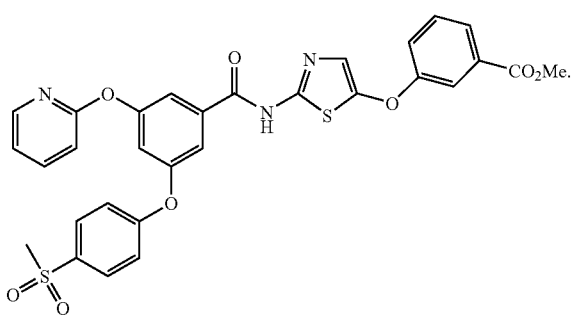

To a solution of Part A compound (38 mg, 0.099 mmol) in DMF (1 mL) was added Example 4 Part A compound (49.4 mg, 0.197 mmol), EDC (37.8 mg, 0.197 mmol), HOBT (30.2 mg, 0.197 mmol), and Hunig's Base (0.052 mL, 0.296 mmol). The reaction was stirred at RT for 4 days. The reaction was purified directly by preparative HPLC (Phenomenex Luna AXIA 5u C18 30×100 mm column; detection at 220 nm; flow rate=40 mL/min; continuous gradient from 15% B to 100% B over 10 min+2 min hold time at 100% B, where A=90:10:0.1 $H_2O$:MeOH:TFA and B=90:10:0.1 MeOH:$H_2O$:TFA) to provide the Part B compound (15 mg, 25%) as a yellow solid. [M+H]+=618.4.

C

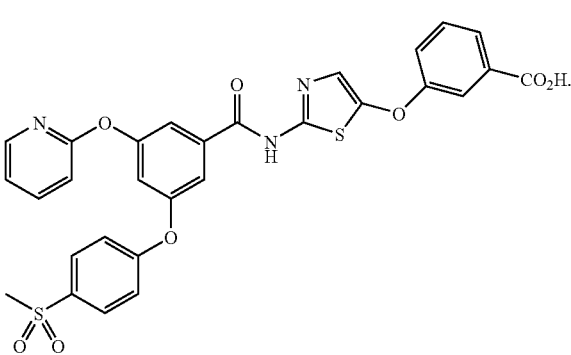

To a solution of Part B compound (15 mg, 0.024 mmol) in THF (1.5 mL) was added 1N aqueous NaOH (0.486 mL, 0.486 mmol). The mixture was stirred at RT for 20 h, then was diluted with EtOAc (6 mL) and acidified with 1N aqueous HCl (1.0 mL). The organic layer was washed with brine, dried (MgSO$_4$) and concentrated in vacuo to afford the crude product, which was purified by preparative HPLC (Phenomenex Luna AXIA 5u C18 30×100 mm column; detection at 220 nm; flow rate=40 mL/min; continuous gradient from 15% B to 100% B over 10 min+2 min hold time at 100% B, where A=90:10:0.1$H_2O$:MeOH:TFA and B=90:10:0.1 MeOH:$H_2O$:TFA) to provide the title compound (4.5 mg, 31%), as a white solid. [M+H]$^+$=604.4. $^1$H NMR (400 MHz, CDCl$_3$) δ 8.28 (1H, d, J=4.39 Hz), 7.94 (2H, d, J=7.91 Hz), 7.91 (1H, d, J=7.47 Hz), 7.85 (1H, t, J=7.69 Hz), 7.79 (2H, br. s.), 7.70 (1H, s), 7.51 (1H, t, J=7.91 Hz), 7.39 (1H, dd, J=8.35, 2.64 Hz), 7.24 (1H, s), 7.21 (2H, br. s.), 7.13-7.19 (2H, m), 7.09 (1H, d, J=8.35 Hz), 3.07 (3H, s).

Examples 40 to 42

The following examples were prepared according to the general procedure described for the synthesis of Example 39, using the appropriate corresponding substituted phenols.

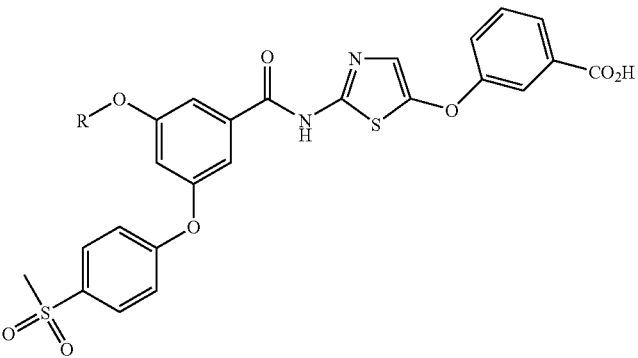

| Example No. | Starting Material Halide Used | R | [M + H]+ | $^1$H NMR (400 MHz, CDCl$_3$) | Physical Description |
|---|---|---|---|---|---|
| 40 | ![F-pyridine-F] | ![F-pyridine] | 622.4 | δ 7.96 (2H, dd, J = 8.79, 1.76 Hz), 7.91 (1H, d, J = 7.91 Hz), 7.83-7.87 (1H, m), 7.82 (1H, s), 7.78 (1H, s), 7.72 (1H, s), 7.48-7.55 (1H, m), 7.36-7.43 (1H, m), 7.23 (2H, dd, J = 4.17, 1.98 Hz), 7.16 (2H, d, J = 1.76 Hz), 6.92 (1H, d, J = 7.91 Hz), 6.66-6.73 (1H, m), 3.08 (3H, s) | White solid |

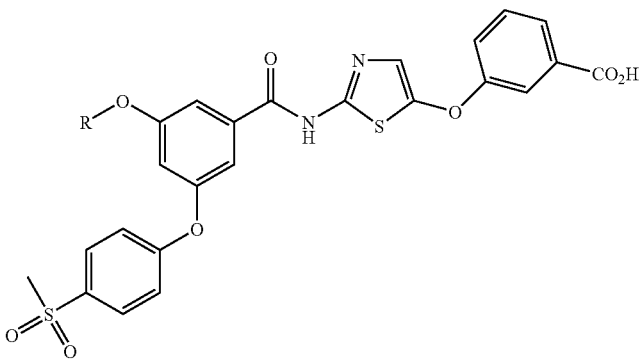

| Example No. | Starting Material Halide Used | R | [M + H]⁺ | ¹H NMR (400 MHz, CDCl₃) | Physical Description |
|---|---|---|---|---|---|
| 41 | 3,5-difluoropyridine | 5-fluoropyridin-3-yl | 622.4 | δ 8.38 (2H, dd, J = 10.33, 1.98 Hz), 7.98 (2H, d, J = 8.79 Hz), 7.91 (1H, d, J = 7.47 Hz), 7.77 (1H, s), 7.67-7.73 (2H, m), 7.52 (1H, t, J = 8.13 Hz), 7.37-7.45 (2H, m), 7.24 (2H, d, J = 8.79 Hz), 7.19 (1H, s), 7.15 (1H, t, J = 2.20 Hz), 3.08 (3H, s) | White solid |
| 42 | 2-chloro-4-fluoropyridine | 2-chloropyridin-4-yl | 638.4 | δ 8.32 (1H, d, J = 5.27 Hz), 7.97 (2H, d, J = 8.35 Hz), 7.80 (2H, br. s.), 7.67 (1H, s), 7.57 (1H, d, J = 7.91 Hz), 7.35-7.48 (2H, m), 7.20-7.25 (2H, m), 7.12 (1H, s), 7.09 (1H, s), 6.95 (1H, s), 6.90 (1H, d, J = 5.71 Hz), 3.06 (3H, s) | White solid |

Example 43

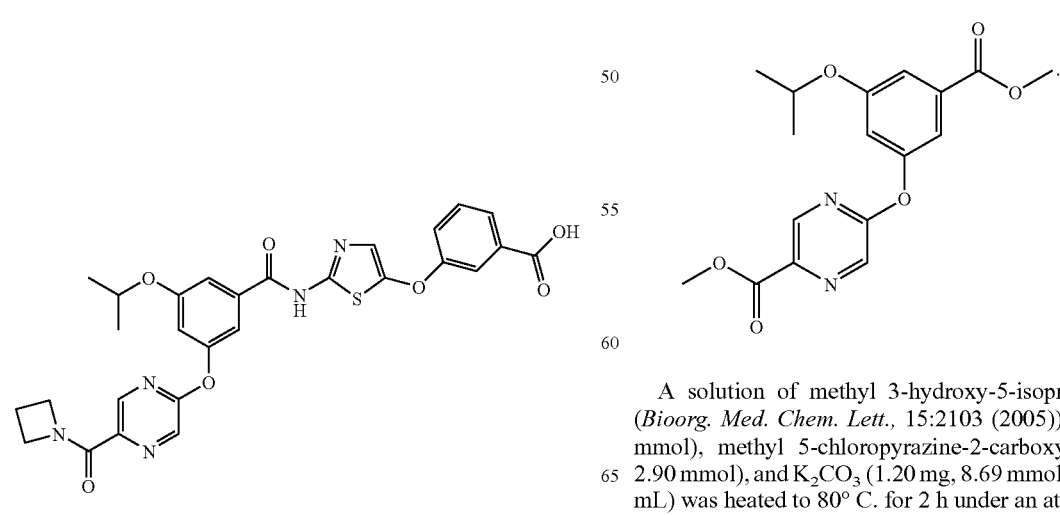

A solution of methyl 3-hydroxy-5-isopropoxybenzoate (*Bioorg. Med. Chem. Lett.*, 15:2103 (2005)) (609 mg, 2.90 mmol), methyl 5-chloropyrazine-2-carboxylate (500 mg, 2.90 mmol), and K₂CO₃ (1.20 mg, 8.69 mmol) in CH₃CN (20 mL) was heated to 80° C. for 2 h under an atmosphere of Ar (g). The reaction was cooled to RT, diluted with CH₂Cl₂ (50 mL) and filtered. The filtrate was concentrated in vacuo, and the residue was chromatographed (SiO$_2$; 40 g; continuous gradient from 100% hexane to 100% EtOAc over 40 min) to provide Part A compound (1.005 g, 100% yield) as a colorless oil. [M+H]$^+$=347.

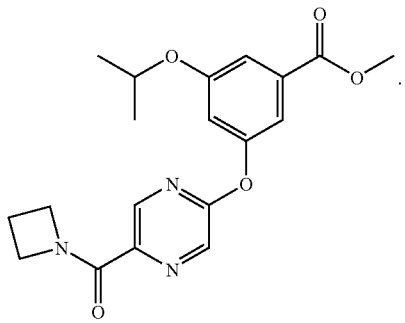

B

A mixture of Part B compound (1.005 g, 2.9 mmol), azetidine hydrochloride (326 mg, 3.48 mmol), Et$_3$N (0.485 mL, 3.48 mmol), and MgCl$_2$ (332 mg, 3.48 mmol) was stirred at RT for 5 h. Additional portions of azetidine hydrochloride (326 mg, 3.48 mmol), Et$_3$N (0.485 mL, 3.48 mmol), and MgCl$_2$ (332 mg, 3.48 mmol) were added. The reaction was stirred at RT for 30 min, and then stored at 0° C. overnight. The reaction was diluted with CH$_2$Cl$_2$ (50 mL), and filtered. The filtrate was concentrated in vacuo, and the residue was chromatographed (SiO$_2$; 40 g; continuous gradient from 100% hexane to 100% EtOAc over 40 min) to provide Part B compound (267 mg, 25% yield) as a colorless oil. [M+H]$^+$=372.

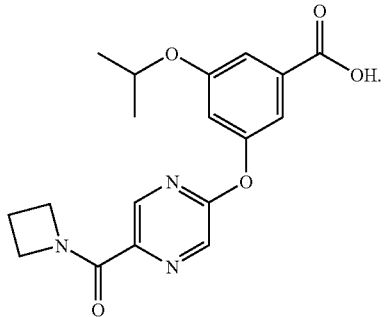

C

A solution of Part B compound (267 mg, 0.72 mmol) and LiOH.H$_2$O (90 mg, 2.16 mmol) in THF (4 mL)/H$_2$O (4 mL) was stirred at RT for 5 h. The reaction was acidified to pH 2 with 1N aqueous HCl, and then was extracted with EtOAc (3×10 mL). The combined organic extracts were washed with brine (10 mL), dried (MgSO$_4$), filtered, and concentrated in vacuo to give Part C compound (200 mg, 78% yield) as a white solid. [M+H]$^+$=358.

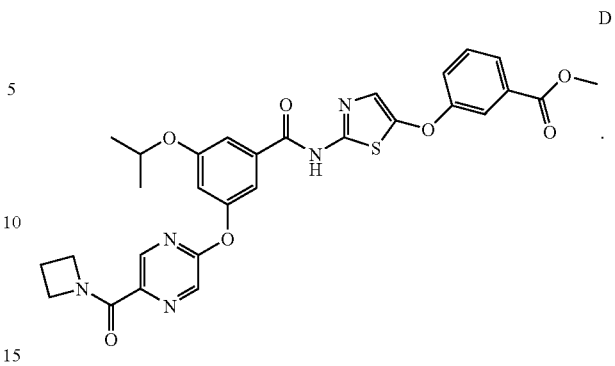

D

To a solution of Part C compound (50 mg, 0.140 mmol) in DCM (1 mL) was added 1-chloro-N,N,2-trimethylprop-1-en-1-amine (0.022 mL, 0.168 mmol). The reaction was stirred at 25° C. for 30 min. When all of the acid was converted to the acid chloride, Example 4 Part A compound (42.0 mg, 0.168 mmol) and 2,6-lutidine (0.041 mL, 0.350 mmol) were added. The reaction was stirred at 25° C. for 18 h. Another portion of Example 4 Part A compound (42.0 mg, 0.168 mmol) was added, followed by addition of pyridine (0.023 mL, 0.280 mmol). The reaction was stirred at 25° C. for 48 h. The reaction was concentrated in vacuo, and the residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10:0.1 MeOH:H$_2$O:TFA) to provide the Part D compound (20 mg, 24% yield) as a tan solid. [M+H]+=590.5.

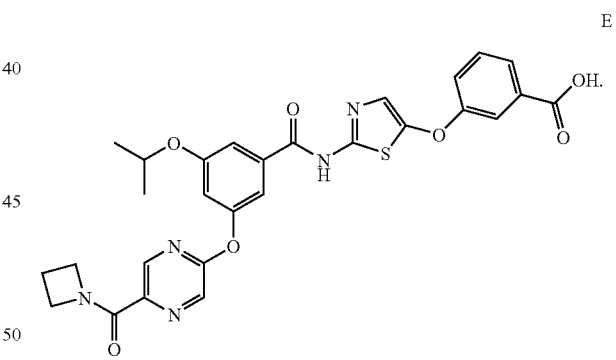

E

To a solution of Part D compound (20 mg, 0.034 mmol) in THF (1 mL) was added 1N aqueous NaOH (0.051 mL, 0.051 mmol). The reaction was stirred at 25° C. for several hours. An additional portion of 1N aqueous NaOH (0.025 mL) was added, and the reaction was stirred at 25° C. for 18 h. The reaction was neutralized with 1N aqueous HCl and purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10:0.1 MeOH:H$_2$O:TFA) to provide the title compound (5 mg, 26% yield) as a solid tan lyophilate. [M+H]$^+$=576.5. $^1$H NMR (400 MHz, MeOH-d$_3$) δ 8.72 (s, 1H), 8.48 (s, 1H), 7.92 (m, 1H), 7.87 (s, 1H), 7.79 (m, 1H), 7.72 (s, 1H), 7.45 (m, 1H), 7.40 (s, 1H), 7.18 (m, 1H), 7.05 (s, 1H), 4.22 (m, 2H), 4.15 (m, 1H), 3.55 (m, 2H), 2.41 (m, 2H), 1.35 (m, 6H).

Example 44

A

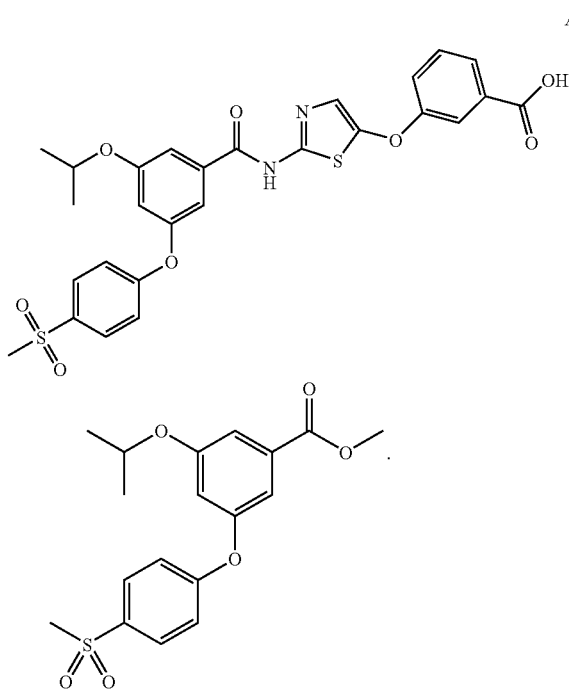

To a 0° C. solution of Example 6 Part B(i) compound (2.00 g; 6.2 mmol) in THF (31.0 mL) was added propan-2-ol (0.82 g, 13.7 mmol) and Ph₃P (3.6 g; 13.7 mmol) followed by the dropwise addition of DIAD (2.7 mL; 13.7 mmol). The reaction was stirred at 25° C. for 16 h under an atmosphere of Ar (g). The reaction was diluted with H₂O and extracted with EtOAc (3×). The combined organic extracts were washed with 1N aqueous NaOH and brine, dried (MgSO₄) and concentrated in vacuo. The crude residue was chromatographed (SiO₂; step gradient from 10-20-40% solvent B, where solvent A=hexanes and solvent B=EtOAc) to give Part A compound (2.4 g; 100%).

B

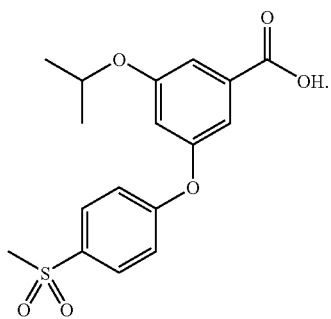

To a solution of Part A compound (2.3 g; 6.33 mmol) in THF (52.3 mL) and H₂O (5.23 mL) was added LiOH.H₂O (0.61 g; 25.3 mmol). The reaction was stirred at 45° C. for 1 h in a sealed vial, then was cooled to RT. An additional equivalent of LiOH.H₂O was added due to minimal conversion of starting material to product. The reaction was stirred at 50° C. for 16 h. The solvent was removed in vacuo, and the remaining aqueous solution was acidified with 0.5N aqueous HCl until pH<2. The aqueous layer was extracted with EtOAc (3×). The combined organic extracts were washed with brine, dried (MgSO₄) and concentrated in vacuo to give Part B compound (2.07 g; 88%).

C

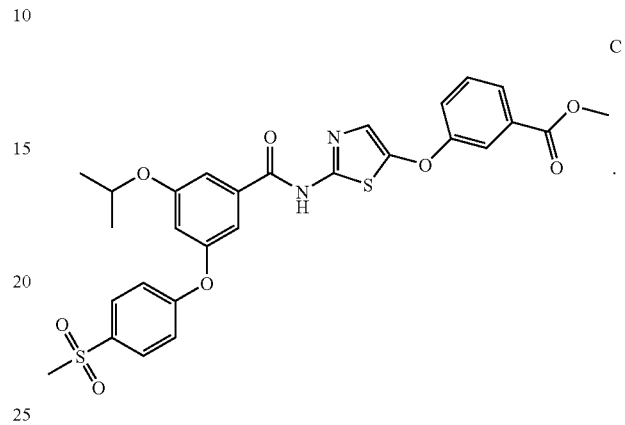

To a solution of Part B compound (50 mg, 0.143 mmol) in DCM (1 mL) was added 1-chloro-N,N,2-trimethylprop-1-en-1-amine (0.023 mL, 0.171 mmol). The reaction was stirred at 25° C. for 30 min. When all of the acid had been converted to the acid chloride, Example 4 Part A compound (42.9 mg, 0.171 mmol) and 2,6-lutidine (0.042 mL, 0.357 mmol) were added. The reaction was stirred at 25° C. for 18 h, after which more Example 4 Part A compound (42.9 mg, 0.171 mmol) was added, followed by pyridine (0.023 mL, 0.285 mmol). The reaction was stirred at 25° C. for 48 h, and then was concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H₂O:MeOH:TFA and B=90:10:0.1 MeOH:H₂O:TFA) to provide Part C compound (20 mg, 25% yield) at an oil. [M+H]+=583.5.

D

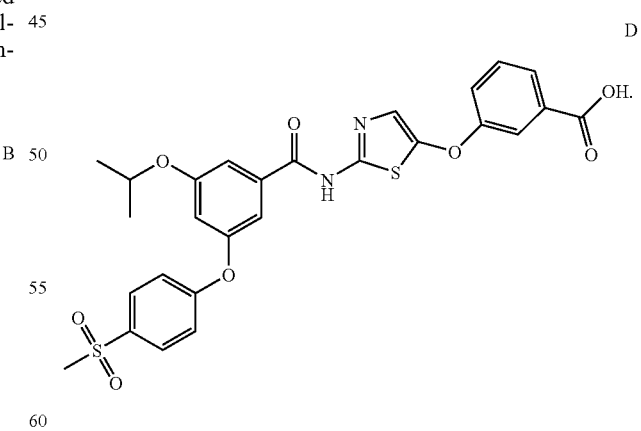

To a solution of Part C compound (20 mg, 0.034 mmol) in THF (1 mL) was added 1N aqueous NaOH (0.051 mL, 0.051 mmol). The reaction was stirred at 25° C. for 18 h. An additional 2.5 equiv of 1N aqueous NaOH were added over a period of 2 days. When the reaction was complete, the mixture was neutralized with 1N aqueous HCl and was extracted with EtOAc. The organic layer was dried (MgSO₄) and concentrated in vacuo. The residue was purified by preparative HPLC (Phenomenex Luna AXIA 5u C18 30×100 mm column; detection at 220 nm; flow rate=40 mL/min; continuous gradient from 50% B to 100% B over 10 min+2 min hold time at 100% B, where A=90:10:0.1H$_2$O:MeOH:TFA and B=90:10:0.1 MeOH:H$_2$O:TFA) to provide the title compound (19.6 mg, quantitative yield) as a solid white lyophilate. [M+H]$^+$=569.5; $^1$H NMR (500 MHz, CDCl$_3$) δ 7.92 (d, J=10 Hz, 2H), 7.82 (d, 1H), 7.76 (s, 1H), 7.45 (m, 2H), 7.31 (m, 2H), 7.15 (m, 3H), 6.83 (s, 1H), 4.68 (m, 1H), 3.07 (s, 3H), 1.37 (m, 6H).

Example 45

A

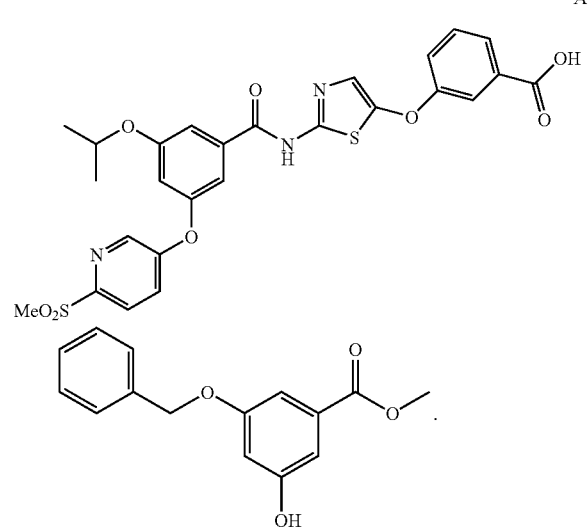

To a stirred suspension of methyl 3,5-dihydroxybenzoate (5 g, 29.7 mmol) and K$_2$CO$_3$ (6.16 g, 44.6 mmol) in DMF (15 mL) was added benzyl bromide (4.95 mL, 41.6 mmol) over 30 min. The reaction was stirred at 25° C. for 18 h, then was filtered. The filtrate was diluted with DCM and washed with 1N aqueous HCl, saturated aqueous NH$_4$Cl, and brine. The organic layer was dried (MgSO$_4$) and concentrated in vacuo. The crude (white solid) residue was chromatographed (the crude product was dissolved in a small amount of DCM and loaded onto a 330 g SiO$_2$ cartridge which was eluted with an 80 min gradient from 0-60% EtOAc/Hexanes) to provide Part A compound (2.10 g, 27% yield) as a white solid. [M+H]+=259.1.

B

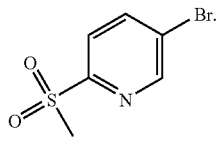

A solution of 5-bromo-2-(methylthio)pyridine (300 mg, 1.470 mmol) and Oxone® (2078 mg, 3.38 mmol) in iPrOH (20 mL) and H$_2$O (10 mL) was stirred at RT overnight. The solid was filtered off. The filtrate was concentrated in vacuo, then was re-dissolved in EtOAc (100 mL), and washed with H$_2$O (2×20 mL) and brine (10 mL). The organic layer was dried (MgSO$_4$) and concentrated in vacuo to give Part B compound (349.2 mg, 1.479 mmol, 101% yield) as a white solid. [M+H]$^+$=236/238.

C

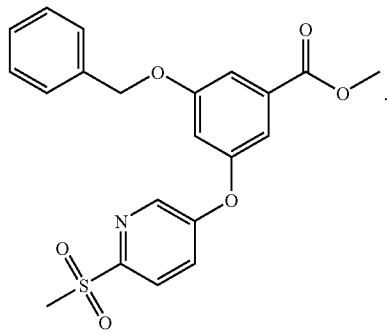

To a stirred solution of Part A compound (1 g, 3.87 mmol) and Part B compound (0.914 g, 3.87 mmol) in DMF (5 mL) was added K$_2$CO$_3$ (0.803 g, 5.81 mmol). The reaction was stirred at 80° C. for 24 h. More K$_2$CO$_3$ (0.5 eq, 250 mg) was added, and the reaction was stirred at 120° C. for 18 h. The reaction was cooled to RT and was diluted with EtOAc and washed with H$_2$O, and brine. The organic layer was dried (Na$_2$SO$_4$) and concentrated in vacuo. The crude residue was chromatographed (the crude product was dissolved in a small amount of DCM and loaded onto a 120 g SiO$_2$ cartridge which was eluted using a 50 min gradient from 0-100% EtOAc/hexanes, followed by 20 min at 100% EtOAc) to give Part C compound (1.26 g, 79% yield) as an off white solid. [M+H]+=414.1.

D

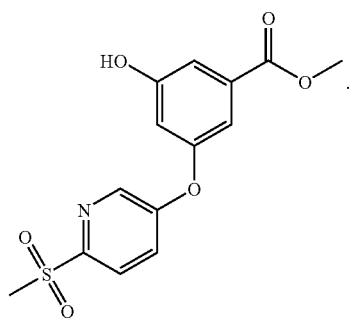

To a solution of Part C compound (1.26 g, 3.05 mmol) in EtOAc (20 mL) and EtOH (20 mL) was added 10% Pd/C (wet) (3.24 g, 3.05 mmol). The reaction was stirred under a H$_2$ (g) balloon at 25° C. for 18 h. The Pd/C was removed by filtration, and the filter cake was washed with EtOAc (3×). The filtrate was concentrated in vacuo to provide Part D compound (975 mg, 99% yield) as a colorless oil. [M+H]+=324.0.

E

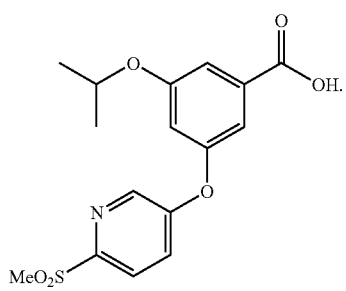

To a solution of Part D compound (160 mg, 0.495 mmol) and 2-iodopropane (168 mg, 0.990 mmol) in DMF (2 mL) was added $K_2CO_3$ (205 mg, 1.485 mmol). The reaction was stirred at 120° C. for 48 h. More $K_2CO_3$ (205 mg, 1.485 mmol) was added, and the reaction was stirred at 120° C. for 18 h. This was repeated 3 additional times until the reaction was complete. The reaction was cooled to RT and was filtered. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1$H_2O$:MeOH:TFA and B=90:10:0.1 MeOH:$H_2O$:TFA) to provide the desired Part E compound (72.6 mg, 41.8% yield) as a yellow oil. $[M+H]^+=352.1$.

h. More 1N aqueous NaOH (0.1 mL, 0.1 mmol) was added, and the reaction was stirred at 25° C. for several hours. The reaction was neutralized with 1N aqueous HCl and concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1$H_2O$:MeOH:TFA and B=90:10:0.1 MeOH:$H_2O$:TFA) to provide the title compound (46.5 mg, 73% yield) as a solid white lyophilate. $[M+H]^+=570.0$; $^1H$ NMR (400 MHz, MeOH-$d_4$) δ 8.82 (s, 2 H), 8.10 (m, 2 H), 7.80 (m, 1 H), 7.72 (s, 1 H), 7.64 (m, 1 H), 7.50 (m, 1H), 7.35 (m, 1H), 7.20 (s, 1H), 7.02 (s, 1H), 4.73 (m, 1H), 3.40 (m, 3H), 1.35 (m, 6H).

Example 46

F

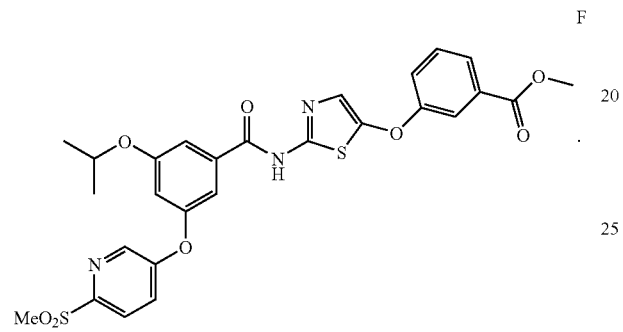

To a solution of Part E compound (72.6 mg, 0.207 mmol) and Hunig's base (0.108 mL, 0.620 mmol) in DCM (2 mL) and DMF (0.025 mL) was added EDC (79 mg, 0.413 mmol), followed by addition of HOBt monohydrate (63.3 mg, 0.413 mmol). The reaction mixture was stirred at 25° C. for 5 min, and then Example 4 Part A compound (78 mg, 0.310 mmol) was added. The reaction was stirred at 25° C. for 48 h, then was concentrated in vacuo. The residue was taken up in MeOH, filtered to remove solid impurities, and purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1$H_2O$:MeOH:TFA and B=90:10:0.1 MeOH:$H_2O$:TFA) to provide Part F compound (65.3 mg, 54% yield) as an orange oil. $[M+H]+=584.0$.

A

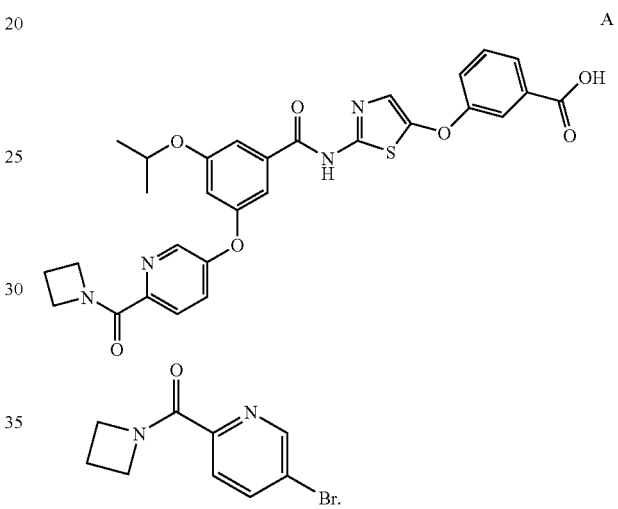

Part A compound was prepared according to WO 2007/007041 (McKerrecher, D. et al., "Preparation of heteroaryl benzamide derivatives as glucokinase activators for the treatment of diabetes", PCT Int. Appl. 2007).

B

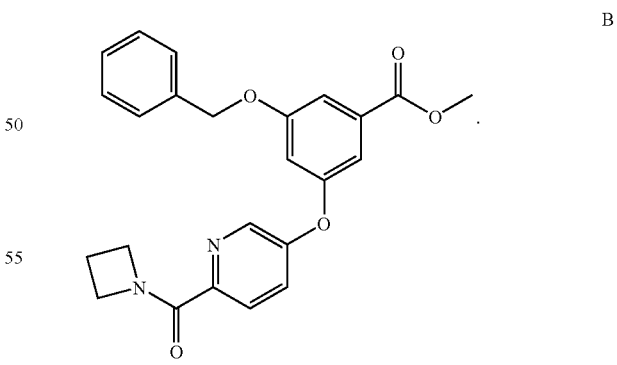

G

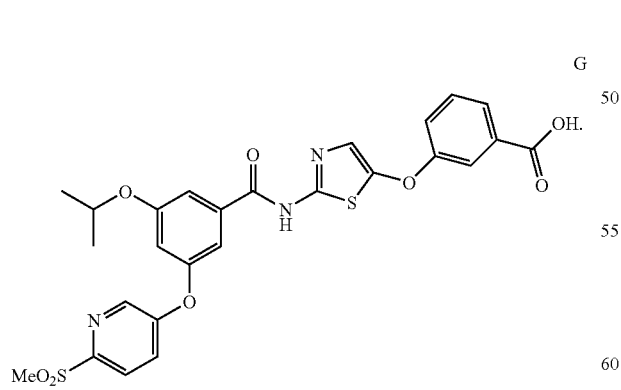

To a solution of Part F compound (65.3 mg, 0.112 mmol) in THF (2 mL) was added 1N aqueous NaOH (0.201 mL, 0.201 mmol). The reaction was stirred at 25° C. for several hours. An additional portion of 1N aqueous NaOH (0.201 mL, 0.201 mmol) was added, and the reaction was stirred at 25° C. for 18

To a stirred solution of Example 45 Part A compound (250 mg, 0.968 mmol) and Part A compound (233 mg, 0.968 mmol) in DMF (2 mL) was added $K_2CO_3$ (201 mg, 1.452 mmol). The reaction was stirred at 80° C. for 24 h, then at 120° C. for 18 h. An additional portion of $K_2CO_3$ (0.5 eq, 67 mg) was added, and the reaction was stirred at 120° C. for 18 h. The reaction was cooled to RT, filtered, and diluted with MeOH. The solution was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10:0.1 MeOH:H$_2$O:TFA) to provide Part B compound (100 mg, 25% yield) as a brown oil. [M+H]$^+$=419.1.

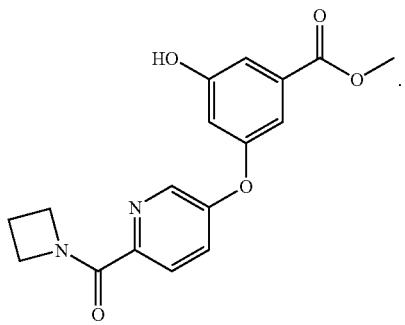

C

To a solution of Part B compound (100 mg, 0.239 mmol) in EtOAc (2 mL) and EtOH (2.000 mL) was added 10% Pd/C (wet) (127 mg, 0.119 mmol). The reaction was stirred under a H$_2$ (g) balloon at 25° C. for 18 h. The Pd/C was filtered off, and the filtrate was concentrated in vacuo to provide Part C compound (65 mg, 83% yield) as a white solid. [M+H]+=329.1.

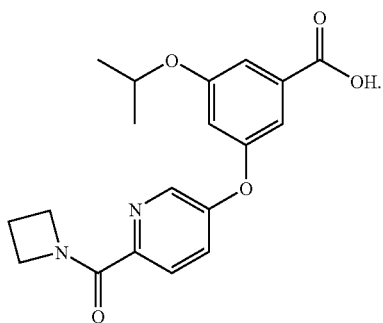

D

To a solution of Part C compound (65 mg, 0.198 mmol) and 2-iodopropane (67.3 mg, 0.396 mmol) in DMF (2 mL) was added K$_2$CO$_3$ (82 mg, 0.594 mmol). The reaction was stirred at 120° C. for several hours. The reaction was cooled to 80° C. and was stirred for 18 h. A portion of LiCl (16.79 mg, 0.396 mmol) was added, and the reaction was stirred at 120° C. for 24 h. More LiCl (16.79 mg, 0.396 mmol) was added and the reaction was stirred at 120° C. for 18 h, then was cooled to RT, filtered, and diluted with MeOH. The mixture was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10:0.1 MeOH:H$_2$O:TFA) to provide Part D compound (27.4 mg, 38.8% yield) as a brownish oil. [M+H]$^+$=357.1.

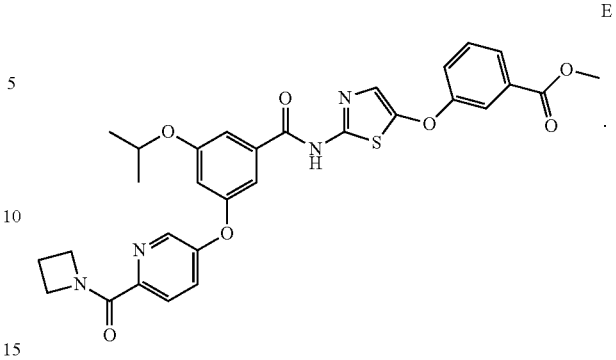

E

To a solution of Part D compound (27.4 mg, 0.077 mmol) and Hunig's base (0.040 mL, 0.231 mmol) in DCM (2 mL) and DMF (0.025 mL) was added EDC (29.5 mg, 0.154 mmol), followed by HOBt monohydrate (23.55 mg, 0.154 mmol). The reaction mixture was stirred at 25° C. for 5 min, and then Example 4 Part A compound (28.9 mg, 0.115 mmol) was added. The reaction was stirred at 25° C. for 48 h, then was concentrated in vacuo. The residue was taken up in MeOH, filtered, and purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10:0.1 MeOH:H$_2$O:TFA) to provide Part E compound (14 mg, 31% yield) as a cloudy oil. [M+H]$^+$=589.0.

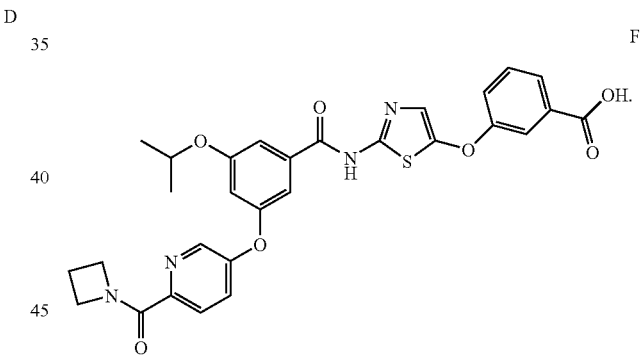

F

To a solution of Part E compound (14 mg, 0.024 mmol) in THF (1 mL) was added 1N aqueous NaOH (0.036 mL, 0.036 mmol). The reaction was stirred at 25° C. for several h. More 1N aqueous NaOH (0.036 mL, 0.036 mmol) was added and the reaction was stirred at 25° C. for 18 h. More 1N aqueous NaOH (0.036 mL, 0.036 mmol) was added, and the reaction was stirred at 25° C. for several hours. The reaction was purified directly by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10: 0.1H$_2$O:MeOH:TFA and B=90:10:0.1 MeOH:H$_2$O:TFA) to provide the title compound (5.9 mg, 43% yield) as an off-white solid lyophilate. [M+H]$^+$=575.0; $^1$H NMR (500 MHz, CDCl$_3$) δ 8.27 (s, 1 H), 7.97 (m, 1 H), 7.73 (m, 1 H), 7.67 (s, 1 H), 7.34 (m, 2 H), 7.30 (s, 1H), 7.25 (m, 1H), 7.17 (s, 1H), 6.71 (s, 1H), 4.64 (m, 2H), 4.55 (m, 1H), 4.16 (m, 2H), 2.29 (m, 2 H), 1.28 (m, 6H).

Example 47

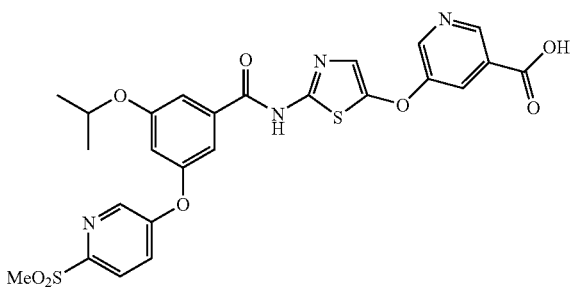

A

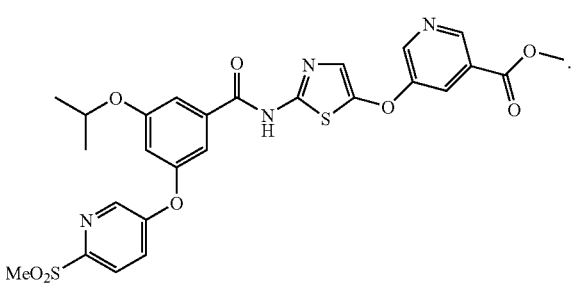

To a solution of Example 45 Part E compound (130 mg, 0.370 mmol) and Example 36 Part B compound (139 mg, 0.555 mmol) in DCM (5 mL) was added PyBOP (385 mg, 0.740 mmol) and Hunig's base (0.258 mL, 1.480 mmol). The reaction was stirred at 25° C. for 18 h, then was concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10: 0.1 MeOH:H$_2$O:TFA) to provide Part C compound (36 mg, 16% yield) as a brown oil. [M+H]+=585.5 g/mol.

B

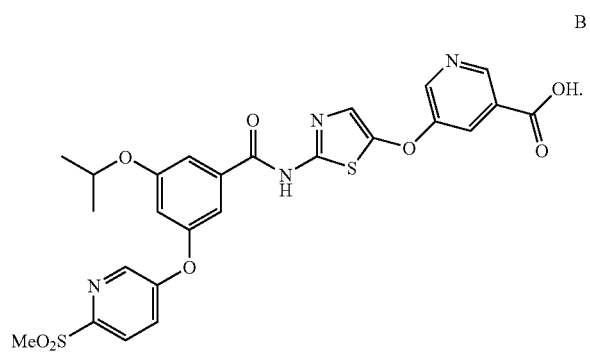

Part A compound (36 mg) was taken up in THF (3 mL) and H$_2$O (0.3 mL), and LiOH.H$_2$O (13.29 mg, 0.555 mmol) was added. The reaction was stirred at 25° C. for several hours, then was neutralized with 1N aqueous HCl and concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1H$_2$O:MeOH:TFA and B=90:10: 0.1 MeOH:H$_2$O:TFA) to provide the title compound (10.5 mg, 30% yield) as an off-white solid lyophilate. [M+H]$^+$=570.9; $^1$H NMR (400 MHz, CDCl$_3$) δ 8.97 (s, 1H), 8.63 (s, 1H), 8.50 (m, 1H), 8.08 (d, J=8.8 Hz, 1H), 7.99 (m, 1H), 7.52 (m, 1H), 7.43 (s, 1H), 7.29 (s, 1H), 7.19 (s, 1H), 6.84 (m, 1H), 4.66 (m, 1H), 3.39 (s, 3H), 1.38 (m, 6H).

Assay and Biological Data

Compounds of formula I of the invention, including compounds described in the Examples hereof, have been tested in the following assay and have shown to be activators of glucokinase. In general, compounds of the present invention, such as particular compounds disclosed in the following examples, have been identified to enhance the activity of glucokinase at concentrations equivalent to, or more potently than, 100 μM, preferably 10 μM, more preferably 1 μM, thereby demonstrating compounds of the present invention as especially effective enhancers of activity of glucokinase. Potencies can be calculated and expressed as either EC$_{50}$ (concentration to achieve 50% of full activation) and/or the maximum percentage activation above background, and refer to activity measured employing the assay system described below.

Compounds of formula I of the invention, including compounds described in the Examples hereof, have been tested in the following assay and have shown to be activators of glucokinase.

Glucokinase Tandem Enzymatic Assay

Enzymatic activity of human glucokinase (GK) was measured by incubating GK, ATP, and glucose for discrete time periods followed by quenching with EDTA (ethylenediamine tetra-acetic acid). Relative amounts of product glucose-6-phosphate (G6P) were measured by then running a detection assay using G6P dehydrogenase and measuring the conversion of ThioNAD (thio-nicotinamide adenine dinucleotide) to ThioNADH (thio-dihydronicotinamide adenine dinucleotide) at a wavelength of 405 nm. This 'uncoupled' enzymatic reaction is denoted as the GK 'tandem' assay. Activation of GK by compounds can be assessed using this assay. The GK tandem assay protocol described below was followed using a range of activator compound concentrations from 0 to 100 μM at 5 and 12 mM of glucose. Human full-length glucokinase (GK, 15 nM) was incubated with 5 or 12 mM glucose in a 384 well black microtiter plate with a clear bottom. To initiate the GK reaction, magnesium-ATP (3 mM final concentration) was added to GK in buffer (final buffer conditions of 25 mM HEPES buffer, pH 7.1, containing 1 mM dithiothreitol and 5% DMSO). The total reaction volume was 20 μL. The reaction was allowed to proceed for ten minutes and was then quenched with 5 μL EDTA; 45 mM final). The components of the detection reaction, ThioNAD and G6PDH (glucose-6-phosphate dehydrogenase) (final concentrations of 650 μM and 3.33 Units, respectively), were then added together in a volume of 25 μL, (to give a total volume of 50 μL). Absorbance measurements were made at 405 nm on a Spectramax Plus 384 absorbance plate reader (Molecular Devices). Absorbance was read, background glucose-6-phosphate levels were subtracted, after which activation was calculated as a percentage of control activity. Control activity was determined using GK in the presence of vehicle (DMSO), with background glucose-6-phosphate subtracted. Background glucose-6-phosphate was determined by pre-quenching GK with EDTA prior to reaction initiation with ATP.

Expression and Purification of Human GK

Full-length human hepatic GK (untagged) was expressed in BL21 STAR (DE3)pLysS cells (Invitrogen) at 25° C. as described by Mookhtiar et al. (1). The protein was purified essentially as described by Lange (2) with a slight modification. Briefly, cell pellets were lysed via three rounds of freezing and thawing, centrifuged at 15000 g for clarification, and precipitated with 40-65% (NH4)2SO4. The resulting pellet was resuspended in buffer, dialyzed, and applied directly to a Q-Sepharose (Sigma) column followed by elution with a linear 100-600 mM KCl gradient. GK containing fractions were pooled, dialyzed overnight vs. 25 mM Hepes pH 7.2/1 mM MgCl2/1 mM EDTA/0.1 M KCl/1 mM DTT, then dialyzed again with same buffer with 10% glycerol added.

REFERENCES

1. Mookhtiar, K. A. et al., "Heterologous expression and characterization of rat liver glucokinase regulatory protein", *Diabetes*, 45:1670-1677 (1996).
2. Lange, A. J. et al., "Expression and site-directed mutagenesis of hepatic glucokinase", *Biochem. J.*, 277:159-163 (1991).

Biological data for Example compounds tested are shown in the table below.

| Example No. | $EC_{50}$ (nM) with Human Glucokinase @ 12 mM Glucose |
|---|---|
| 33 | 6 |
| 3 | 13 |
| 34 | 16 |
| 45 | 34 |
| 4 | 47 |
| 42 | 170 |
| 11 | 171 |
| 17 | 179 |

For other Examples, the $EC_{50}$ values could not be calculated from the activation curves, so the maximal activation data (expressed as a % of basal activation) for the Example compounds tested are shown in the table below.

| Example No. | Maximal activation (%) Human Glucokinase @ 12 mM Glucose |
|---|---|
| 32 | 118% |
| 38 | 144% |
| 46 | 124% |

In Vivo Studies: Oral Glucose Tolerance Test (OGTT)

Oral glucose tolerance tests were carried out on male DIO (diet-induced obese) C57BL/6J mice fed a high fat diet (60% kcal from fat) for 26 weeks prior to experimentation. Mice were fasted overnight before use for experiments. A test compound or vehicle (10% dimethyl acetamide+10% ethanol+10% Cremophore+70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under-the-curve (ΔAUC) from 0-120 min was calculated (the time glucose administration being time zero).

The Example compound in the table below reduces glucose AUC levels in an OGTT test in DIO mice as described above.

| Example No. | Reduction in Glucose AUC at 30 mg/kg dose |
|---|---|
| 4 | 37% |

What is claimed is:
1. A compound having the structure

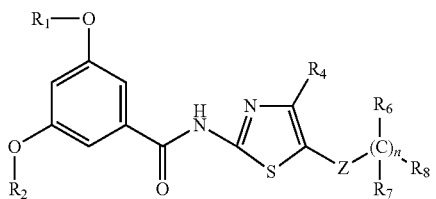

or stereoisomers or a pharmaceutically acceptable salt thereof;
wherein
  $R_1$ is selected from
    alkyl optionally substituted with —OH or alkoxy,
    aryl,
    arylalkyl, or
    heteroaryl optionally substituted with F or Cl;
  $R_2$ is selected from
    alkyl,
    aryl optionally substituted with —S(O)$_2$(alkyl),
    arylalkyl, or
    heteroaryl optionally substituted with —S(O)$_2$(alkyl) or —C(O)(heterocyclo);
  Z is selected from , O, S, S(O), or S(O)$_2$;
  $R_4$ is selected from H or alkyl;
  $R_6$ and $R_7$ are independently selected from H, halogen, or alkyl;
  $R_8$ is selected from aryl or heteroaryl;
  wherein $R_8$ is substituted with at least one substituent selected from —C(O)NR$^f$R$^g$;  1)

—NHC(O)R$^h$;  2)

—OC(O)NHR$^h$;  3)

alkoxy;  4)

tetrazolyl;  5)

—SO$_2$NR$^i$R$^j$;  6)

CN;  7)

—C(O)OH;  8)

—C(O)O(alkyl);  9)

halo or —CF$_3$;  10)

—P(O)(OR$^f$)(OR$^g$);;  11)

alkyl;  12)

-continued

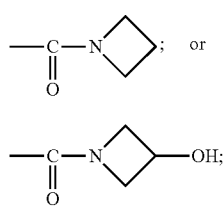

where $R^f$ and $R^g$ are independently selected from H, alkyl and aryl;
$R^h$ is alkyl or aryl; and
$R^i$ and $R^j$ are independently selected from H, alkyl and aryl;
provided that at least one of $R^i$ and $R^j$ is other than H; and
n is 0, 1, 2, or 3.

2. The compound as defined in claim 1 wherein $R_1$ is i-propyl and $R_4$ is H.

3. The compound as defined in claim 1 wherein $R_4$ is H.

4. The compound as defined in claim 1 having the structure

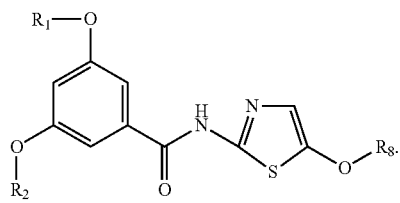

5. The compound as defined in claim 1 wherein Z is O.

6. The compound as defined in claim 4 wherein
$R_1$ is alkoxyalkyl, hydroxyalkyl, alkyl, heteroaryl or haloheteroaryl;
$R_2$ is phenyl, phenyl-S(O)$_2$(CH$_3$), C$_{1-3}$alkyl phenylalkylenyl, or pyridinyl or pyrazinyl substituted with heterocyclocarbonyl;
$R_8$ is phenyl, pyridinyl, pyrimidinyl, or quinolinyl,
wherein $R_8$ is substituted with 1 to 4 substituents independently selected from —CN, —C(O)NH$_2$, —C(O)OH, —OCH$_3$, tetrazolyl, C$_{1-3}$alkyl, F, Cl, —CF$_3$, or —P(O)(OCH$_2$CH$_3$)$_2$.

7. The compound as defined in claim 4 wherein
$R_1$ is alkoxyalkyl, hydroxyalkyl or alkyl;
$R_2$ is phenyl-S(O)$_2$(CH$_3$), phenylalkylenyl, pyridinyl or pyrazinyl substituted with heterocyclocarbonyl; and
$R_8$ is phenyl substituted with 1 to 4 substituents independently selected from CN, —C(O)NR$^f$R$^g$, —C(O)OH, alkoxy, tetrazolyl, alkyl, halo, CF$_3$, or —SO$_2$NR$^i$R$^j$.

8. The compound as defined in claim 1 wherein
$R_1$ is CH$_3$OCH$_2$CH(CH$_3$)—, HOCH$_2$CH(CH$_3$)—, i-C$_3$H$_7$, CH$_3$,

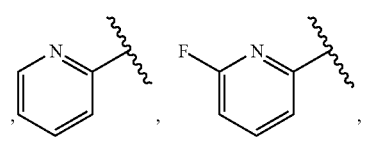

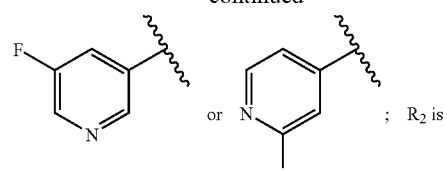; $R_2$ is

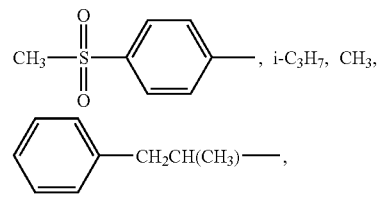, i-C$_3$H$_7$, CH$_3$,

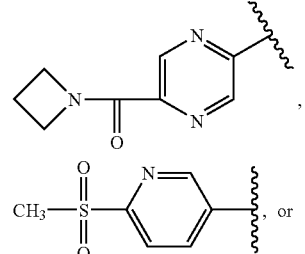

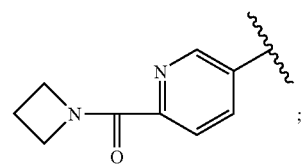, or

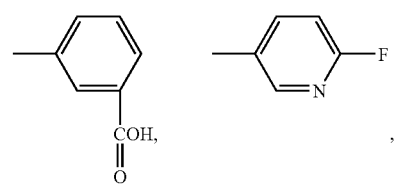;

$R_4$ is H;
Z is O;

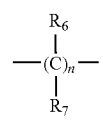

is a bond; and $R_8$ is 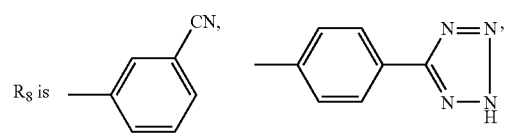

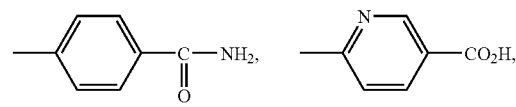

-continued
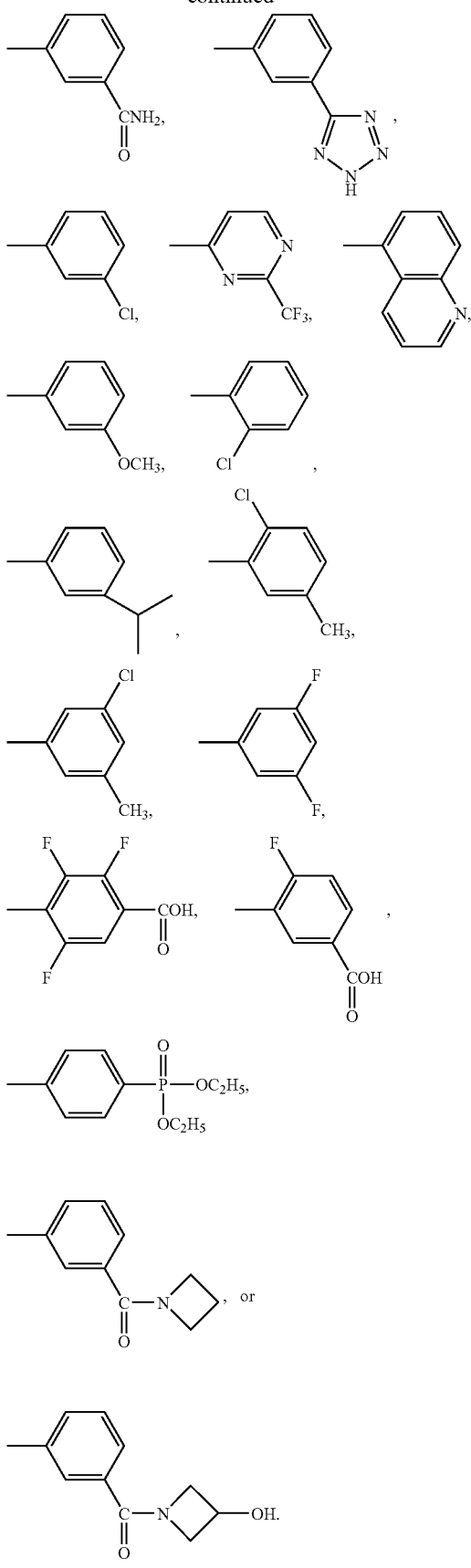
9. The compound as defined in claim 1 which is
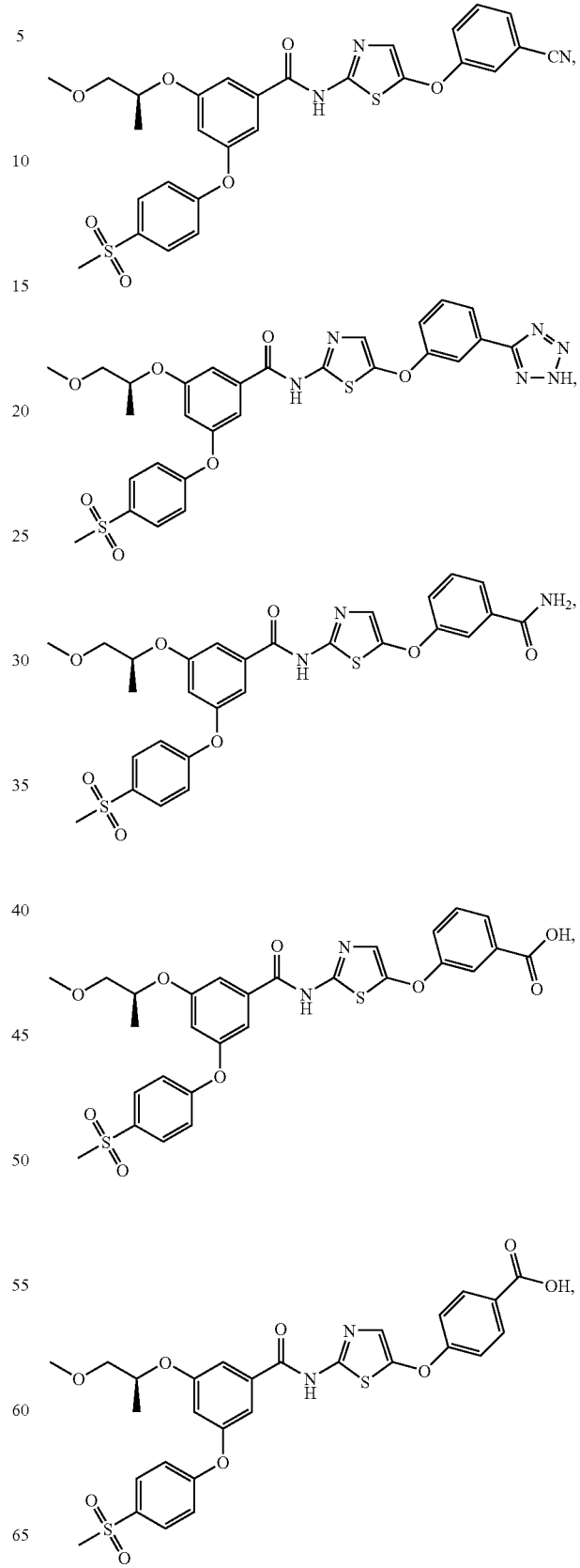

103
-continued
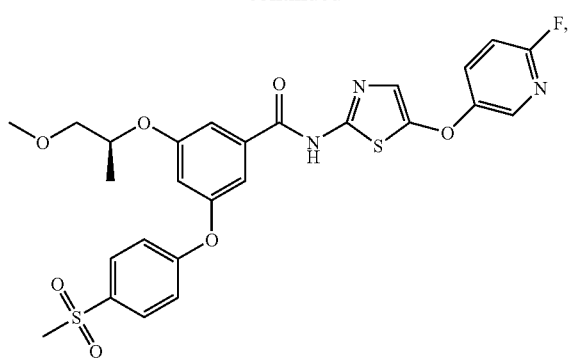
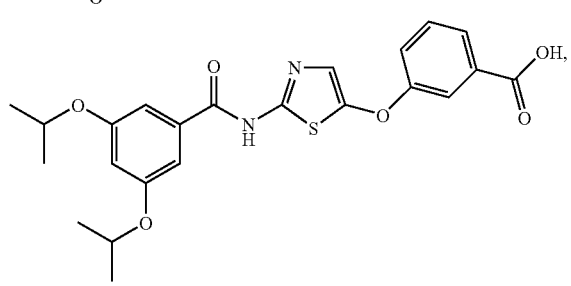
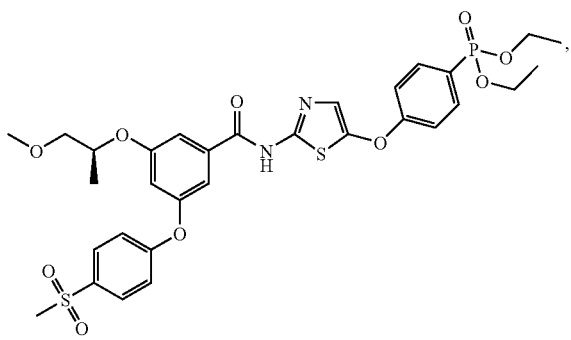
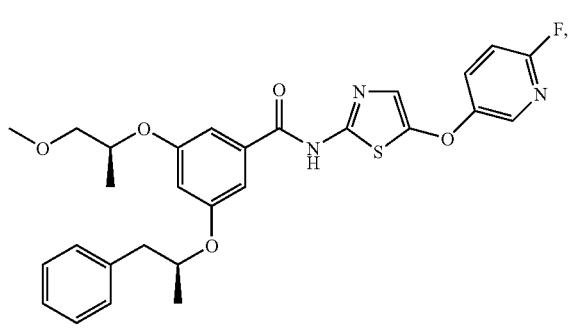
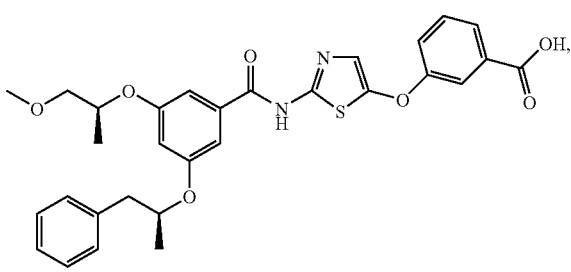
104
-continued
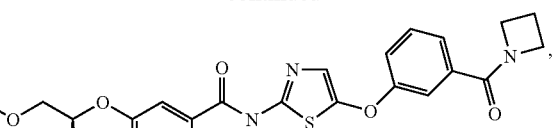
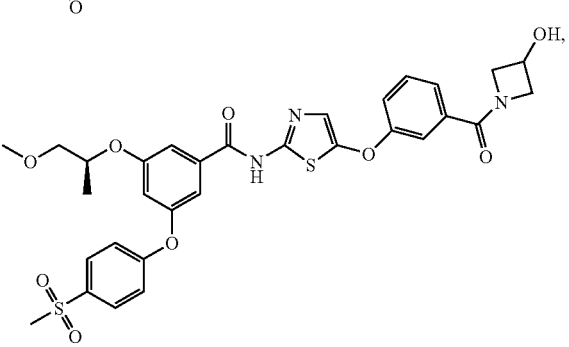
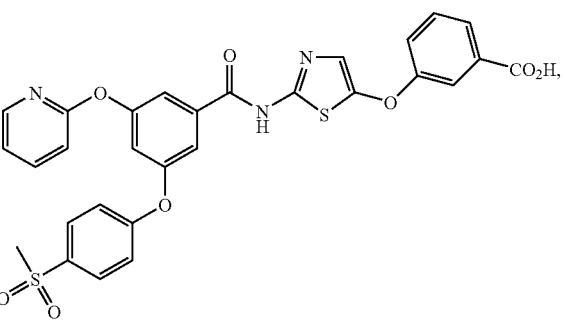
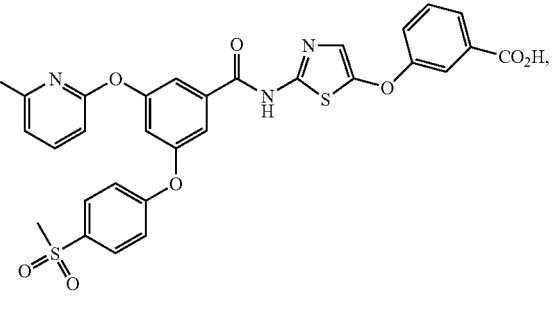
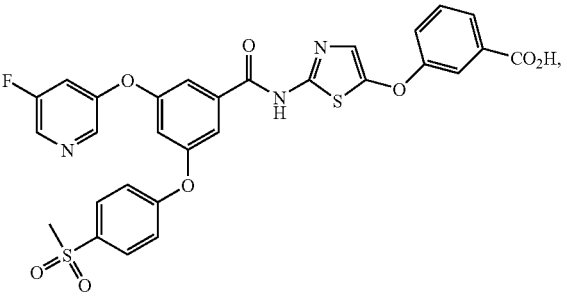

-continued

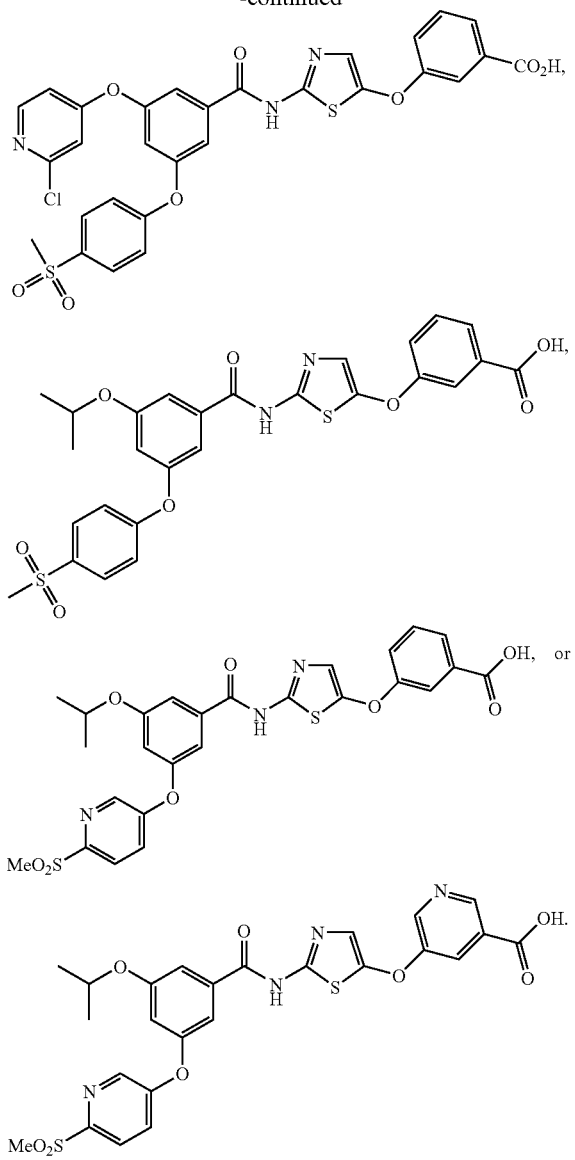

10. A pharmaceutical composition comprising a compound as defined in claim 1 and a pharmaceutically acceptable carrier thereof.

11. A pharmaceutical composition comprising a compound as defined in claim 1 and another therapeutic agent which is an anti-diabetic agent, anti-hyperglycemic agent, anti-hyperinsulinemic agent, anti-retinopathic agent, anti-neuropathic agent, anti-nephropathic agent, anti-atherosclerotic agent, anti-infective agent, anti-ischemic agent, anti-hypertensive agent, anti-obesity agent, anti-dyslipidemic agent, anti-hyperlipidemic agent, anti-hypertriglyceridemic agent, anti-hypercholesterolemic agent, anti-ischemic agent, anti-cancer agent, anti-cytotoxic agent, anti-restenotic agent, anti-pancreatic agent, lipid lowering agent, appetite suppressant, memory enhancing agent, or cognitive agent.

12. A method for treating or slowing the progression of a disease requiring glucokinase activator therapy, which comprises administering to a mammalian patient in need of treatment a compound of formula I as defined in claim 1, wherein said disease is diabetes mellitus or hyperglycemia.

13. A method of activating the enzyme glucokinase, which comprises administering to a mammalian patient an activating amount of a compound of the formula I as defined in claim 1.

14. A method of treating Type II diabetes, which comprises administering to a patient in need of treatment a compound as defined in claim 1.

15. The compound as defined in claim 1 which is

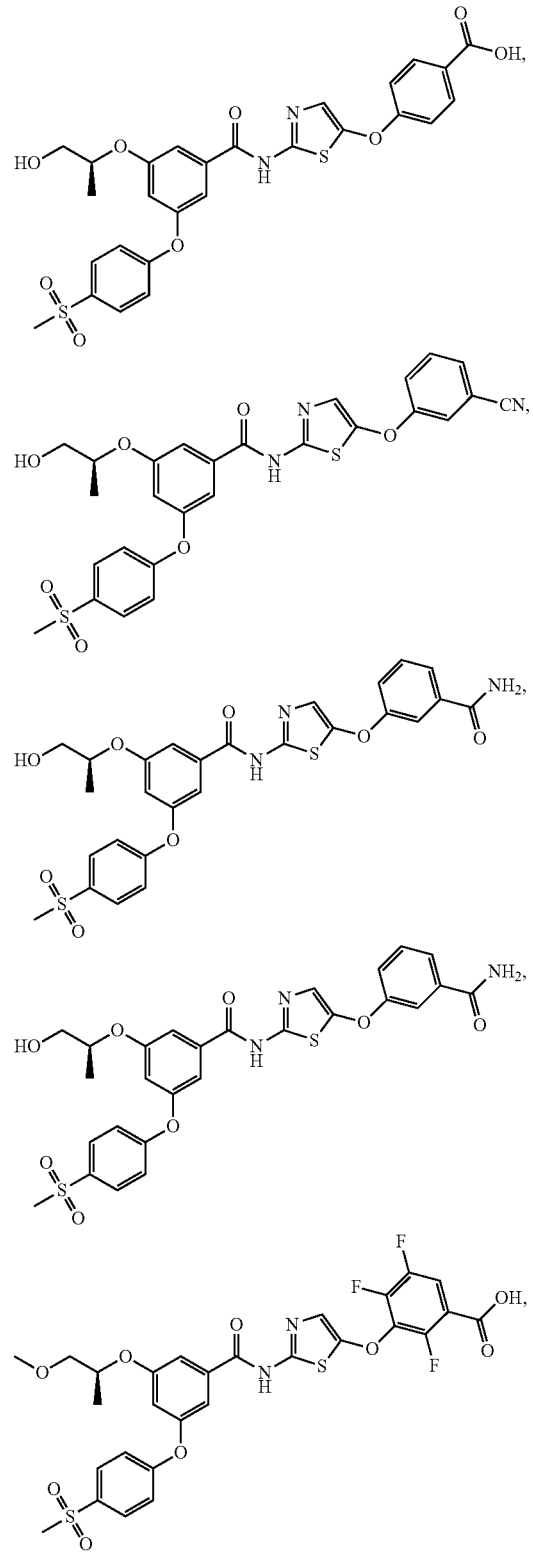

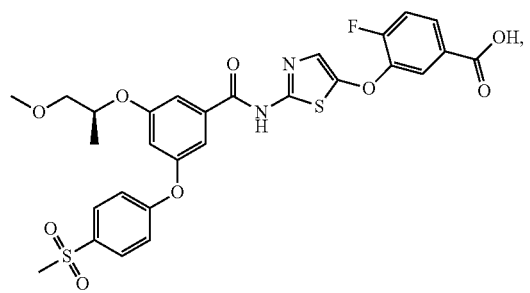
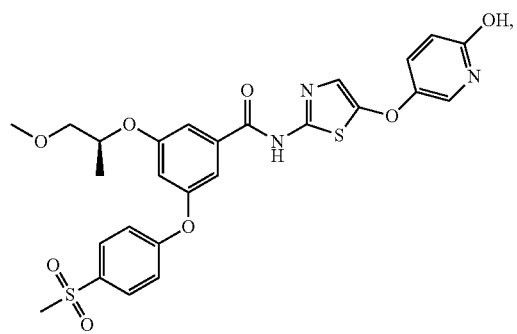
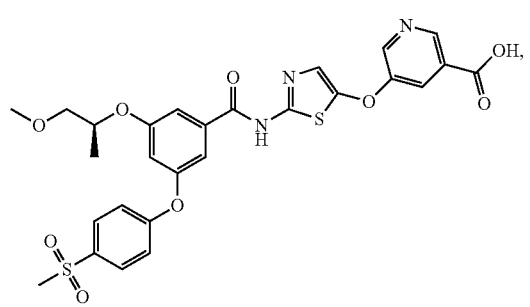
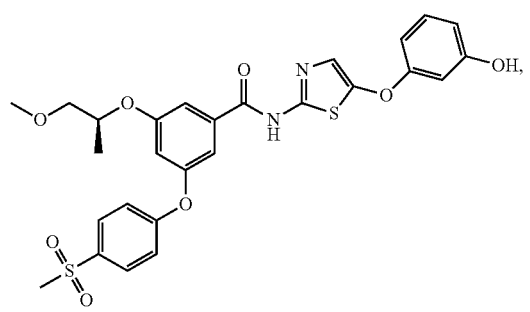
or
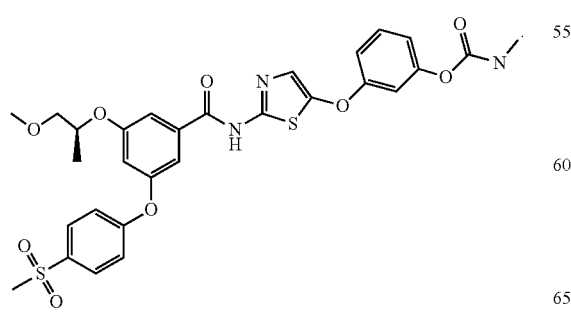
16. The compound as defined in claim 1 which is
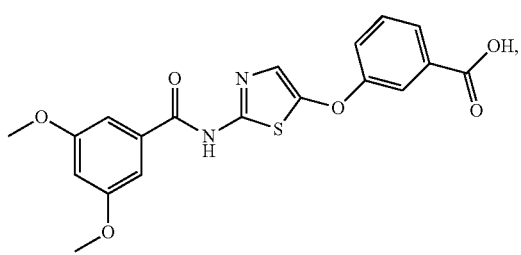
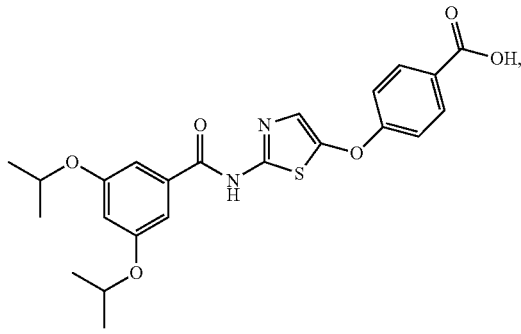
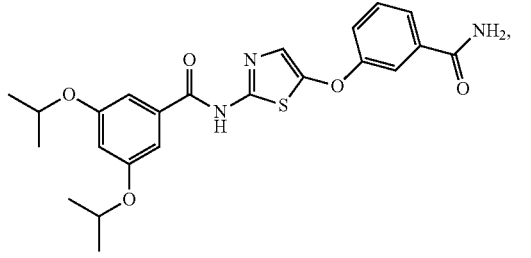
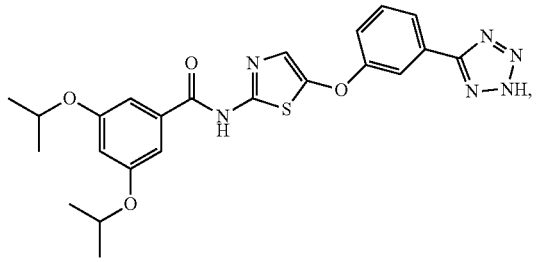
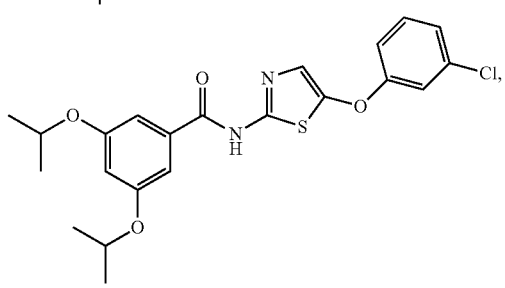
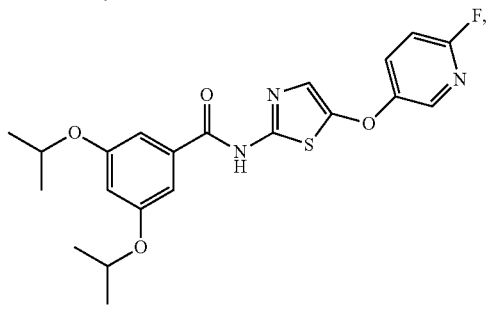

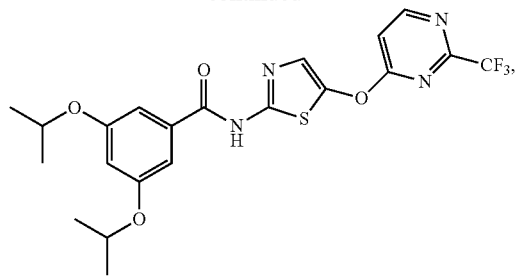
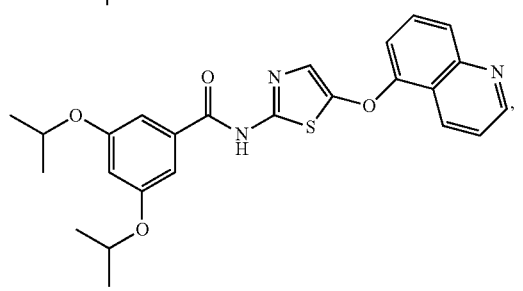
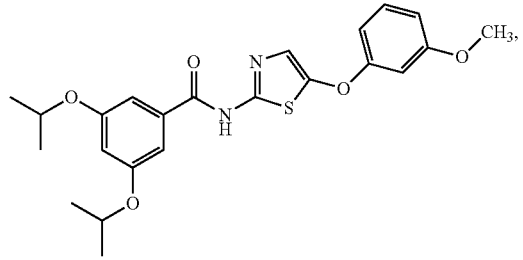
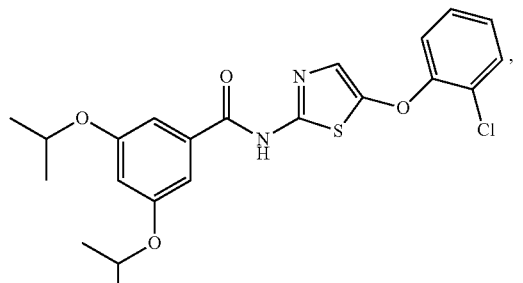
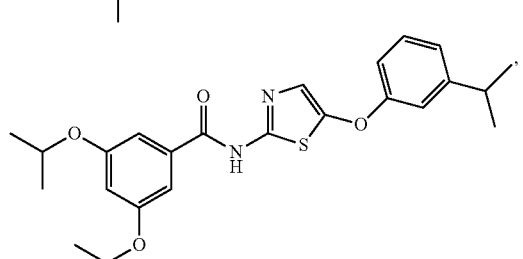
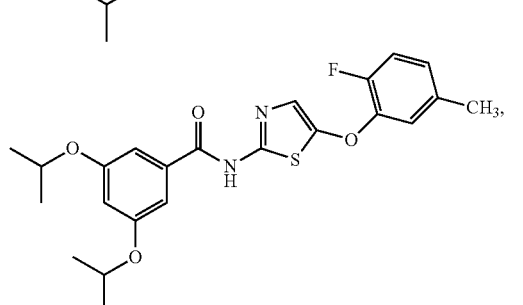
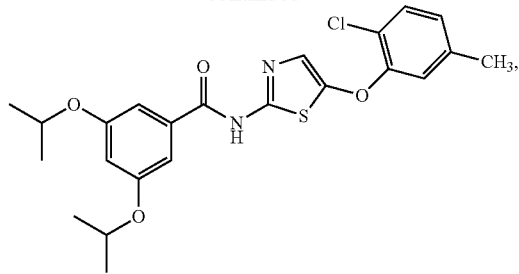
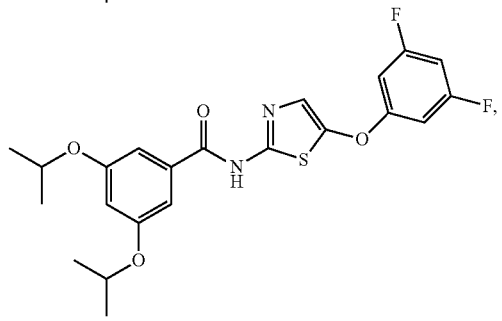
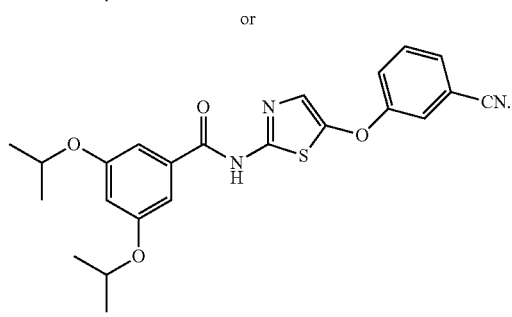
or
17. The compound as defined in claim 1 which is
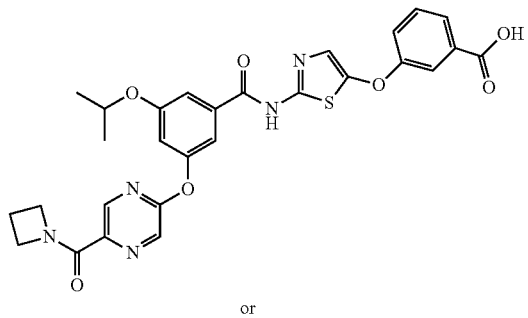
or
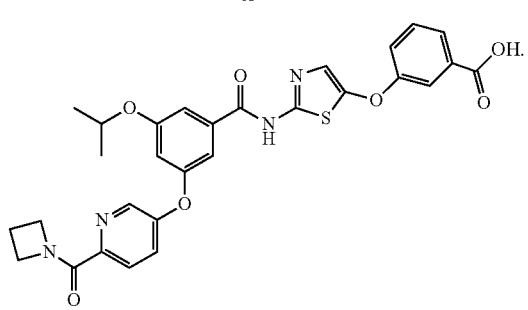
* * * * *

UNITED STATES PATENT AND TRADEMARK OFFICE
CERTIFICATE OF CORRECTION

PATENT NO. : 8,222,285 B2
APPLICATION NO. : 12/663807
DATED : July 17, 2012
INVENTOR(S) : Sean Chen et al.

Page 1 of 1

It is certified that error appears in the above-identified patent and that said Letters Patent is hereby corrected as shown below:

On the Title Page:

Item (57), ABSTRACT:

Column 2, line 3 (Abstract), after "wherein", insert --  --.

In the Claims:

Claim 1:

Column 98, line 35, after "from", delete ",".

Claim 6:

Column 99, line 40, after "alkyl", insert -- , --.

Claim 8:

Column 99, line 66, before " 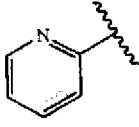 ", delete ",".

Signed and Sealed this
Twenty-eighth Day of May, 2013

Teresa Stanek Rea
*Acting Director of the United States Patent and Trademark Office*